(12) United States Patent
Davé et al.

(10) Patent No.: US 11,078,164 B1
(45) Date of Patent: Aug. 3, 2021

(54) PTEN BINDING COMPOUNDS, FORMULATIONS, AND USES THEREOF

(71) Applicant: University of South Florida, Tampa, FL (US)

(72) Inventors: Vrushank G. Davé, Tampa, FL (US); Jianfeng Cai, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 16/821,269

(22) Filed: Mar. 17, 2020

Related U.S. Application Data

(60) Division of application No. 16/265,662, filed on Feb. 1, 2019, now Pat. No. 10,669,241, which is a continuation of application No. PCT/US2018/000049, filed on Feb. 16, 2018.

(60) Provisional application No. 62/460,324, filed on Feb. 17, 2017.

(51) Int. Cl.
| | |
|---|---|
| *C07D 233/74* | (2006.01) |
| *C07C 311/33* | (2006.01) |
| *C07C 237/06* | (2006.01) |
| *C07D 209/20* | (2006.01) |

(52) U.S. Cl.
CPC .......... *C07D 233/74* (2013.01); *C07C 237/06* (2013.01); *C07C 311/33* (2013.01); *C07D 209/20* (2013.01)

(58) Field of Classification Search
CPC ............................ C07C 237/06; C07D 233/74
See application file for complete search history.

(56) References Cited

U.S. PATENT DOCUMENTS

| | | | |
|---|---|---|---|
| 10,669,241 B2 * | 6/2020 | Dave | ...................... C07C 311/33 |
| 2014/0235546 A1 | 8/2014 | Cunningham et al. | |
| 2015/0274782 A1 | 1/2015 | Cai et al. | |

FOREIGN PATENT DOCUMENTS

| | | |
|---|---|---|
| WO | 2013/112548 A1 | 8/2013 |

OTHER PUBLICATIONS

International Search Report for PCT/US2018/000049 dated May 23, 2018.
Teng, et al. "Small Antimicrobial Agents Based on Acylated Reduced Amide Scaffold," Journal of Medicinal Chemistry, Aug. 15, 2016, vol. 59, pp. 7877-7887.
She, et al. "Helical 1:1 A/Sulfono-Y-AA Heterogeneous Peptides With Antibacterial Activity," Biomacromolecules, Mar. 31, 2016, vol. 17, pp. 1854-1859.
Li, et al. Helical Antimicrobial Sulfono-Y-Aapeptides, Journal of Medicinal Chemistry, May 28, 2015, vol. 58, pp. 4802-4811.
Guan, et al. "Postischemic Administration of a Potent PTEN Inhibitor Reduces Spontaneous Lung Infection Following Experimental Stroke," CNS Neuroscience & Therapeutics, Oct. 25, 2013, vol. 19, pp. 990-993.
Supplementary European Search Report for EP 18 75 3852 dated Oct. 5, 2020.
Khadka Nawal Ket al: "Modulation of lipid membrane structural and mechanical properties by a peptidomimetic derived from reduced amide scaffold", BBA—Biomembranes, Elsevier, Amsterdam, NL, vol. 1859, No. 5, Jan. 26, 2017 (Jan. 26, 2017), pp. 734-744, XP029949422.
Annette C Schmid et al: "Bisperoxovanadium compounds are potent PTEN inhibitors", FEBS Letters, Elsevier, Amsterdam, NL, vol. 561, No. 1-3, Jan. 1, 2004 (Jan. 1, 2004), pp. 35-38, XP008155698.
Ma Su et al: "Membrane-Active Hydantoin Derivatives as Antibiotic Agents", Journal of Medicinal Chemistry, vol. 60, No. 20, Oct. 6, 2017 (Oct. 6, 2017), pp. 8456-8465, XP055733661, us.

\* cited by examiner

*Primary Examiner* — Golam M Shameem
(74) *Attorney, Agent, or Firm* — Thomas | Horstemeyer, LLP

(57) ABSTRACT

Described herein are compounds and formulations thereof that can bind PTEN. Also described herein are methods of using the compounds and formulations thereof that can bind PTEN. In some embodiments, the method can include administering an amount of a compound or formulation described herein to a subject in need thereof.

5 Claims, 21 Drawing Sheets

FIG. 5

| Code | Compound | MW | Structure | % enhanced PTEN activity at 1uM |
|---|---|---|---|---|
| 5 | TP-D-143-6 | 637.85 | 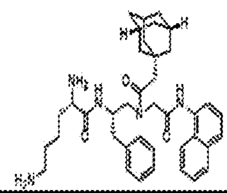 | 36.69724771 |
| 8 | TP-E-041-3 | 703.94 | 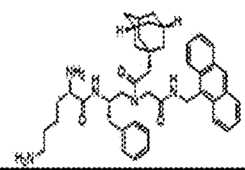 | 75.3604194 |
| 9 | TP-E-059-3 | 792.06 | 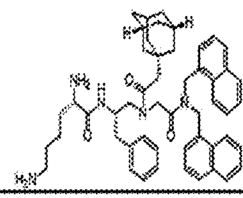 | 31.12712975 |
| 10 | TP-E-064-3 | 878 | 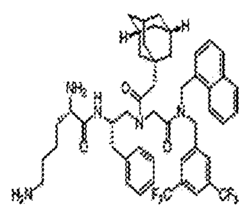 | 28.62873815 |

FIG. 6

| | | | | |
|---|---|---|---|---|
| 11 | TP-E-107-3 | 659.96 | 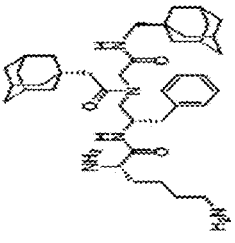 | 32.27571116 |
| 12 | TP-E-135-3 | 774.11 | 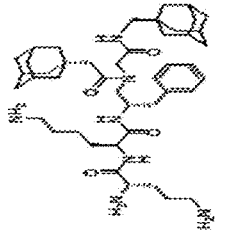 | 14.58789205 |
| 13 | TP-E-136-3 | 816.15 | 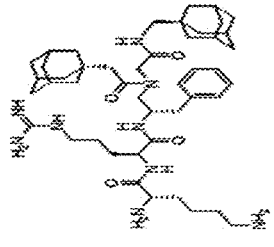 | 48.14004376 |
FIG. 6 (ctd.)

| | | | | |
|---|---|---|---|---|
| 14 | TP-E-141-3 | 669.83 | (structure) | 33.36980306 |
| 39 | TP-E-022-3 | 651.88 | (structure) | 19.16622505 |
| 40 | TP-E-044-6 | 698.92 | (structure) | 22.69916976 |
| 43 | TP-E-068-3 | 677.92 | (structure) | 79.75622682 |

FIG. 6 (ctd.)

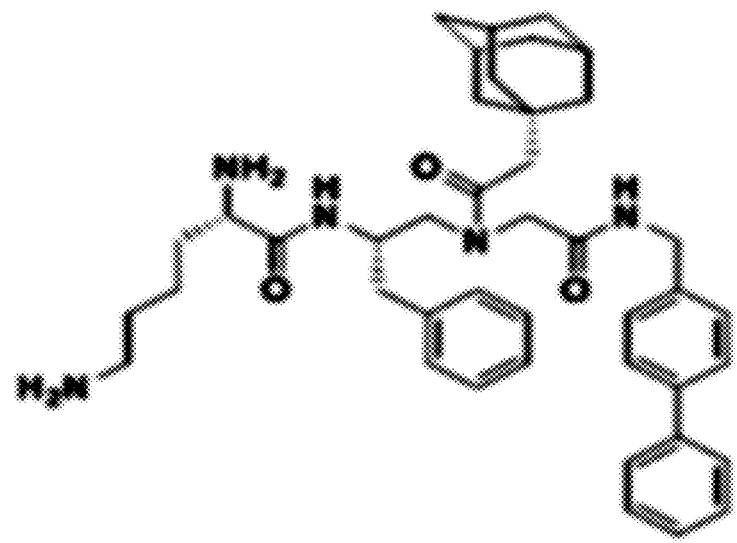
43: 80% (2uM)
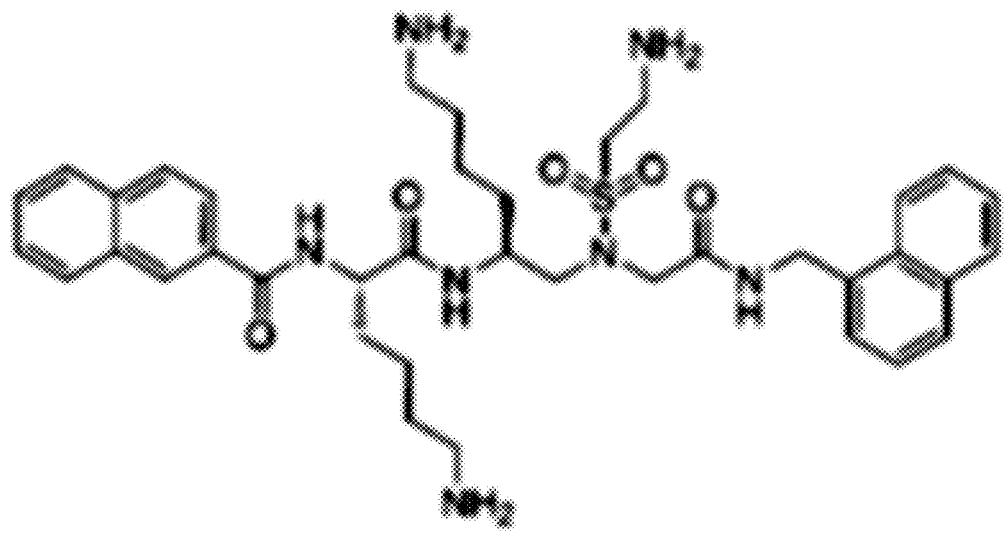
38: 64% (2uM)
FIG. 8 (ctd.)

| Code | Compound | MW | Structure | % Inhibition of PTEN (1uM) |
|---|---|---|---|---|
| 15 | MS-A-54-6 | 612.9 | 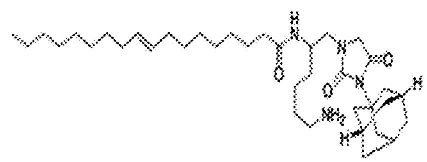 | -47.41084916 |
| 16 | MS-A-60-1 | 474.7 | 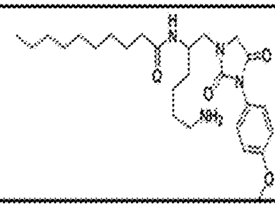 | -12.21735959 |
| 17 | MS-A-60-2 | 502.7 | 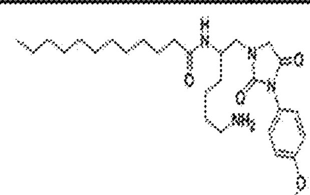 | -13.6761488 |

FIG. 9

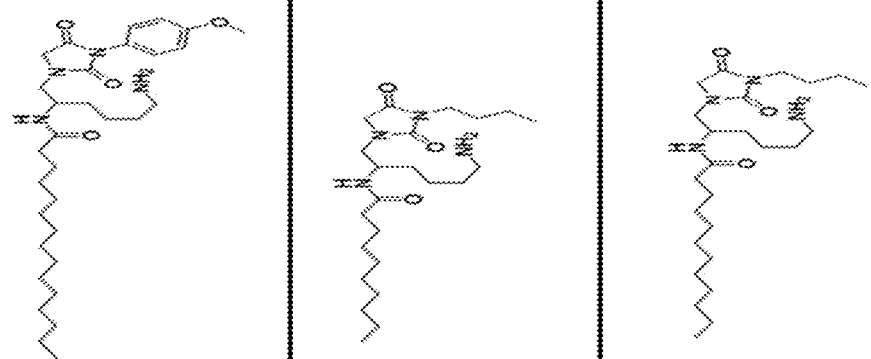
FIG. 9 (ctd.)

| 24 | MS-A-61-5 534.8 | 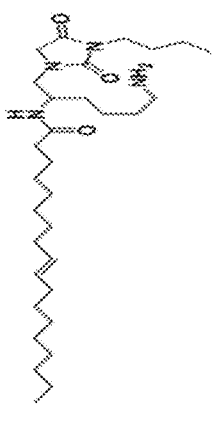 | -10.65719361 |
| 25 | MS-A-63-1 450.7 | 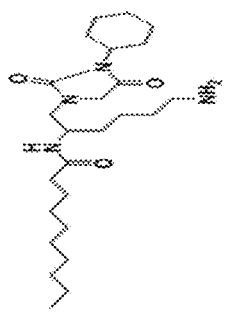 | -15.54174067 |
| 26 | MS-A-63-4 534.8 | 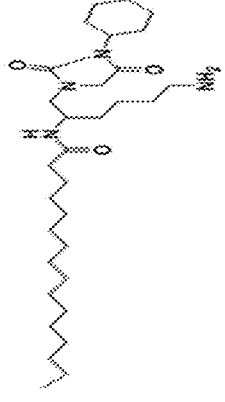 | -37.74422735 |
FIG. 9 (ctd.)

| | | | |
|---|---|---|---|
| 27 | MS-A-63-5 | 560.9 | -65.05328397 |
| 32 | FS-A-136-A2 | 2250 | -23.53463588 |
| 33 | FS-A-136-C | 2649 | -19.98223801 |

FIG. 9 (ctd.)

| | | | |
|---|---|---|---|
| 34 | FS-A-136-D | 2290 | 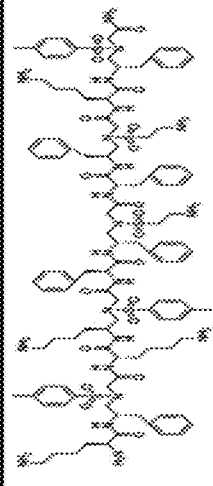 | -14.2095147 |
| 35 | VS-B-87 | 1518 | C78H118N16O11S2 | 40.18650089 |
| 47 | TP-E-106-3 | 740.1 | 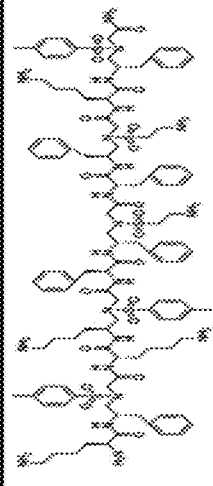 | 46.10492846 |
FIG. 9 (ctd.)

PTEN BINDING COMPOUNDS, FORMULATIONS, AND USES THEREOF

CROSS-REFERENCE TO RELATED APPLICATIONS

This application is a divisional application of co-pending U.S. Utility application Ser. No. 16/265,662, filed on Feb. 1, 2019, entitled "PTEN BINDING COMPOUNDS, FORMULATIONS, AND USES THEREOF," the contents of which are incorporated by reference herein in its entirety, the contents of which is incorporated by reference herein in its entirety.

U.S. Utility application Ser. No. 16/265,662 is a continuation application under 35 U.S.C. § 111(a) of Patent Cooperation Treaty Application No.: PCT/US2018/000049, filed on Feb. 16, 2018, entitled "PTEN BINDING COMPOUNDS, FORMULATIONS, AND USES THEREOF," the contents of which are incorporated by reference herein in its entirety.

Patent Cooperation Treaty Application No.: PCT/US2018/000049 claims the benefit of and priority to U.S. Provisional Patent Application No. 62/460,324, filed on Feb. 17, 2017, entitled "PTEN BINDING COMPOUNDS, FORMULATIONS, AND USES THEREOF," the contents of which are incorporated by reference herein in its entirety.

BACKGROUND

Phosphatase and tensin homolog (PTEN) is a protein and an enzyme. PTEN negatively regulates levels of phosphatidylinositol-3,4,5-triphosphate in cells and can negatively regulate the Akt/PKB signaling pathway. Dysfunction of PTEN has been implicated in the development of cancers. Given the regulatory role PTEN plays there is a need for the development of compounds capable of binding PTEN to provide therapies where alteration in PTEN activity would be beneficial for therapeutic purposes in various PTEN-related diseases.

SUMMARY

Described herein in some aspects are compounds that can have a structure according to Formula 1

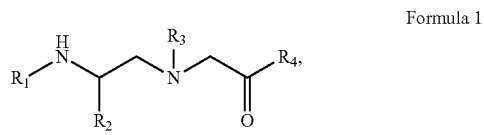

Formula 1 where $R_1$ can be H,

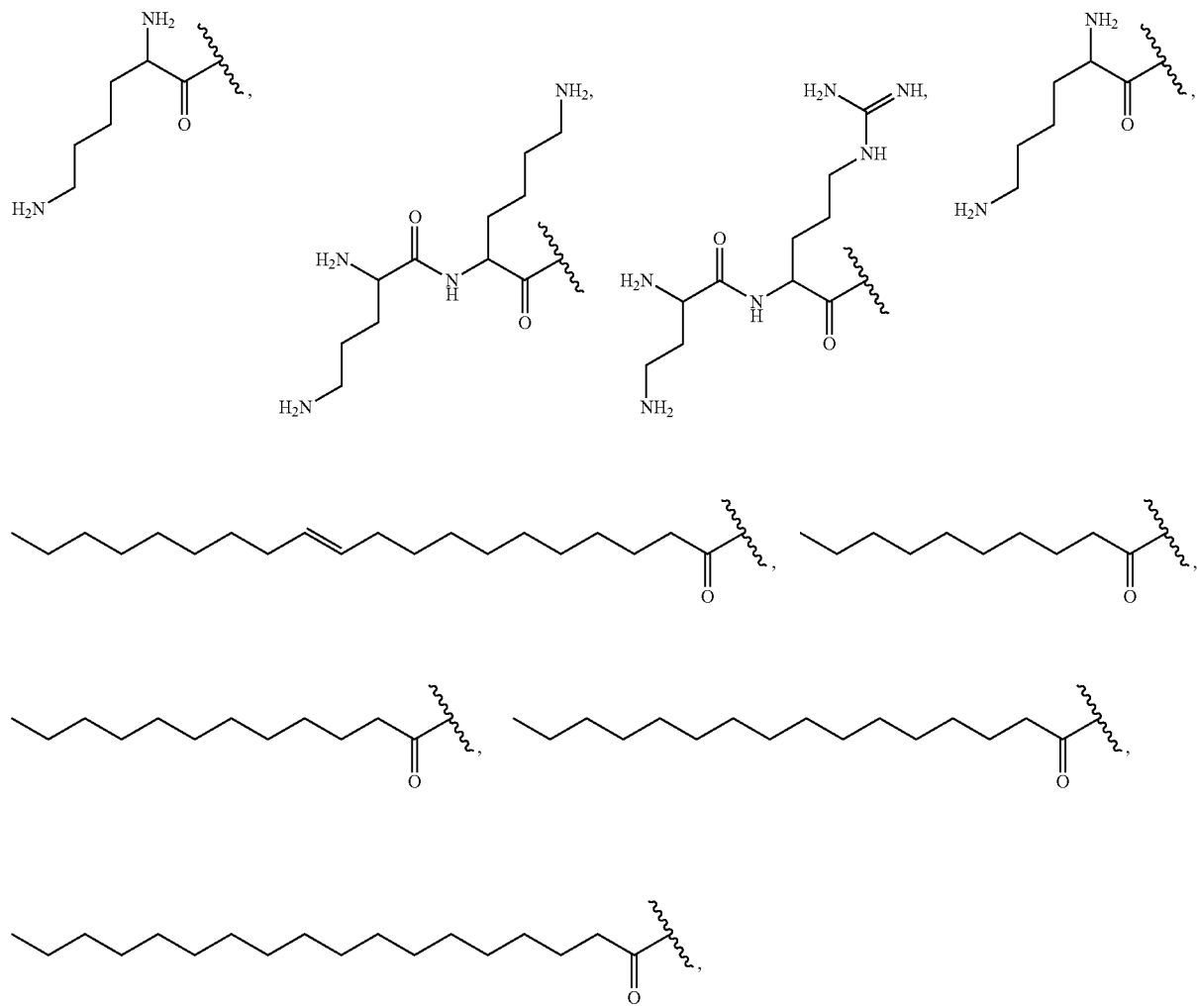

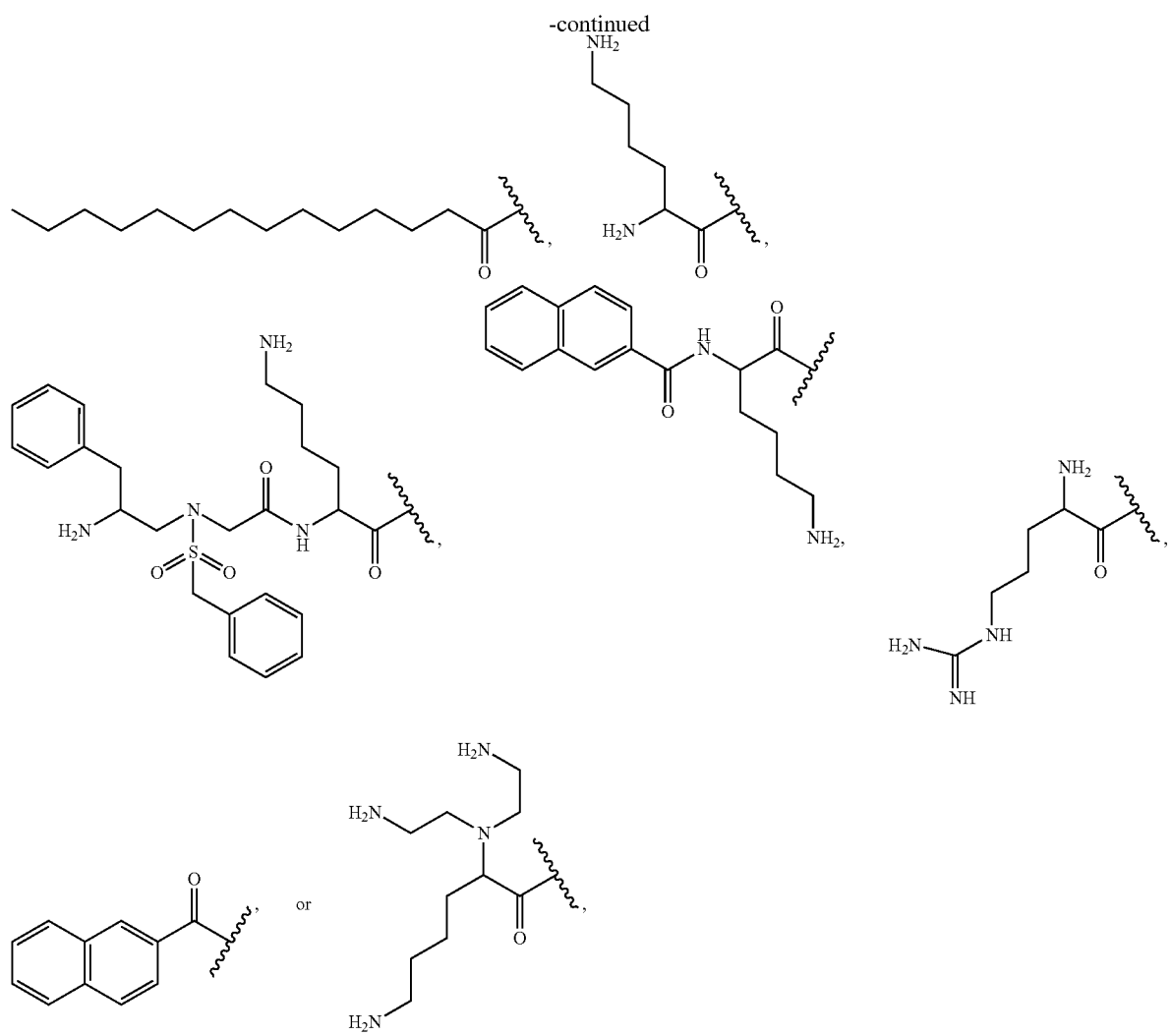
where R₂ can be
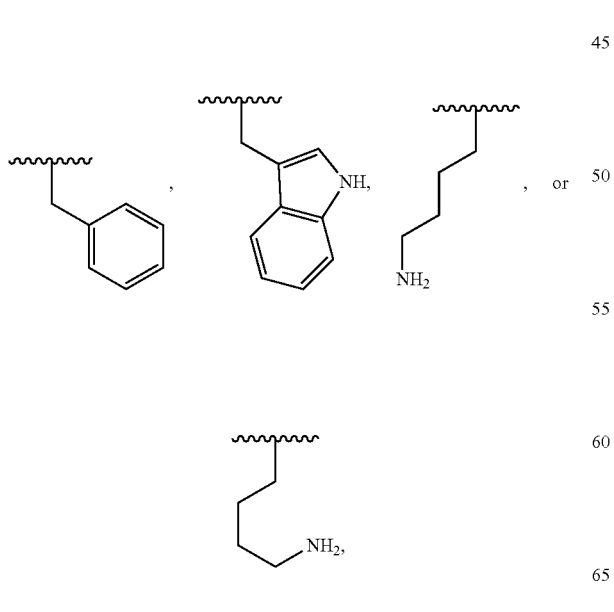
where R₃ can be
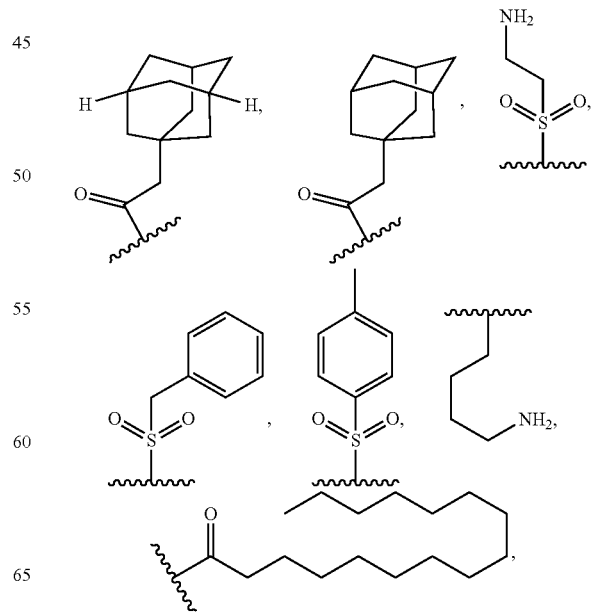

5
-continued
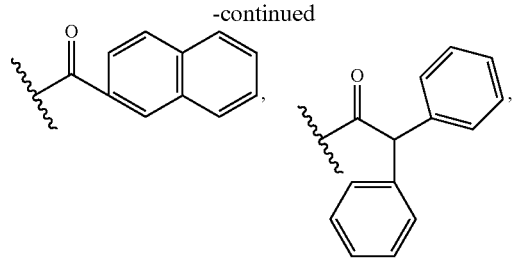
6
-continued
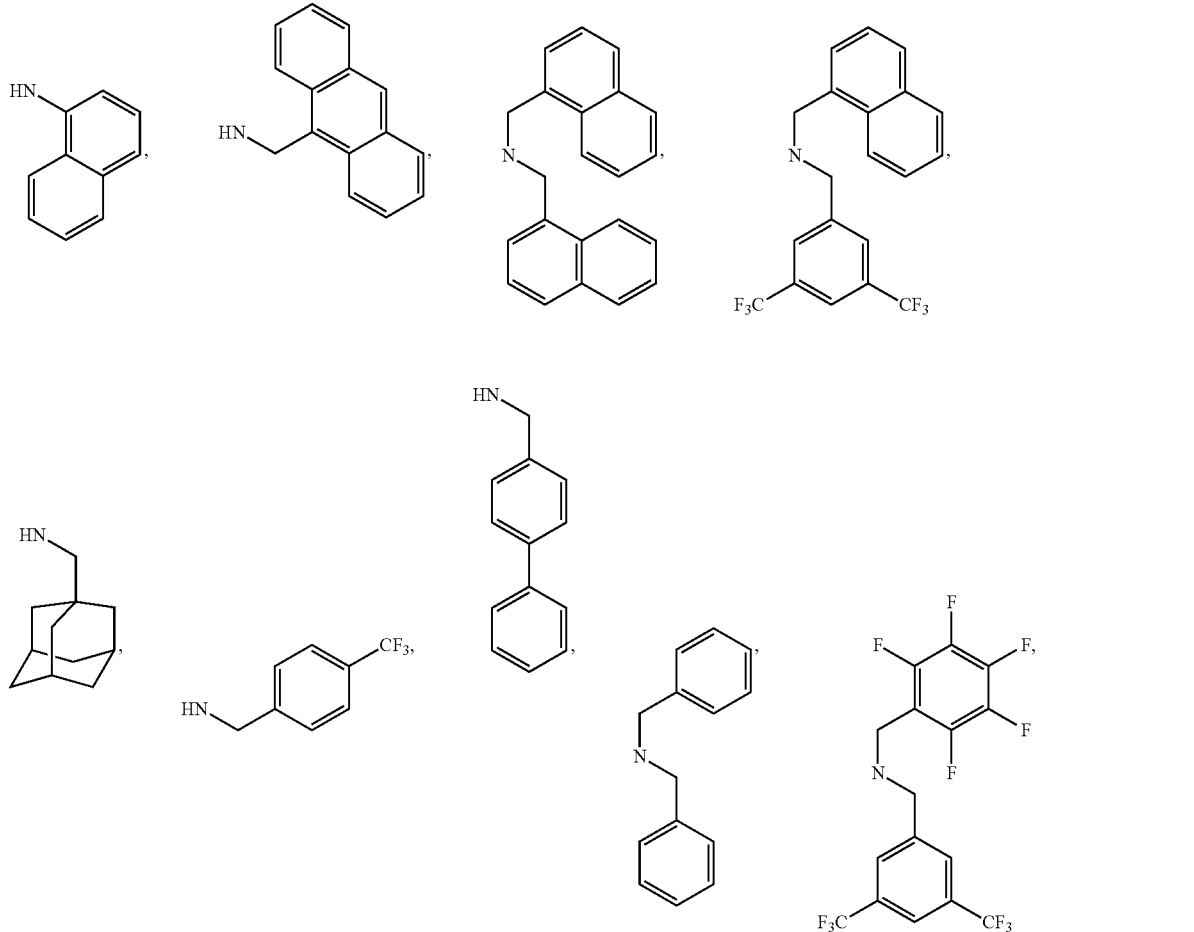
where R₄ can be
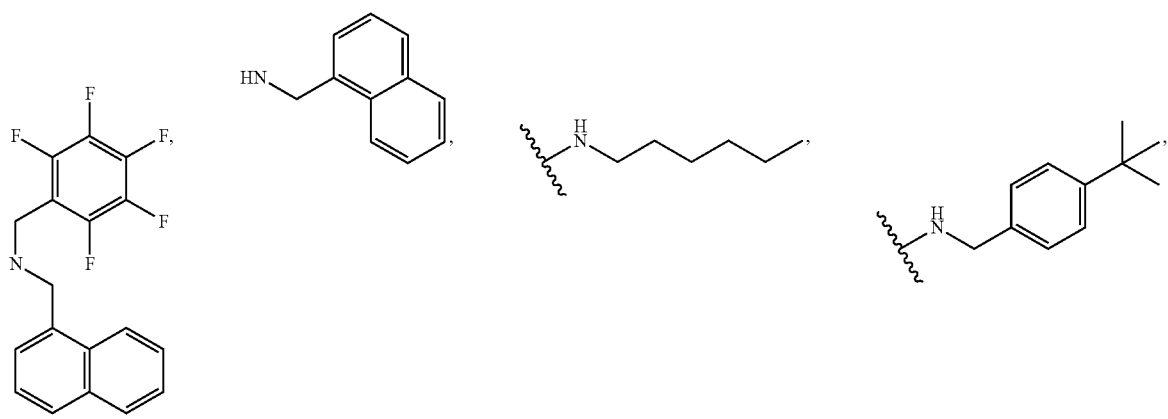

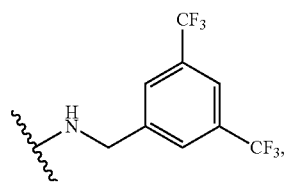
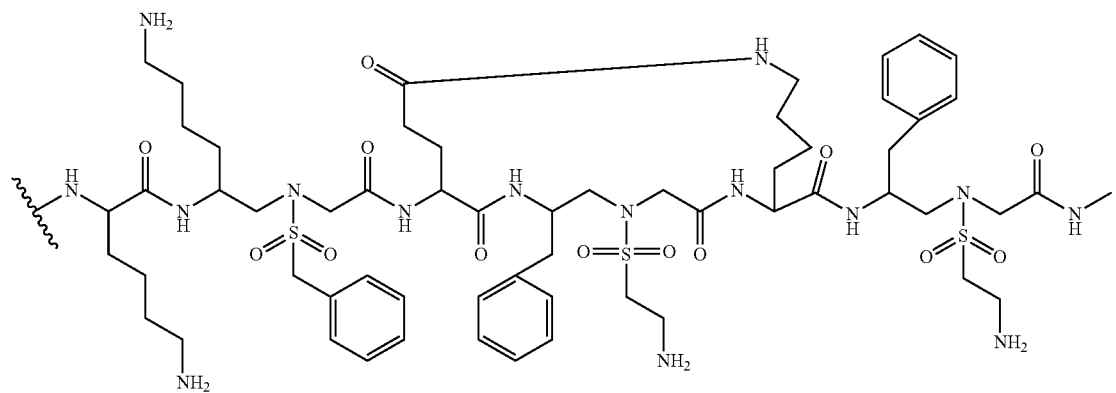
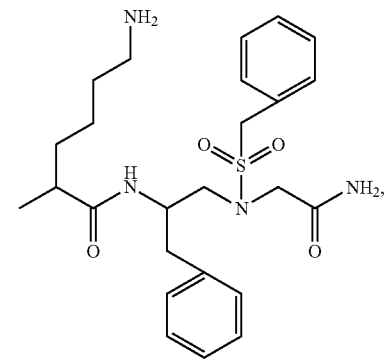
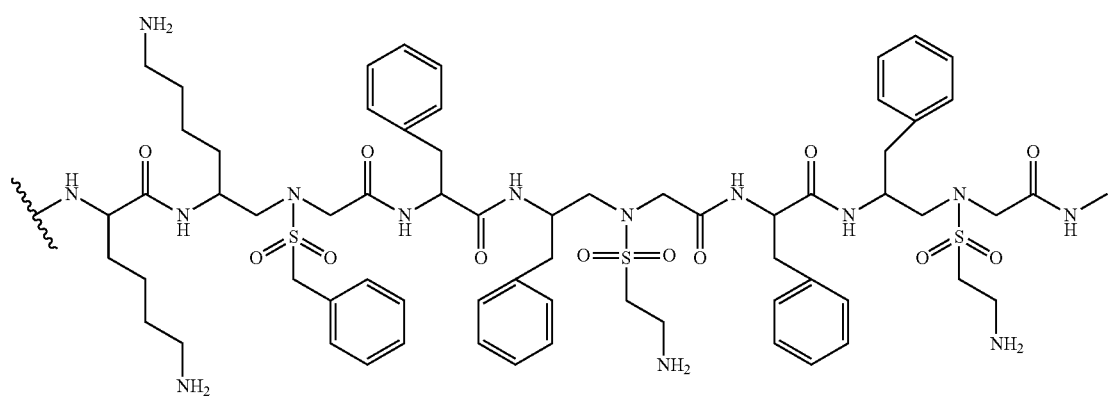
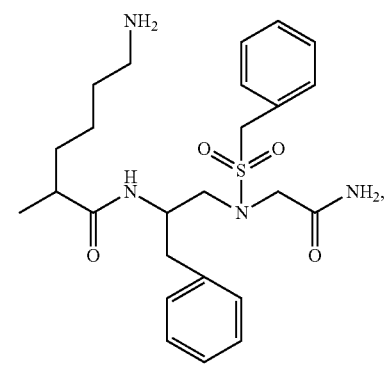

9
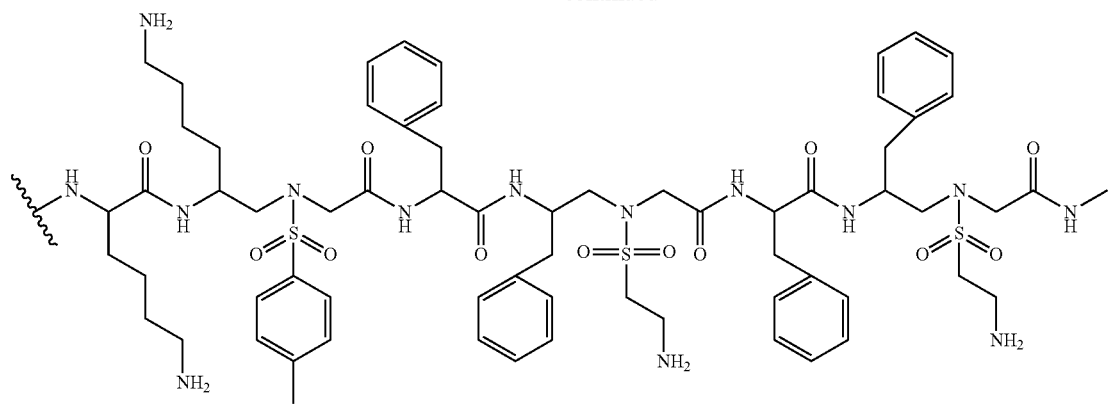
10
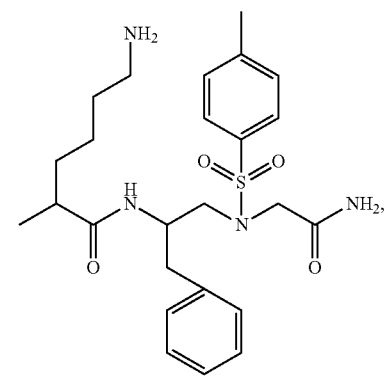
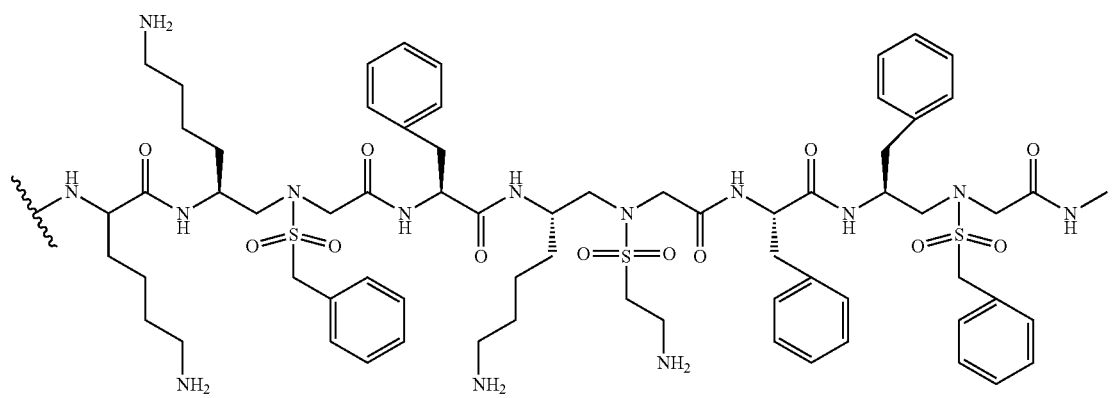
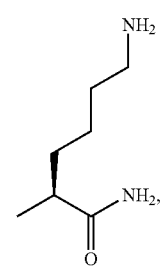

11
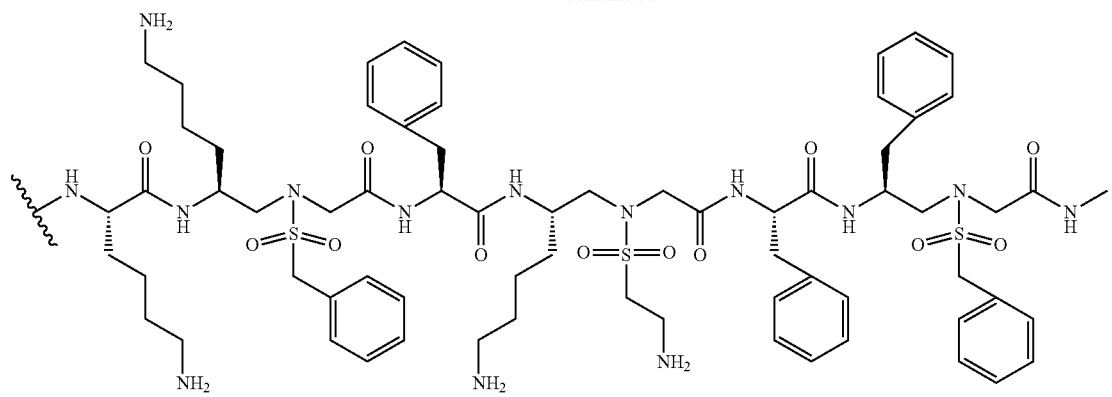
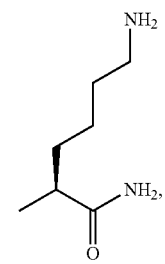
12
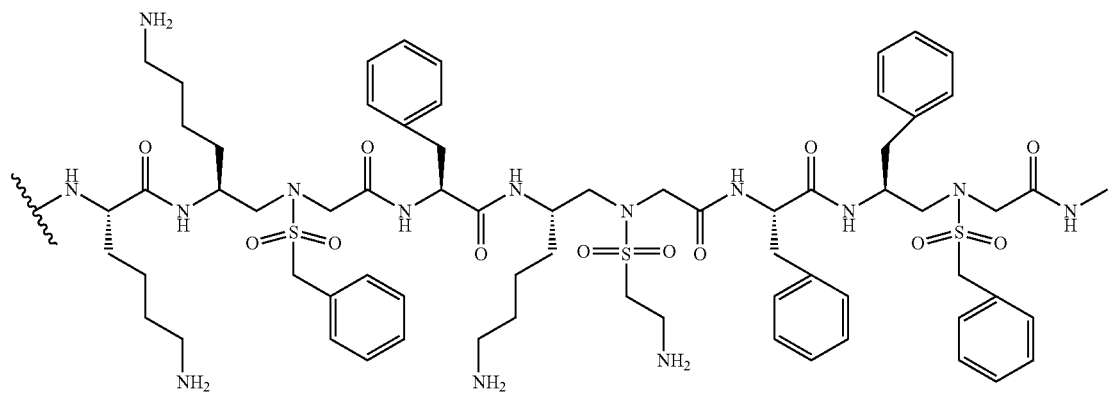
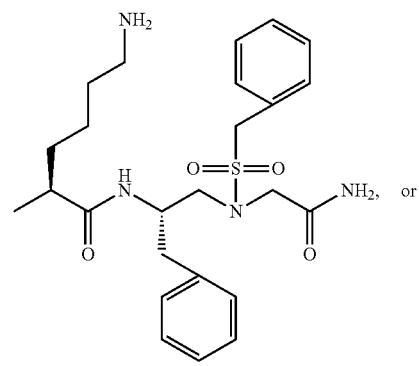

-continued

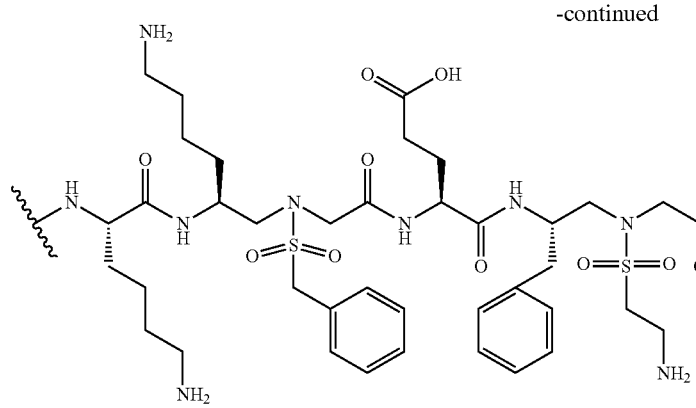
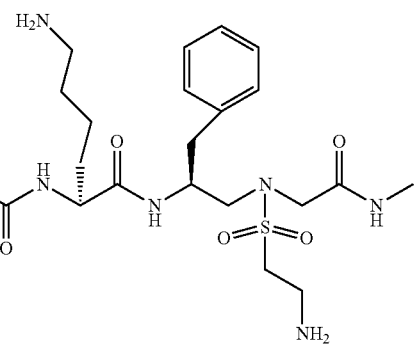

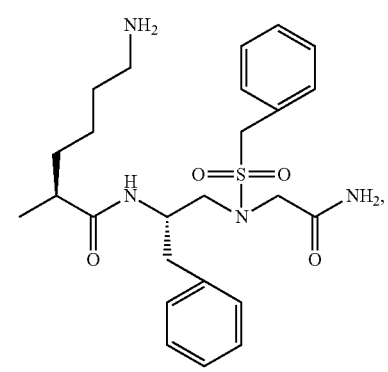

In some aspects, the compound of Formula I can be compound 15, 16, 17, 19, 20, 21, 24, 25, 26, 27, 32, 33, 34, 35, or 47. In some aspects, the compound(s) can be effective to decrease the activity of PTEN. In some aspects, the compound can be effective to decrease the activity of PTEN by 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, or 200 percent or more. In some aspects the compound can be compound 5, 8, 9, 10, 11, 12, 13, 14, 38, 39, 40, or 43. In some aspects, the compound can be effective to increase the activity of PTEN. In some aspects, the compound can be effective to increase the activity of PTEN by 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, or 200 percent or more.

Also described herein are pharmaceutical formulations that can include a compound having a structure according to Formula I or where $R_3$ and $R_4$ can together form

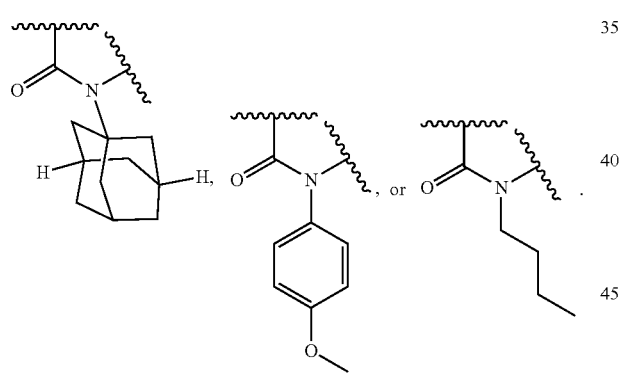

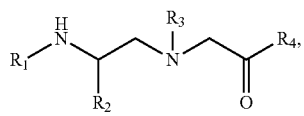

where $R_1$ can be H,

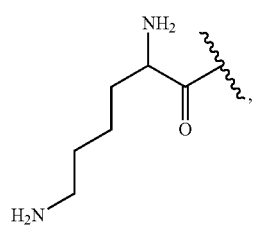

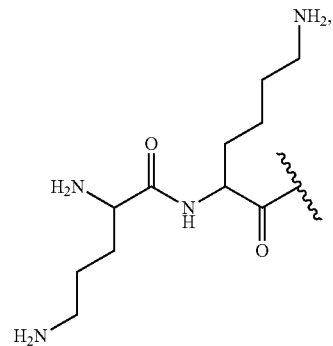

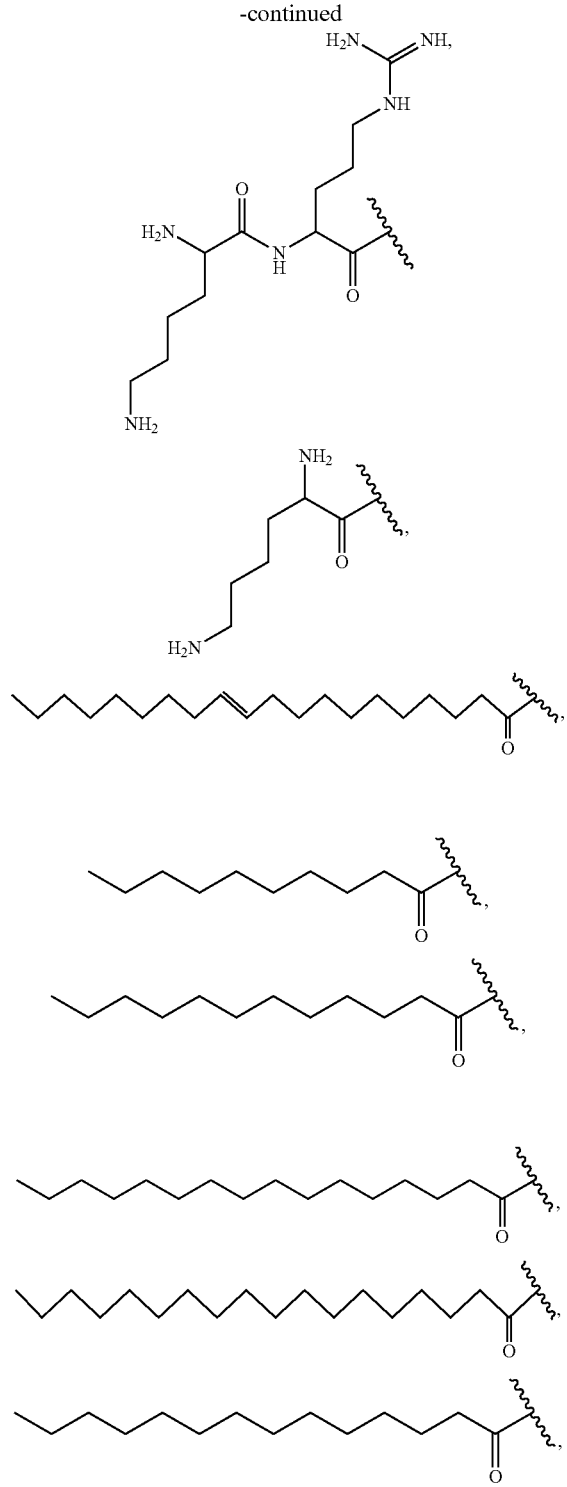
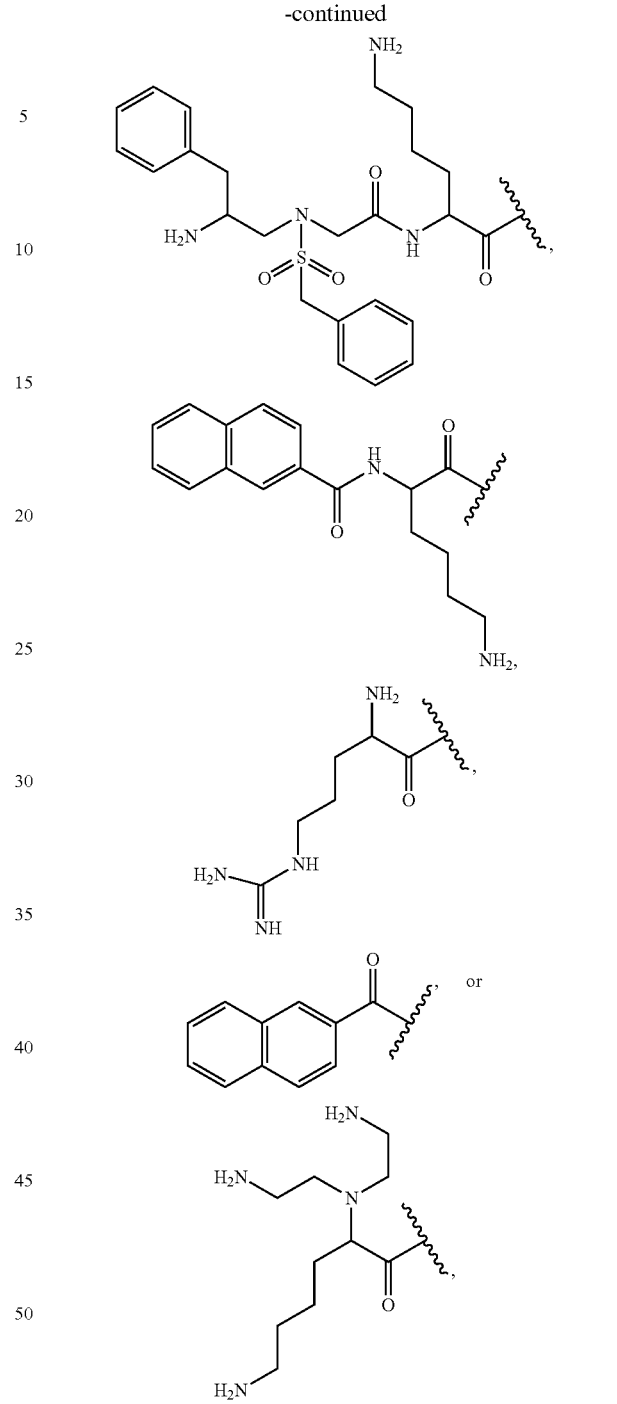
where $R_2$ can be
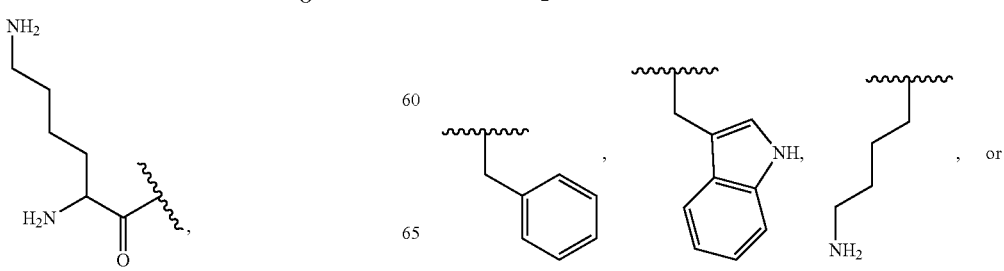

-continued
17
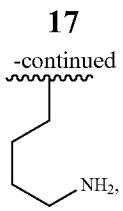
where R₃ can be
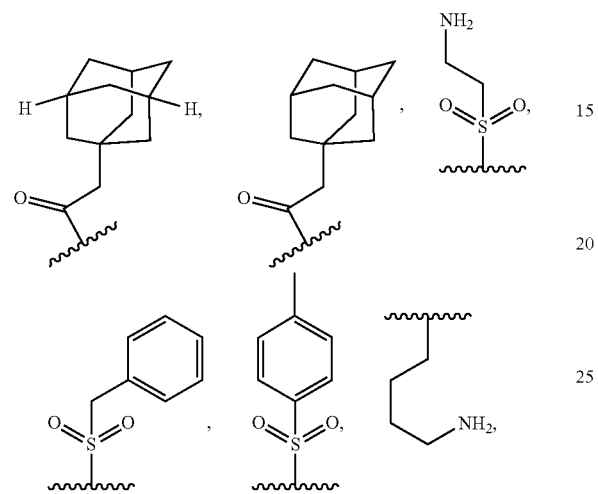
18
-continued
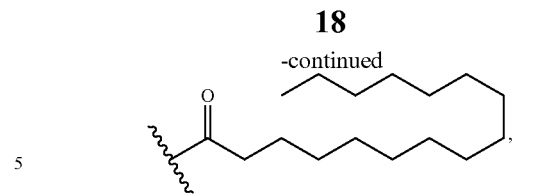
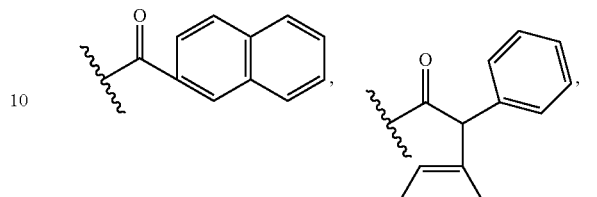
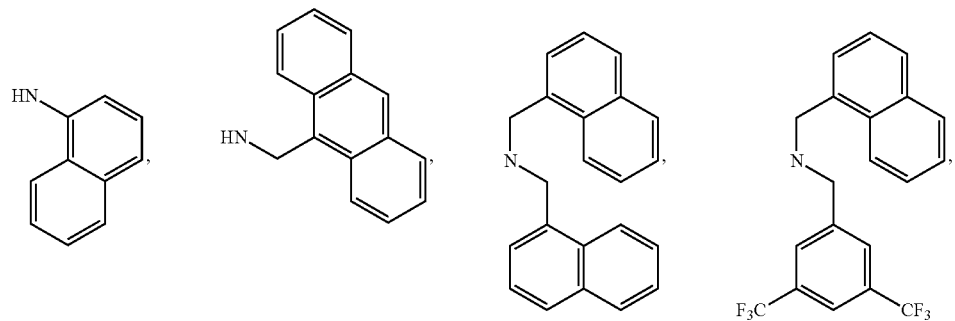
where R₄ can be
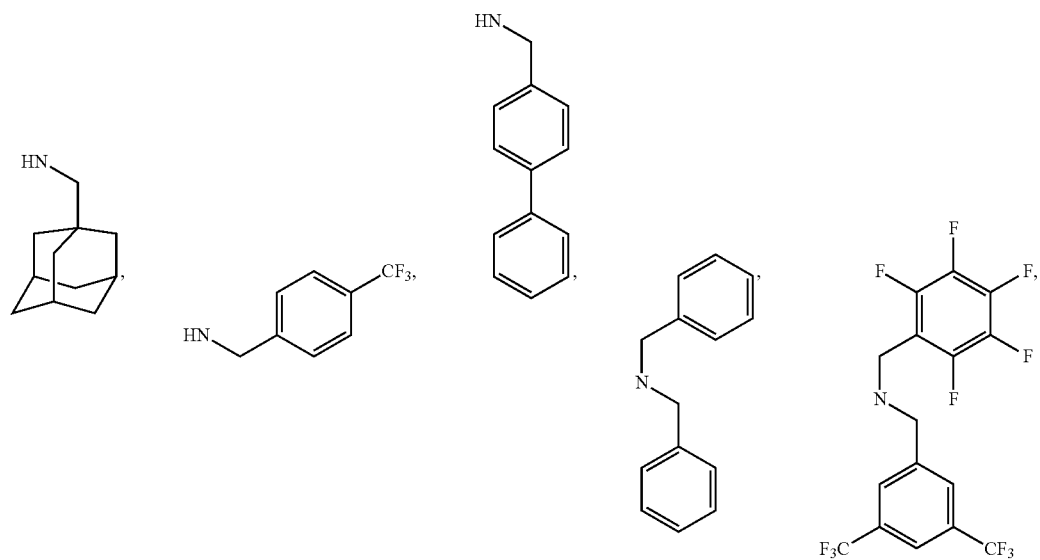

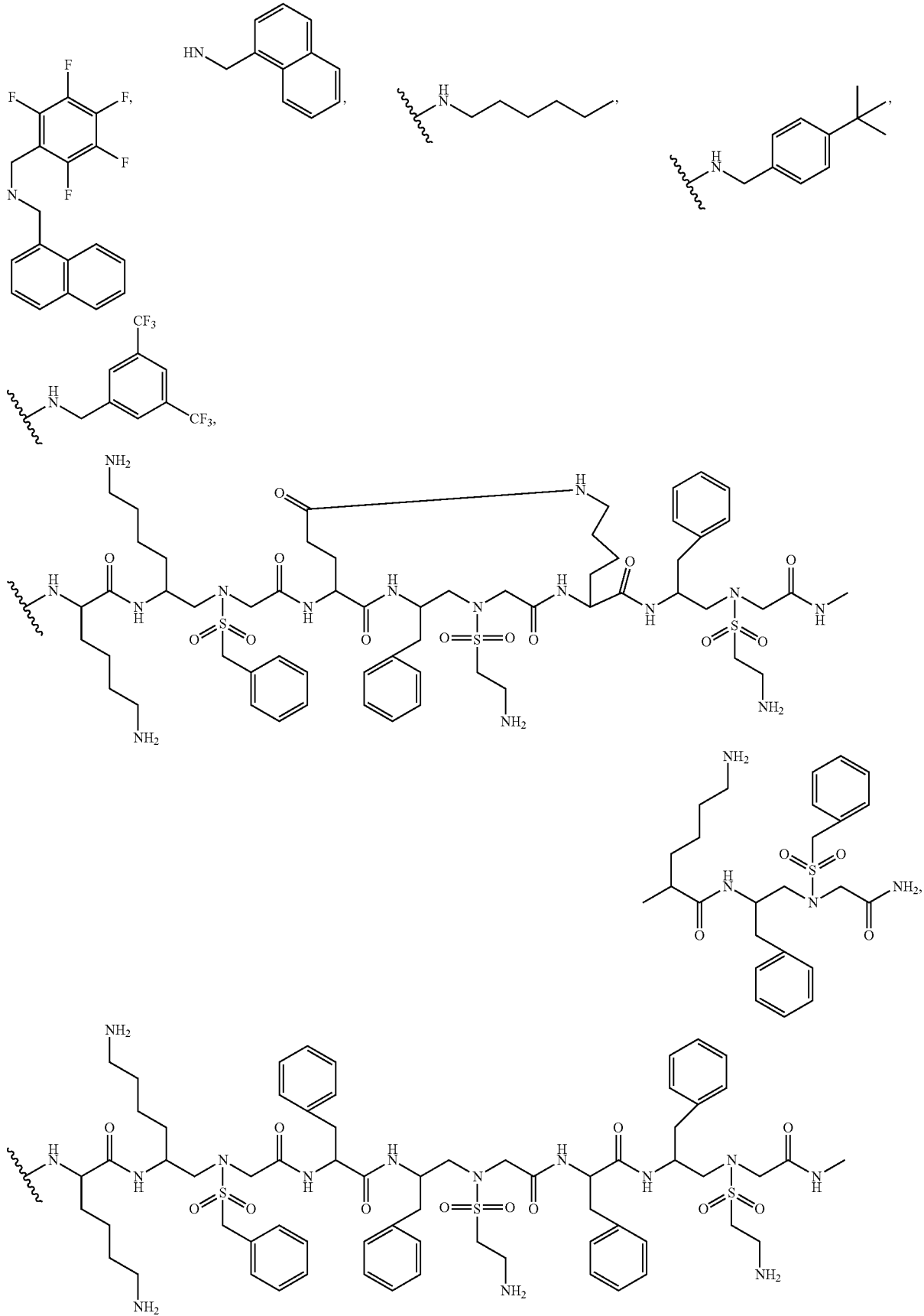

-continued
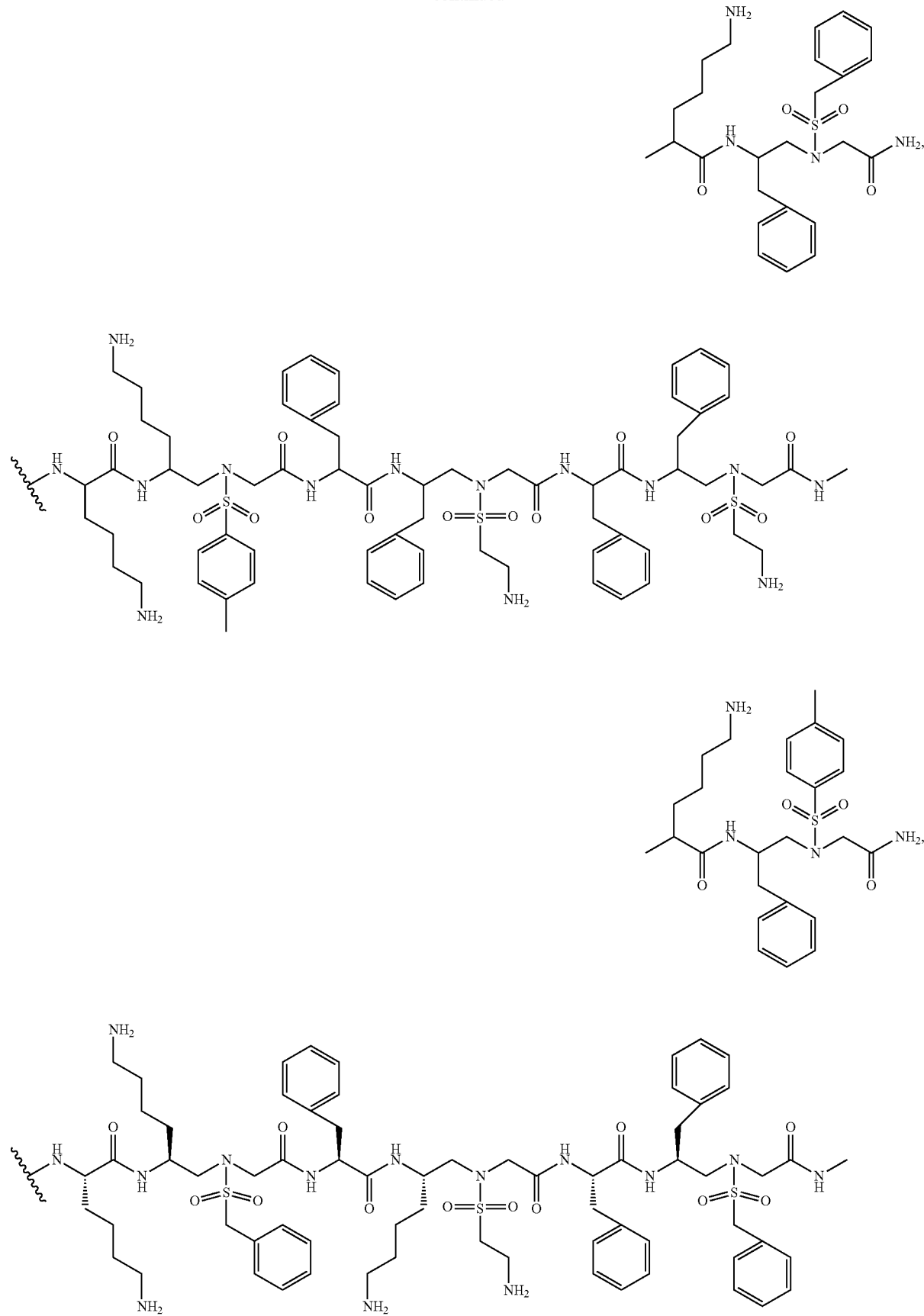

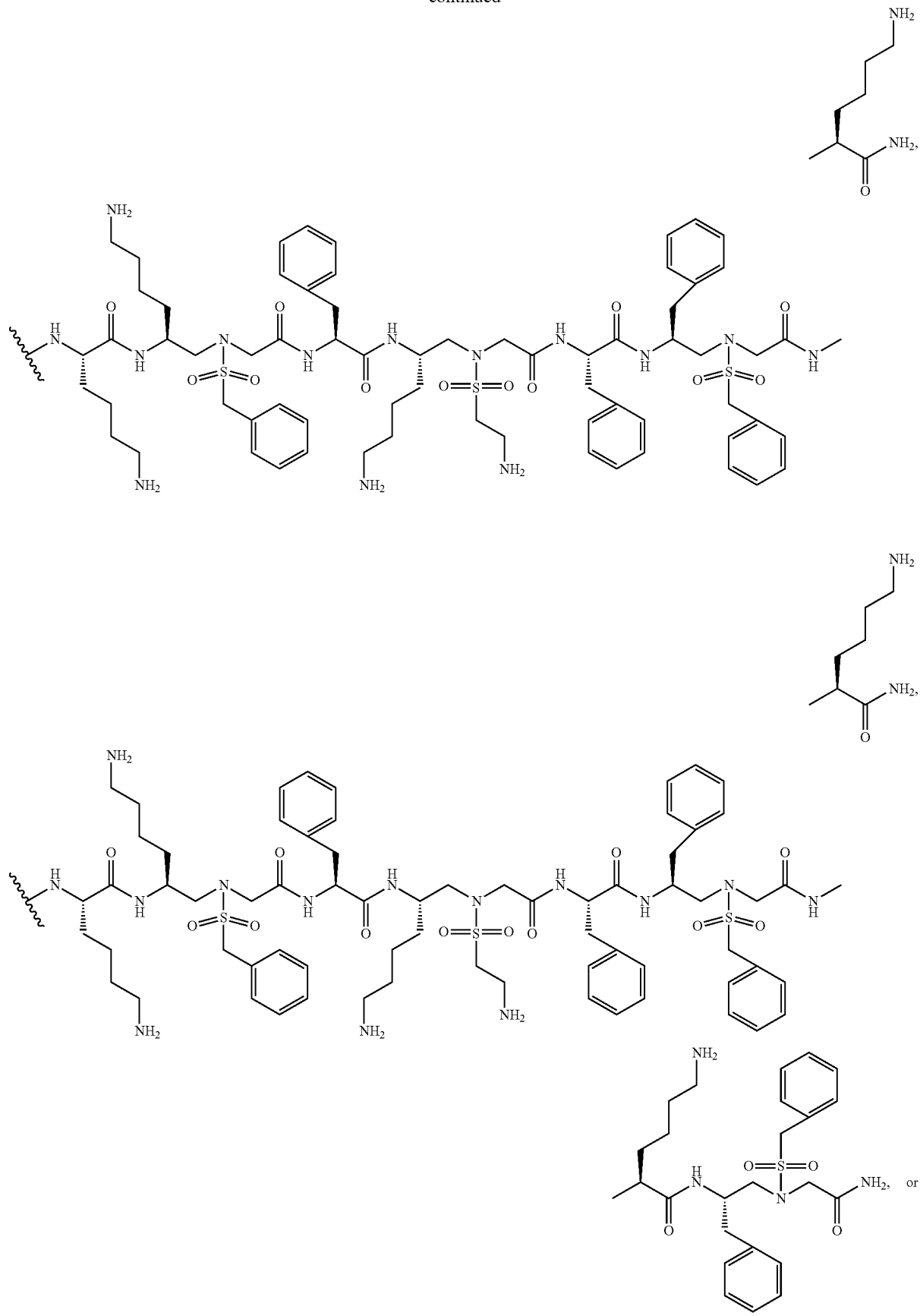

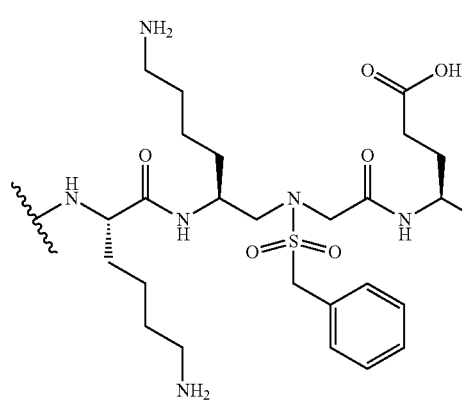

-continued

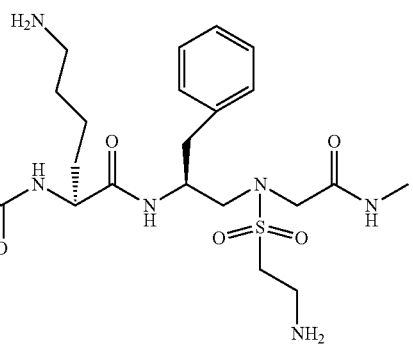

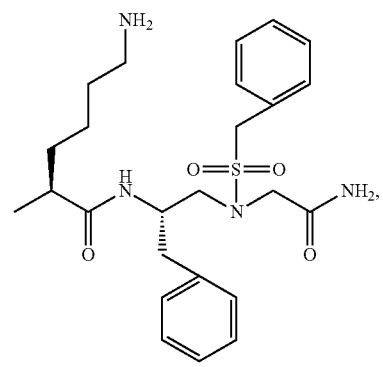

or where R₃ and R₄ can together form

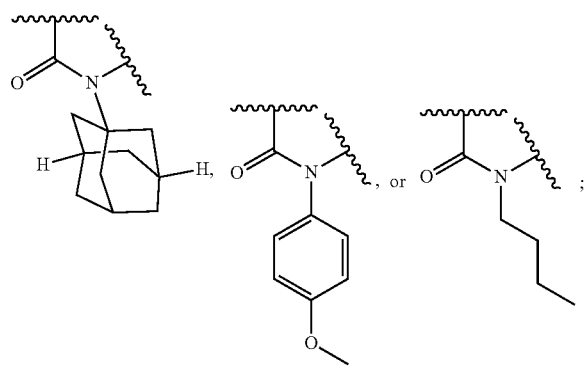

and a pharmaceutically acceptable carrier. In some aspects, the pharmaceutical formulation can include any one or more of compounds 1-51. In some aspects, the compound(s) can be effective to decrease the activity of PTEN. In some aspects, the compound can be effective to decrease the activity of PTEN by 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, or 200 percent or more. In some aspects the compound can be compound 5, 8, 9, 10, 11, 12, 13, 14, 38, 39, 40, or 43. In some aspects, the compound can be effective to increase the activity of PTEN. In some aspects, the compound can be effective to increase the activity of PTEN by 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, or 200 percent or more.

Also described herein are methods that can include the step of contacting PTEN with an amount of one or more compounds and/or pharmaceutical formulations described herein. The step of contacting can be performed in vitro. The step of contacting can be performed in vivo. In some aspects, the method can further include the step of administering the amount of one or more compounds and/or pharmaceutical formulations to a subject, wherein step of administering can occur prior to the step of contacting. The subject can have a disease with a pathology that involves PTEN. In some aspects, the subject can have a cancer or a PTEN-opathy.

Also described herein are methods that can include the step of administering one or more compounds and/or pharmaceutical formulations to a subject. In some aspects the subject can have a cancer or a PTEN-opathy.

Any one of the compounds described herein (e.g. those that are according to Formula I, including but not limited to compounds 1-51) can be for use as a medicament for treating a cancer and/or a PTEN-opathy. Any one of the compounds described herein (e.g. those that are according to Formula I, including but not limited to compounds 1-51) can be for use in the manufacture of a medicament for treating a cancer and/or a PTEN-opathy. Any one of the compounds or pharmaceutical formulations described herein can be for use in treating a cancer or a PTEN-opathy.

BRIEF DESCRIPTION OF THE DRAWINGS

Further aspects of the present disclosure will be readily appreciated upon review of the detailed description of its various embodiments, described below, when taken in conjunction with the accompanying drawings.

(FIG. 1A) 51 γ-AAPeptides were screened for changes in PTEN lipid phosphatase activity at 1 μM using Malachite Green assay, n=4. Values reported as mean±SE. (FIG. 1B). 11 select γ-AAPeptides shown to increase PTEN lipid phosphatase activity at 1 μM were titrated and measured for changes in PTEN lipid phosphatase activity using Malachite Green assay, n=4. Values reported as mean±SE.

(FIG. 2A) Immunoblot analysis shows a significant decrease in expression of activated PI3K/AKT/S6K pathway intermediates, p-AKT (Ser473) and p-P70 S6K (Thr389), in A549 cells treated with 40 µM γ-AA Peptide #43 for 6 hours. Densitometry graphs shown to the right of blots, n=3 (*p value ≤1.05). (FIG. 2B) Immunoblot analysis shows a significant decrease in expression of activated PI3K/AKT/S6K pathway intermediates, p-AKT (Ser473) and p-P70 S6K (Thr389), in A549 cells treated with 40 µM γ-AA Peptide #9 for 6 hours. Densitometry graphs shown to the right of blot images in FIGS. 2A and 2B, n=3 (*p value ≤1.05).

(FIG. 3A) Dose-dependent inhibition of A549 cell proliferation was observed in A549 cells treated for 24 hours with indicated concentration of γ-AA Peptide #43. Cells were plated at 9000 cells/well, n=6 (*p value≤1.05). (FIG. 3B) Dose-dependent inhibition of A549 cell proliferation was observed in A549 cells treated for 24 hours with indicated concentration of γ-AA Peptide #9. Cells were plated at 9000 cells/well, n=6 (*p value ≤1.05). (FIG. 3C) Continuous impedance sensing measurements reveal a decrease in wound closure efficiency for A549 cells treated with 30 µM γ-AA Peptide #43, 12 hours prior to wounding, as compared to control cells, n=3. (FIG. 3D) Continuous impedance sensing measurements reveal a decrease in wound closure efficiency for A549 cells treated with 20 µM γ-AA Peptide #9, 12 hours prior to wounding, as compared to control cells, n=3. (FIG. 3E) Cell cycle analysis of A549 cells treated for 24 hours with 40 µM γ-AA Peptide #43 shows an increase in G1 cell population with a decreased S phase and G2 phase cell population, n=3 (*p value ≤1.05). (FIG. 3F) Cell cycle analysis of A549 cells treated for 24 hours with 20 µM γ-AA Peptide #9 shows an increase in G1 cell population, a decreased S phase population and an increase in G2 phase cell population, n=3 (*p value ≤1.05).

Figure 5:
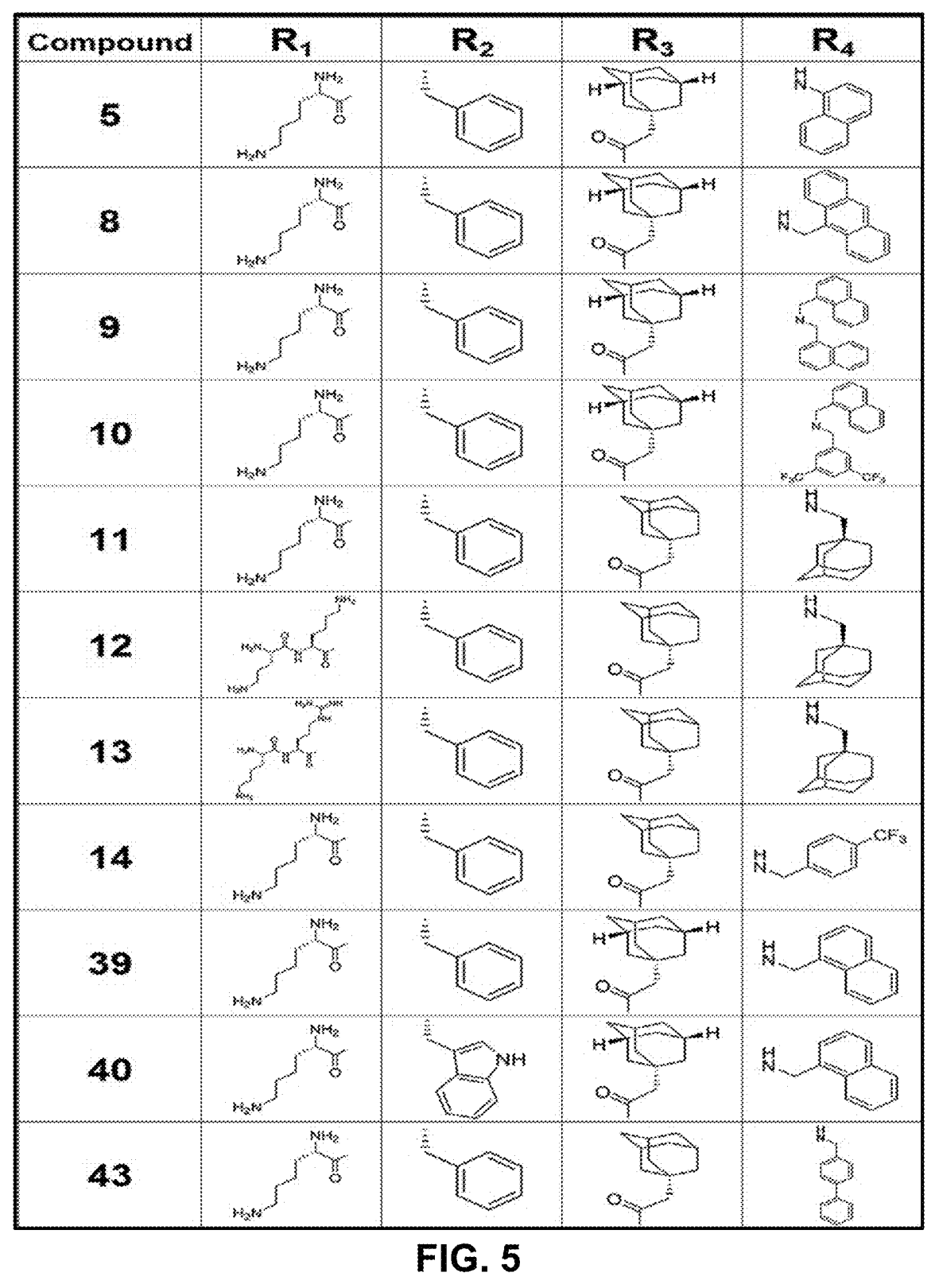

FIG. 5 shows a table demonstrating example γ-AAPeptide Side Chain Structures. FIG. 5 provides a visual representation of the 4 R-group side chains for each γ-AA Peptide. R-groups are added to the N-acylated-N-aminoethyl backbone, as previously described.

FIG. 6 shows example small molecule compounds that are capable of enhancing PTEN activity.

FIG. 9 shows example small molecule compounds that are capable of inhibiting PTEN activity.

DETAILED DESCRIPTION

Figure 1A:
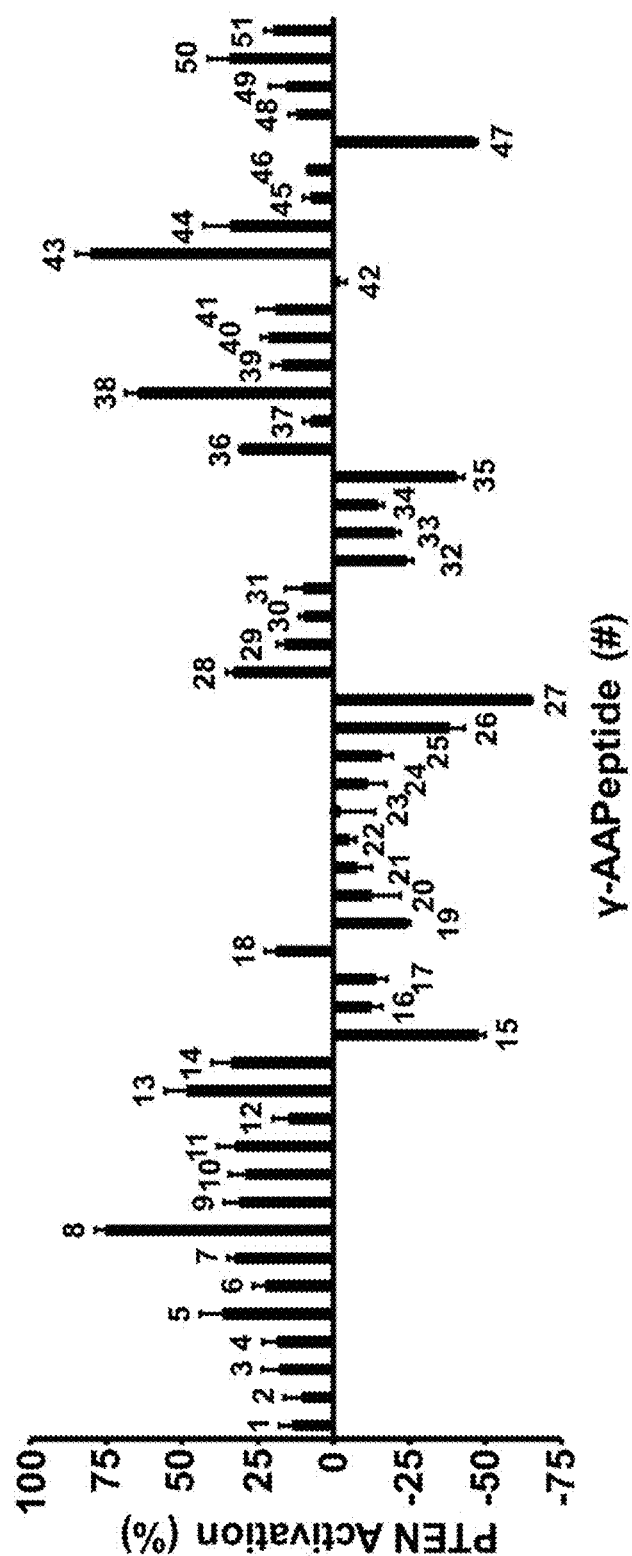
FIGS. 1A-1B show results from a screening of γ-AA peptides.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, genomics, proteomics, microbiology, nanotechnology, chemistry, organic chemistry, biochemistry, and the like, which are within the skill of the art. Such techniques are explained fully in the literature.

Definitions

As used herein, As used herein, "about," "approximately," and the like, when used in connection with a numerical variable, can refer to the value of the variable and to all values of the variable that are within the experimental error (e.g., within the 95% confidence interval for the mean) or within +/−10% of the indicated value, whichever is greater.

As used herein, "active agent" or "active ingredient" can refer to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "active derivative" and the like can refer to a compound that is capable of binding PTEN as provided herein. The term "active derivative" and the like can also refer to a compound or analogue thereof provided herein that can be effective at altering (increasing or decreasing) the activity and/or abundance of PTEN. The term "active derivative" can also refer to a compound or analogue thereof that can be effective at treating a disease or symptom thereof whose pathology involves PTEN. Assays for testing the ability of an active derivative to perform in this fashion are known to those of ordinary skill in the art and provided herein. The assays can include, but are not limited to, in vitro and in vivo assays.

As used herein, "additive effect" can refer to an effect arising between two or more molecules, compounds, substances, factors, or compositions that is equal to or the same as the sum of their individual effects.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques.

As used herein, "agent" can refer to any substance, compound, molecule, and the like, which can be biologically active or otherwise can induce a biological and/or physiological effect on a subject to which it is administered to. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein, "attached," "attachment" and the like can refer to the formation of a covalent or non-covalent association (e.g. a bond) between two or more molecules or conjugation of two or more molecules. As used herein, "attached," "attachment" and the like can refer to direct association of two or more molecules together with no intermediate molecules between those that are attached together or to the indirect attachment of two or more molecules together that is mediated via one or more linkers. Where the association is non-covalent, this can encompass charge interactions, affinity interactions, metal coordination, physical adsorption, host-guest interactions, hydrophobic interactions, TT stacking interactions, hydrogen bonding interactions, van der Waals interactions, magnetic interactions, electrostatic interactions, dipole-dipole interactions, and/or combinations thereof. Where the association is covalent, this can encompass bonds where a pair of electrons is shared between one or more atoms in each molecule involved.

As used interchangeably herein, "biocompatible," "biocompatibility," and "biologically compatible" can refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments, a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

As used herein, "a compound of formula (1), (2), (3), (4), (5), (6), (6a), (6b) (7), (8), (9), (10), (11), (12), (13), (14), (A), (B), (C), (D), and so forth and so on," or "a compound having a structure according to formula (1), (2), (3), (4), (5), (6), (6a), (6b) (7), (8), (9), (10), (11), (12), (13), (14), (A), (B), (C), (D), etc.," compound (1), (2), (3), (4), (5), (6), (6a), (6b) (7), (8), (9), (10), (11), (12), (13), (14), (A), (B), (C), (D), and so forth and so on," or a "compound" can include all or any sub-group of solvates, complexes, polymorphs, derivatives thereof (including but not limited to, radiolabeled derivatives (including deuterated derivatives where one or more H are replaced by D)), tautomers, stereoisomers, and optical isomers of the compound of the formulas listed above and salts thereof.

As used herein, "chemotherapeutic agent" or "chemotherapeutic" can refer to a therapeutic agent utilized to prevent or treat cancer and any other disease that is associated with altered PI3K/AKTPTEN pathway, PTEN activity and/or PTEN function.

As used herein, "control" can refer to an alternative subject or sample used in an experiment for comparison purposes and included to minimize or distinguish the effect of variables other than an independent variable. A control can be positive or negative. One of ordinary skill in the art will appreciate what are appropriate controls for a given context.

As used herein, "concentrated" can refer to an amount of a molecule, compound, or composition, including, but not limited to, a chemical compound, polynucleotide, peptide, polypeptide, protein, antibody, or fragments thereof, that indicates that the sample is distinguishable from its naturally occurring counterpart in that the concentration or number of molecules per volume is greater than that of its naturally occurring counterpart.

As used herein, "derivative" can refer to substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfonamides, benzoxycarboamides, t-butyloxycarboam ides, thiourethane-type derivatives, trifluoroacetylamides, chloroacetylamides, or formamides. Derivatives include compounds in which carboxyl groups in the parent compound have been derivatized to form salts, methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imines, thiones, sulfones, tertiary amides, and sulfides. "Derivatives" also includes extensions of the replacement of the cyclopentane ring with saturated or unsaturated cyclohexane or other more complex, e.g., nitrogen-containing rings, and extensions of these rings with various side groups.

As used herein, "diluted" can refer to an amount of a molecule, compound, or composition including but not limited to, a chemical compound, polynucleotide, peptide, polypeptide, protein, antibody, or fragments thereof, that indicates that the sample is distinguishable from its naturally occurring counterpart in that the concentration or number of molecules per volume is less than that of its naturally occurring counterpart.

As used herein, "dose," "unit dose," or "dosage" can refer to physically discrete units suitable for use in a subject, each unit containing a predetermined quantity of a compound as provided herein and/or a pharmaceutical formulation thereof calculated to produce the desired response or responses in association with its administration.

As used herein, "effective amount" can refer to an amount sufficient to effect beneficial or desired results. An effective amount can be administered in one or more administrations, applications, or dosages. "Effective amount" can refer to an amount of a compound, derivative, and/or formulation thereof provided herein that can treat and/or prevent a disease or symptom thereof whose pathology involves PTEN. Some diseases include, but are not limited to, all cancers that have compromised PTEN activity or function and all those cancers wherein there is hyperactivity of the PI3K/AKT/mTOR/S6K signaling pathway. An extensive list of all PTEN-related cancers which are included within the scope of this disclosure can be found at the National Institute of Health website. The main malignancies include, but are not limited to, cancers of the breast, prostate, lung, endometrium, head and neck squamous cell carcinoma (HNSCC), ovary, colon, colo-rectal, lymphoma, mesothelioma, salivary gland, testicular cancers, cancers of the thyroid, skin, stomach, soft tissue sarcoma, cancers of the brain including glioblastomas and astrocytomas, aggressive form of skin cancers such as melanomas and head and neck squamous cell carcinomas. More extensive information on PTEN-related cancers can be found National Institute of Health website. The compounds and formulations thereof described herein can be effective to treat and/or prevent other PTEN-related diseases including all the "PTEN-Opathies" (PTEN hamartoma tumor syndromes (PHTS), Bannayan-Riley-Ruvalcaba syndrome (BRRS), Juvenile polyposis of infancy (JPI), Cowden's syndrome, Hemangiomas, Immune dysregulation, PTEN-related Proteus syndrome (PS), Lhermitte-Duclos disease (LDD), Autism and Autism/pervasive developmental disorder and macrocephaly, Alzheimer's disease, Parkinsonism and metabolic disorders/obesity), which are associated with aberrant PTEN function. (Am J Med Genet C Semin Med Genet. 2013 Apr. 9). The compounds and formulations thereof described herein can be effective to modulate PTEN activity. The compounds and formulations thereof described herein can also be effective to treat, prevent, and/or modulate PTEN activity in TBI (Traumatic Brain injury), neural ischemia, amyotrophic lateral sclerosis (ALS), and other neurodegenerative diseases. The compounds and formulations thereof described herein can also be effective to promote regrowth of the corticospinal tract, including, but not limited to, the axons. As used herein, the term "effective amount" can refer to the amount of a compound provided herein to increase or decrease activity of PTEN by 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, 200 percent or more. The term "effective amount" can refer to the amount of a compound and/or formulation thereof described herein to increase or decrease activity of PTEN by 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, to/or 200 percent or more when the compound is present at a concentration of about 1 µM or less. The term "effective amount" can also be used interchangeably herein with "pharmaceutically acceptable amount." Pharmaceutically effective amount" or "pharmaceutically effective dose," can refer to the amount of a compound or formulation thereof provided herein that will elicit the biological and/or medical response of a cell, tissue, organ, system, or subject that is being sought by the researcher, veterinarian, medical doctor or other clinician. Specific desired effects are discussed elsewhere herein. The pharmaceutically effective amount can vary depending on the compound, formulation the disorder or condition (normal or abnormal) and its severity, the route of administration, time of administration, rate of excretion, drug or compound, judgment of the researcher, veterinarian, medical doctor or other clinician, dosage form, and the age, weight, general health, sex and/or diet of the subject to be treated.

As used herein, "hydrate" can refer to a compound formed by the addition of water. Typically, but not always, this will be crystalline lattice structures that incorporate water molecules. Hydrates include stoichiometric hydrates, as well as compositions containing variable amounts of water.

As used herein, "immunomodulator," can refer to an agent, such as a therapeutic agent, which is capable of modulating or regulating one or more immune function or response.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

As used herein, "mitigate" can refer to reducing a particular characteristic, symptom, or other biological or physiological parameter associated with a disease or disorder.

The term "molecular weight", as used herein, can generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "pharmaceutical formulation" can refer to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable" can refer to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration.

As used herein, "pharmaceutically acceptable carrier or excipient" can refer to a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used herein also includes both one and more than one such carrier or excipient. Pharmaceutically acceptable carriers include, but are not limited to, diluents, preservatives, binders, lubricants, disintegrators, swelling agents, fillers, stabilizers, and combinations thereof.

As used herein, "pharmaceutically acceptable salt" can refer to any salt derived from organic and inorganic acids of a compound described herein. Pharmaceutically acceptable salt also refers to a salt of a compound described having an acidic functional group, such as a carboxylic acid functional group, and a base. Pharmaceutically acceptable salt also includes hydrates of a salt of a compound described herein.

As used herein, "positive control" can refer to a "control" that is designed to produce the desired result, provided that all reagents are functioning properly and that the experiment is properly conducted.

As used herein, "protein" as used herein can refer to a molecule composed of one or more chains of amino acids in a specific order. The term protein is used interchangeable with "polypeptide." The order is determined by the base sequence of nucleotides in the gene coding for the protein. Proteins are required for the structure, function, and regulation of the body's cells, tissues, and organs.

As used herein, "purified" or "purify" can be used in reference to a nucleic acid sequence, peptide, or polypeptide that has increased purity relative to the natural environment.

As used herein, "preventative," "preventing," "prevent" and the like can refer to partially or completely delaying and/or precluding the onset or recurrence of a disorder or conditions and/or one or more of its attendant symptoms or barring a subject from acquiring or reacquiring a disorder or condition or reducing a subject's risk of acquiring or reacquiring a disorder or condition or one or more of its attendant symptoms including, but not limited to all cancers that have compromised PTEN activity or function and all those cancers wherein there is hyperactivity of the PI3K/AKT/mTOR/S6K signaling pathway An extensive list of all PTEN-related cancers which are included within the scope of this disclosure can be found at the National Institute of Health website. The main malignancies can include, but are not limited to, cancers of the breast, prostate, lung, endometrium, head and neck squamous cell carcinoma (HNSCC), ovary, colon, colo-rectal, lymphoma, mesothelioma, salivary gland, testicular cancers, cancers of the thyroid, skin, and stomach, soft tissue sarcoma, cancers of the brain including glioblastomas and astrocytomas, aggressive form of skin cancers such as melanomas and head and neck squamous cell carcinomas. More extensive information on PTEN-related cancers can be found National Institute of Health website. The compounds and formulations thereof described herein can be effective to prevent other PTEN-related diseases including all the "PTEN-Opathies" (PTEN hamartoma tumor syndromes (PHTS), Bannayan-Riley-Ruvalcaba syndrome (BRRS), Juvenile polyposis of infancy (JPI), Cowden's syndrome, Hemangiomas, Immune dysregulation, PTEN-related Proteus syndrome (PS), Lhermitte-Duclos disease (LDD), Autism and Autism/pervasive developmental disorder and macrocephaly, Alzheimer's disease, Parkinsonism and metabolic disorders/obesity), which are associated with aberrant PTEN function. (Am J Med Genet C Semin Med Genet. 2013 Apr. 9). The compounds and formulations thereof described herein can be effective to modulate PTEN activity. The compounds and formulations thereof described herein can also be effective prevent and/or modulate PTEN activity in TBI (Traumatic Brain injury), neural ischemia, amyotrophic lateral sclerosis (ALS), and other neurodegenerative diseases. The compounds and formulations thereof described herein can also be effective to promote regrowth of the corticospinal tract, including, but not limited to, the axons. As used herein, "separated" can refer to the state of being physically divided from the original source or population such that the separated compound, agent, particle, chemical compound, or molecule can no longer be considered part of the original source or population.

As used herein, "solvate" refers to a complex of variable stoichiometry formed by a solute (e.g. formulas (1)-(1) (A), (B), (C), (D), or any other compound herein or a salt thereof) and a solvent. Pharmaceutically acceptable solvates may be formed for crystalline compounds wherein solvent molecules are incorporated into the crystalline lattice during crystallization. The incorporated solvent molecules can be water molecules or non-aqueous molecules, such as but not limited to, ethanol, isopropanol, dimethyl sulfoxide, acetic acid, ethanolamine, and ethyl acetate molecules.

As used herein, the term "specific binding" can refer to non-covalent physical association of a first and a second moiety wherein the association between the first and second moieties is at least 2 times as strong, at least 5 times as strong as, at least 10 times as strong as, at least 50 times as strong as, at least 100 times as strong as, or stronger than the association of either moiety with most or all other moieties present in the environment in which binding occurs. Binding of two or more entities may be considered specific if the equilibrium dissociation constant, Kd, is $10^{-3}$ M or less, $10^{-4}$ M or less, $10^{-5}$ M or less, $10^{-6}$ M or less, $10^{-7}$ M or less, $10^{-8}$ M or less, $10^{-9}$ M or less, $10^{-10}$ M or less, $10^{-11}$ M or less, or $10^{-12}$ M or less under the conditions employed, e.g., under physiological conditions such as those inside a cell or consistent with cell survival. In some embodiments, specific binding can be accomplished by a plurality of weaker interactions (e.g., a plurality of individual interactions, wherein each individual interaction is characterized by a Kd of greater than $10^{-3}$ M). In some embodiments, specific binding, which can be referred to as "molecular recognition," is a saturable binding interaction between two entities that is dependent on complementary orientation of functional groups on each entity. Examples of specific binding interactions include primer-polynucleotide interaction, aptamer-aptamer target interactions, antibody-antigen interactions, avidin-biotin interactions, ligand-receptor interactions, metal-chelate interactions, hybridization between complementary nucleic acids, etc.

As used interchangeably herein, "subject," "individual," or "patient," can refer to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

The terms "sufficient" and "effective," as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "synergistic effect," "synergism," or "synergy" can refer to an effect arising between two or more molecules, compounds, substances, factors, or compositions that that is greater than or different from the sum of their individual effects.

As used herein, "therapeutic", "treating", "treat," and the like can refer to include partially or completely delaying, alleviating, mitigating or reducing the intensity of one or more attendant symptoms of a disease or condition including, but not limited to, those involving PTEN or analogue thereof, and/or a ligand of PTEN or analogue thereof. The disease can be one that can be treated by the compounds and/or formulations provided herein. Some diseases include, but are not limited to, all cancers that have compromised PTEN activity or function and all those cancers wherein there is hyperactivity of the PI3K/AKT/mTOR/S6K signaling pathway. An extensive list of all PTEN-related cancers which are included within the scope of this disclosure can be found at the National Institute of Health website. The main malignancies include, but are not limited to, cancers of the breast, prostate, lung, endometrium, head and neck squamous cell carcinoma (HNSCC), ovary, colon, colo-rectal, lymphoma, mesothelioma, salivary gland, testicular cancers, cancers of the thyroid, skin, stomach, soft tissue sarcoma, cancers of the brain including glioblastomas and astrocytomas, aggressive form of skin cancers such as melanomas and head and neck squamous cell carcinomas. More extensive information on PTEN-related cancers can be found National Institute of Health website. The compounds and formulations described herein can treat other PTEN-related diseases including all the "PTEN-Opathies" (PTEN hamartoma tumor syndromes (PHTS), Bannayan-Riley-Ruvalcaba syndrome (BRRS), Juvenile polyposis of infancy (JPI), Cowden's syndrome, Hemangiomas, Immune dysregulation, PTEN-related Proteus syndrome (PS), Lhermitte-Duclos disease (LDD), Autism and Autism/pervasive developmental disorder and macrocephaly, Alzheimer's disease, Parkinsonism and metabolic disorders/obesity), which are associated with aberrant PTEN function. (Am J Med Genet C Semin Med Genet. 2013 Apr. 9). The compounds and formulations described herein can modulate PTEN activity. The compounds and formulations described herein can treat and/or modulate PTEN activity in TBI (Traumatic Brain injury), neural ischemia, amyotrophic lateral sclerosis (ALS), and other neurodegenerative diseases. The compounds and formulations thereof described herein can also promote regrowth of the corticospinal tract, including, but not limited to, the axons.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. "Variant" includes functional and structural variants.

As used herein, "alkyl" and "alkylene" refer to a saturated hydrocarbon chain having the specified number of member atoms.

The term "alkyl" can also refer to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups. "Alkyl" also refers to a saturated hydrocarbon chain having the specified number of atoms.

The term "alkyl" (or "lower alkyl") as used herein can include both "unsubstituted alkyls" and "substituted alkyls," the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein can refer to an alkyl group, as defined above, but having from one to ten carbons in its backbone structure. Likewise, "lower alkenyl" and "lower alkynyl" have similar chain lengths.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF$_3$, —CN and the like. Cycloalkyls can be substituted in the same manner.

As used herein, "C$_{1-6}$alkyl" can refer to an alkyl group having any number of member atoms from 1 to 6 member atoms, such as for example 1 to 4 atoms. Other alkyl groups may have any number of member atoms as indicated by the numbers given in the formula, which, like the previous example, can refer to an alkyl group having any number of member atoms within the specified range of member atoms. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

As used herein, "heterocyclic group" can refer to a non-aromatic ring and having the specified number of member atoms being saturated or having one or more degrees of unsaturation and, unless otherwise specified, containing one or more heteroatoms.

As used herein, "heteroaryl" can refer to an aromatic ring having the specified number of member atoms and, unless otherwise specified, containing one or more heteroatoms. Bicyclic and other polycyclic ring systems having a heteroaryl ring are described as fused systems.

The term "heteroalkyl," as used herein, can refer to straight or branched chain, or cyclic carbon-containing radicals, or combinations thereof, containing at least one heteroatom. Suitable heteroatoms include, but are not limited to, 0, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "heteroalkyl," as used herein, can refer to straight or branched chain, or cyclic carbon-containing radicals, or combinations thereof, containing at least one heteroatom. Suitable heteroatoms include, but are not limited to, 0, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, "alkoxyl" or "alkoxy," as used herein, can refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl is an ether or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

As used herein, "amine" and "amino" (and its protonated form) are art-recognized and refer to both unsubstituted and substituted amines, e.g., a moiety that can be represented by the general formula:

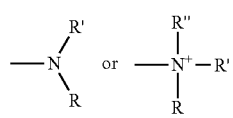

wherein R, R', and R" each independently represent a hydrogen, an alkyl, an alkenyl, —(CH2)$_m$-R$_C$ or R and R' taken together with the N atom to which they are attached complete a heterocycle having from 4 to 8 atoms in the ring structure; R$_C$ represents an aryl, a cycloalkyl, a cycloalkenyl, a heterocycle or a polycycle; and m is zero or an integer in the range of 1 to 8. In some embodiments, only one of R or R' can be a carbonyl, e.g., R, R' and the nitrogen together do not form an imide. In other embodiments, the term "amine" does not encompass amides, e.g., wherein one of R and R' represents a carbonyl. In further embodiments, R and R' (and optionally R") each independently represent a hydrogen, an alkyl or cycloakyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

As used herein, "amido" is art-recognized as an amino-substituted carbonyl and includes a moiety that can be represented by the general formula:

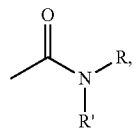

wherein R and R' are as defined above.

As used herein, "Aryl" can refer to C$_5$-C$_{10}$-membered aromatic, heterocyclic, fused aromatic, fused heterocyclic, biaromatic, or biheterocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics." The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, and combinations thereof.

The term "aryl" can also include polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl."

As used herein, "aralkyl," can refer to an alkyl group substituted with an aryl group (e.g., an aromatic or heteroaromatic group).

As used herein, "aralkyloxy" can be represented by —O-aralkyl, wherein aralkyl is as defined above.

As used herein, "carbocycle," can refer to an aromatic or non-aromatic ring(s) in which each atom of the ring(s) is carbon.

As used herein, "heterocycle" or "heterocyclic" can refer to a monocyclic or bicyclic structure containing 3-10 ring atoms, and in some embodiments, containing from 5-6 ring atoms, wherein the ring atoms are carbon and one to four heteroatoms each selected from the following group of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "carbonyl" is art-recognized and includes such moieties as can be represented by the general formula:

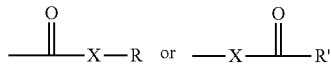

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid." Where X is an oxygen and R' is hydrogen, the formula represents a "formate." In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

As used herein, "heteroatom" as used herein can refer to an atom of any element other than carbon or hydrogen. Exemplary heteroatoms include, but are not limited to, boron, nitrogen, oxygen, phosphorus, sulfur, silicon, arsenic, and selenium.

As used herein, "nitro" can refer to —$NO_2$; the term "halogen" designates —F, —Cl, —Br, or —I; the term "sulfhydryl" refers to —SH; the term "hydroxyl" refers to —OH; and the term "sulfonyl" refers to —$SO_2$—.

The term "substituted" as used herein, can refer to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, e.g. 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms, such as nitrogen, can have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

As used herein, "suitable substituent" can refer to a chemically and pharmaceutically acceptable group, i.e., a moiety that does not significantly interfere with the preparation of or negate the efficacy of the inventive compounds. Such suitable substituents may be routinely chosen by those skilled in the art. Suitable substituents include but are not limited to the following: a halo, $C_1$-$C_6$ alkyl, $C_2$-$C_6$ alkenyl, $C_1$-$C_6$ haloalkyl, $C_1$-$C_6$ alkoxy, $C_1$-$C_6$ haloalkoxy, $C_2$-$C_6$ alkynyl, $C_3$-$C_8$ cycloalkenyl, ($C_3$-$C_8$ cycloalkyl)$C_1$-$C_6$ alkyl, ($C_3$-$C_8$ cycloalkyl)$C_2$-$C_6$ alkenyl, ($C_3$-$C_8$ cycloalkyl) $C_1$-$C_6$ alkoxy, $C_3$-$C_7$ heterocycloalkyl, ($C_3$-$C_7$ heterocycloalkyl) $C_1$-$C_6$ alkyl, ($C_3$-$C_7$ heterocycloalkyl)$C_2$-$C_6$ alkenyl, ($C_3$-$C_7$ heterocycloalkyl)$C_1$-$C_6$ alkoxyl, hydroxy, carboxy, oxo, sulfanyl, $C_1$-$C_6$ alkylsulfanyl, aryl, heteroaryl, aryloxy, heteroaryloxy, arylalkyl, heteroaralkyl, arylalkoxy, heteroaralkoxy, nitro, cyano, amino, $C_1$-$C_6$ alkylamino, di-($C_1$-$C_6$ alkyl)amino, carbamoyl, ($C_1$-$C_6$ alkyl)carbonyl, ($C_1$-$C_6$ alkoxy)carbonyl, ($C_1$-$C_6$ alkyl)aminocarbonyl, di-($C_1$-$C_6$ alkyl)aminocarbonyl, arylcarbonyl, aryloxycarbonyl, ($C_1$-$C_6$ alkyl)sulfonyl, and arylsulfonyl. The groups listed above as suitable substituents are as defined hereinafter except that a suitable substituent may not be further optionally substituted.

As used herein, "optionally substituted" can indicate that a group may be unsubstituted or substituted with one or more substituents as defined herein.

Discussion

PTEN (Phosphatase and Tensin homolog) is the second most mutated tumor suppressor protein in multiple cancers, after p53. Also, PTEN germline mutations cause PTEN Hamartoma Tumour Syndrome (PHTS), including Cowden, Bannayan-Riley-Ruvalcalba and Proteus syndromes. Recently, cerebellum dysplastic hamartoma (Lhermitte Duclos syndrome), juvenile polyposis of infancy, segmental overgrowth, and autism spectrum disorder with macrocephaly have been associated with PTEN mutations. Conversely, an emerging body of evidence indicates that non-genomic loss of PTEN function via post-transcriptional/translational mechanisms or mislocalization also plays a critical role in pathogenesis of various cancers. Pandolfi's group proposed the continuum model, in which PTEN acts as a rheostat, differentially modulating cellular activity depending upon its levels of expression (Nature. 2011 Aug. 10; 476(7359): 163-169. doi: 10.1038/nature10275) Reduced PTEN expression indeed confers increased PI3K/AKT activation and may lead to oncogenesis in a given tissue. Thus, every tissue has a defined threshold for PTEN expression, reduction in which leads to cancer or other above mentioned PTENopathies.

PTEN is a 403 amino acid long dual-specificity (lipid and protein) phosphatase comprising of an N-terminal PIP2 (phosphatidylinositol-4,5-bisphosphate) binding domain (PBD), a catalytic phosphatase domain (PD), a plasma membrane binding C2-domain (C2D) and an intrinsically disordered carboxyl-terminal domain (C-tail) consisting of a PDZ-binding domain. PTEN mainly asserts its tumor suppressive function as a lipid phosphatase, by reducing PIP3 (phosphatidylinositol-3,4,5-triphosphate) levels, thereby inhibiting the oncogenic activation of the PI3K/AKT/S6K signaling pathway. PTEN regulates cell cycle progression, angiogenesis, cell polarity, apoptosis and metabolism through its lipid and protein phosphatase-dependent and -independent mechanisms. Therefore, PTEN is a central molecule, which plays important roles in cellular physiology and homeostasis.

Aberrant PI3K/AKT/S6K pathway signaling drive cancers by enhancing cell growth, survival, proliferation, migration and invasion, and alter cellular metabolism. PTEN expression can play a role in suppressing oncogenic potential. Reduced PTEN expression or activity is observed in various cancers and neurological diseases, and currently, there are no known molecules that directly activate PTEN function.

Current therapies for cancers driven by hyperactive PI3K/AKT/S6K pathway include the use of kinase inhibitors targeting one or more kinases. Despite some clinical success with these inhibitors, their benefit has been stymied by off-target effects and drug resistance due to formation of alternative signaling feedback loops.

With that said, described herein are compounds and formulations thereof that can be capable of binding and/or activating or inhibiting PTEN. Also described herein are methods of inhibiting or activating PTEN by contacting PTEN with a compound or formula thereof provided herein. Also described herein are methods of inhibiting or activation PTEN in a subject that include the step of administering a compound or formula thereof provided herein to the subject. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

PTEN Binding Compounds and Formulations Thereof

Provided herein are compounds that can bind and/or activate or inhibit PTEN activity. The compounds can be peptidomimetics. The compounds can have a structure according to Formula

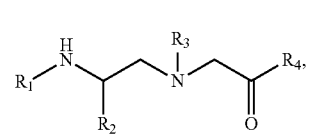

Formula 1 where R₁ can be H,
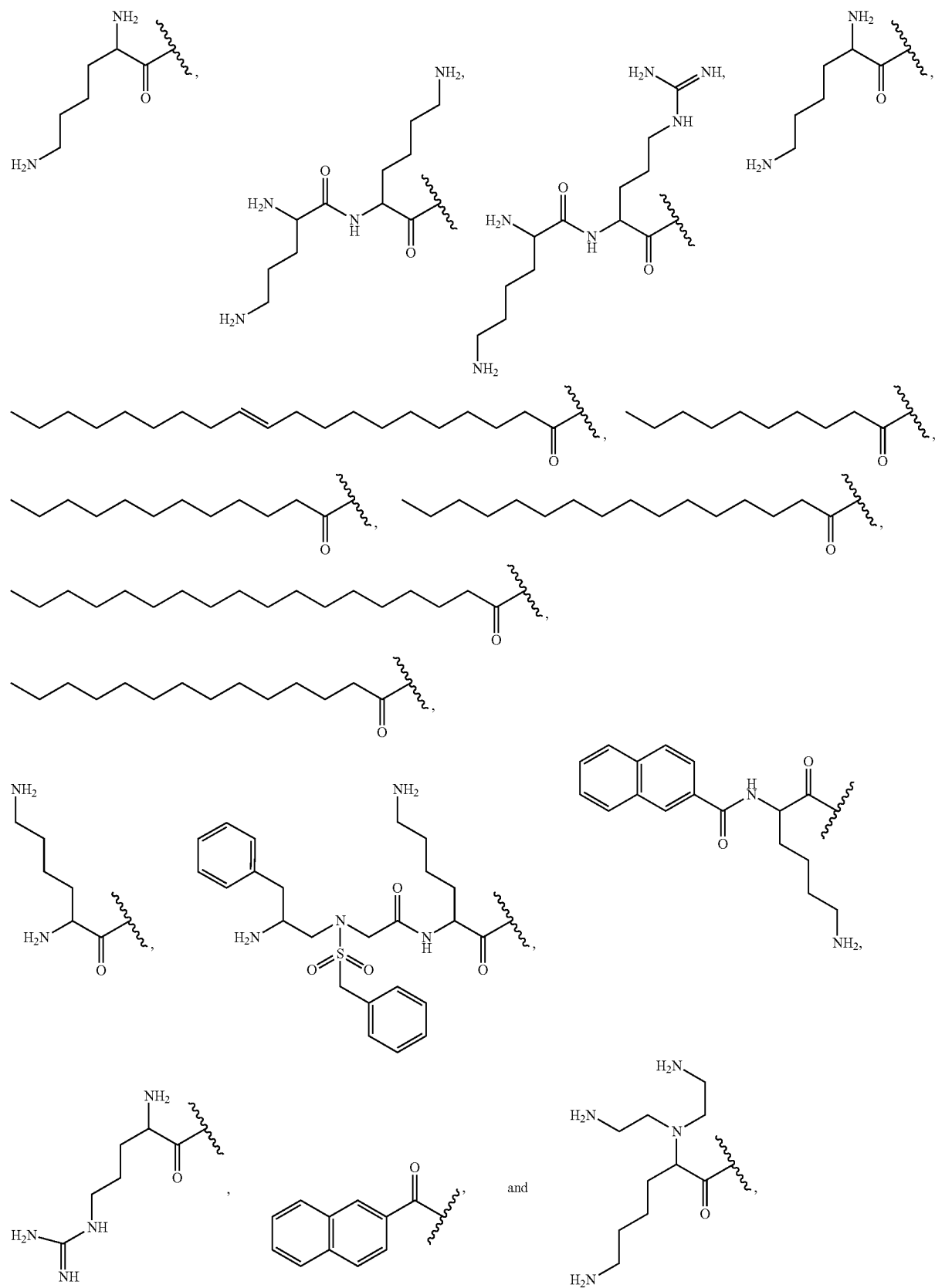

where R₂ can be
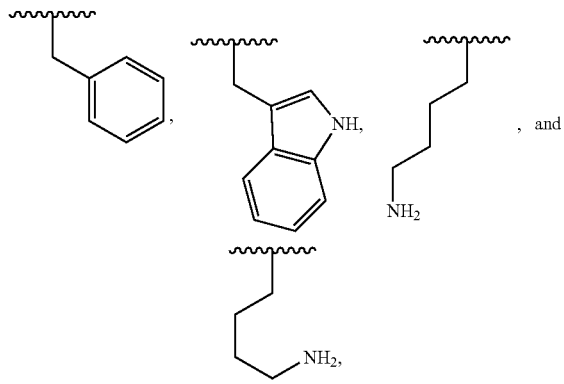
where R₃ can be
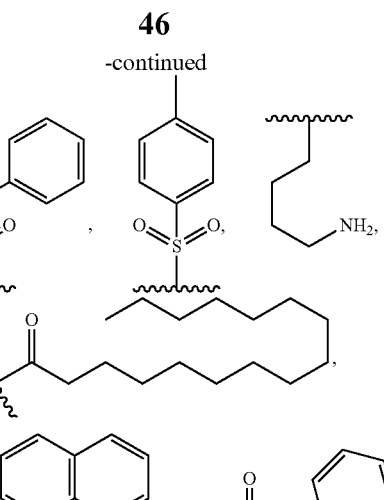
where R₄ can be
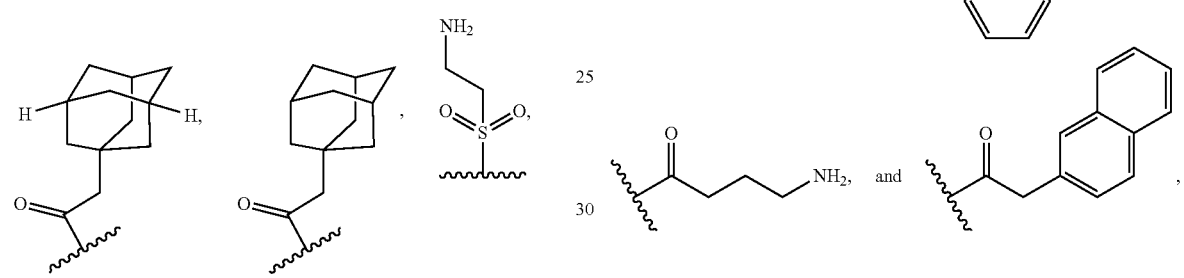

47                                                                48
-continued
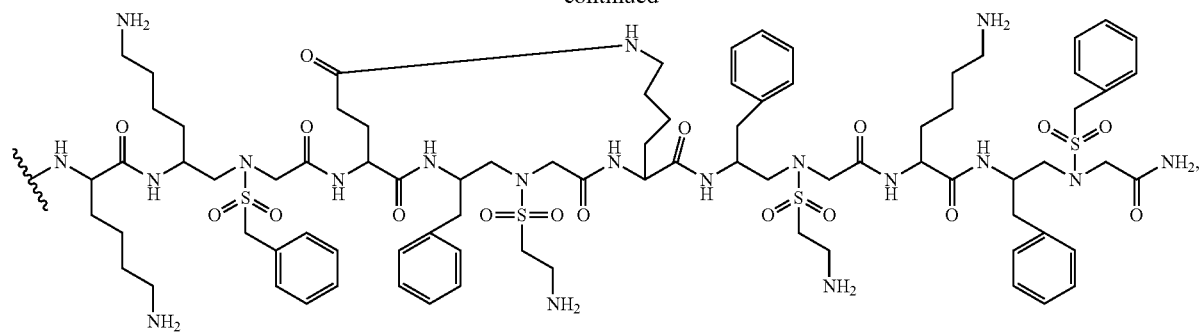
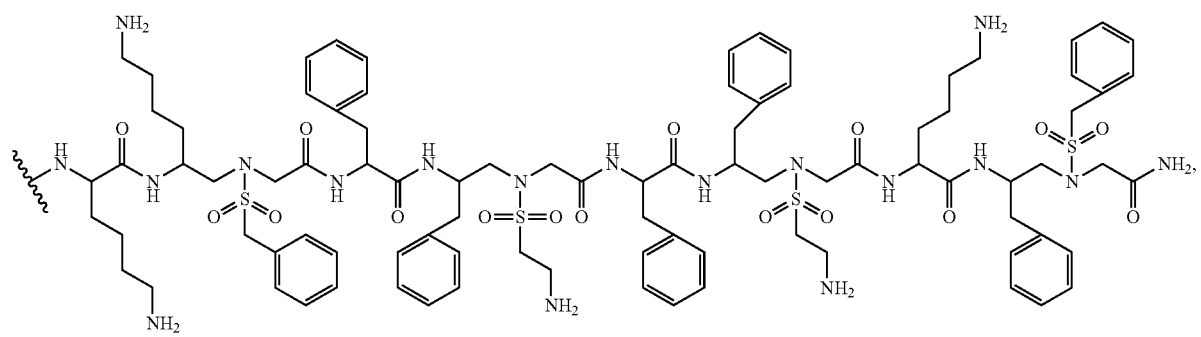
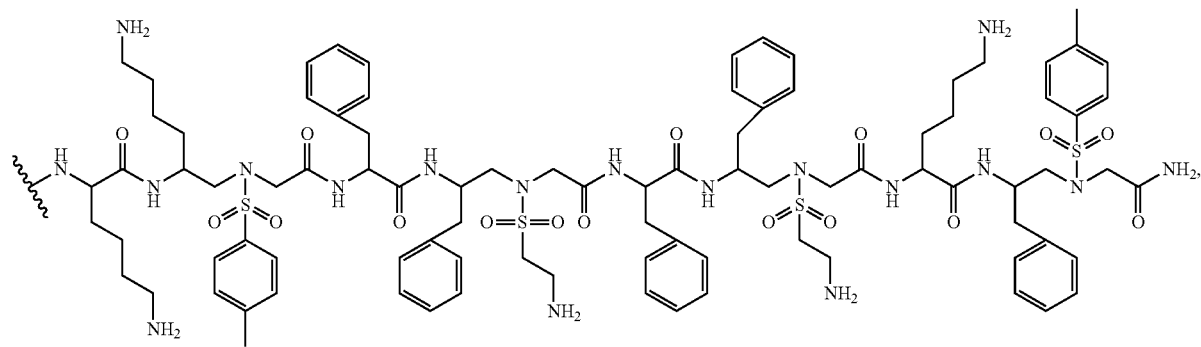
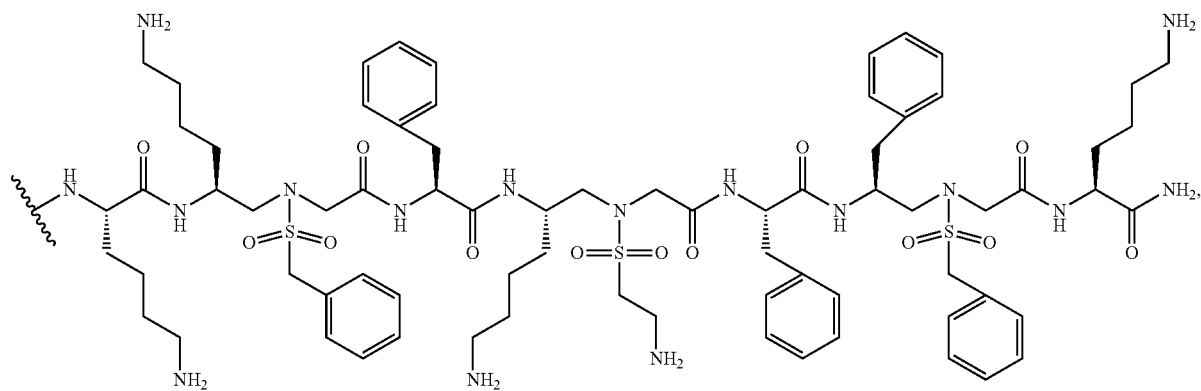

49
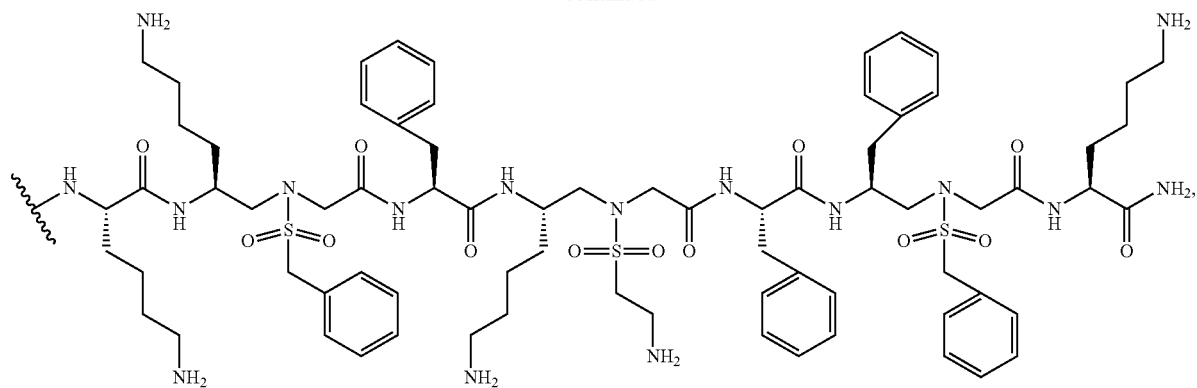
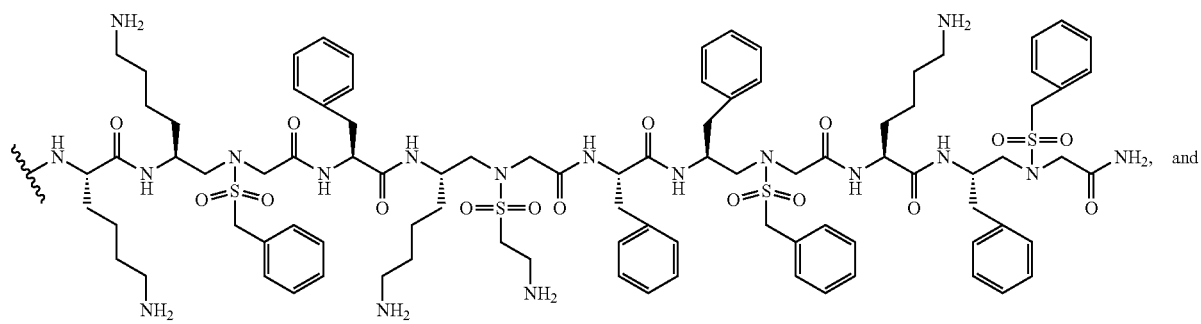
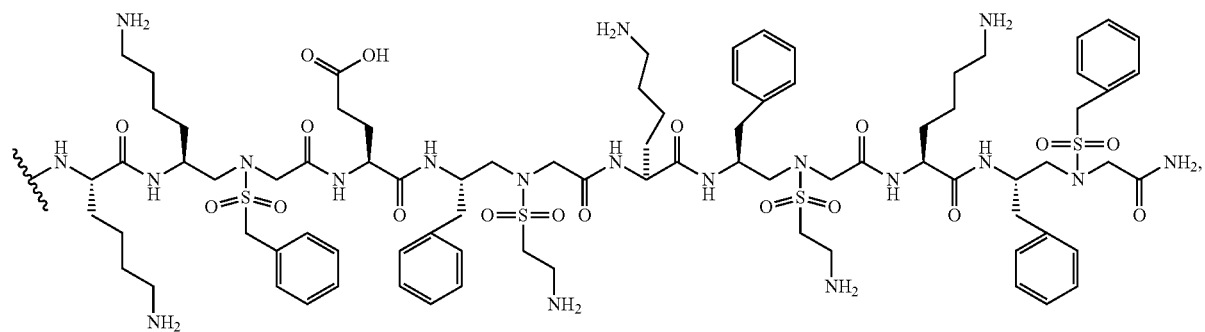

or where R₃ and R₄ can together form
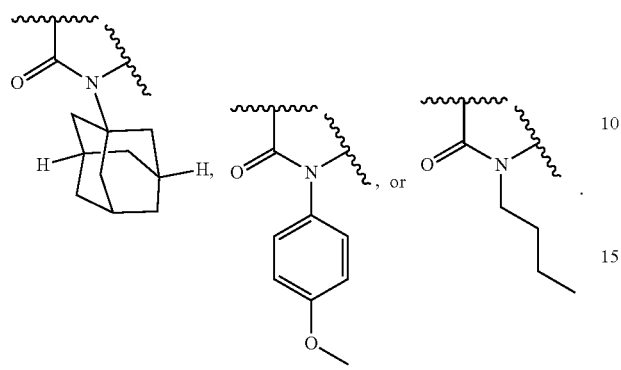
In some embodiments, the PTEN binding compound can have a structure according to any one of compounds (1)-(51).
(1)
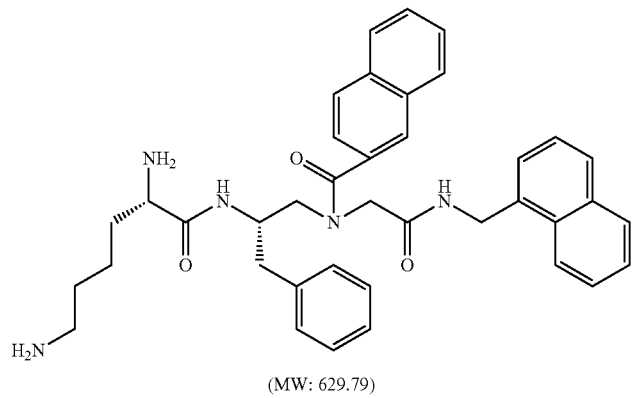
(MW: 629.79)
(2)
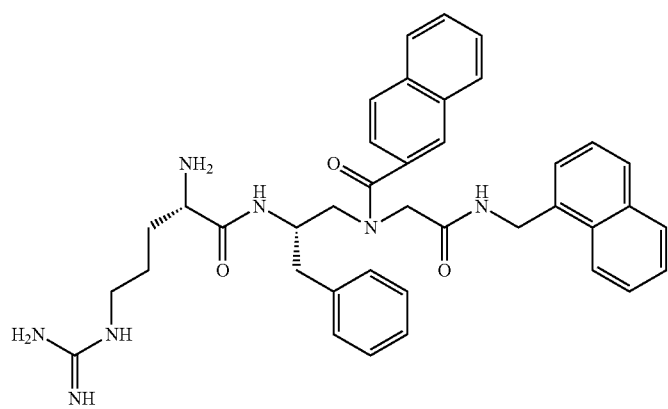
(MW: 657.8)

-continued
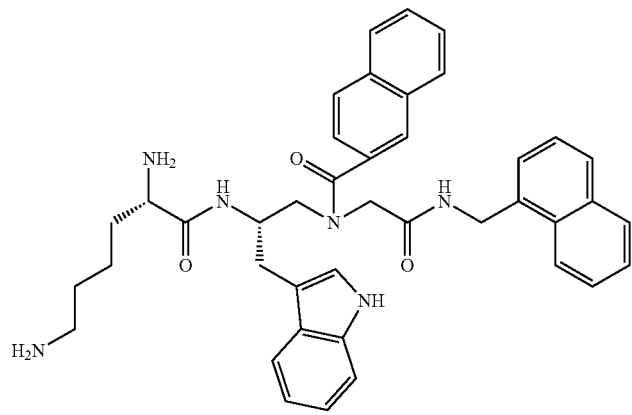
(MW:668.83) (3)
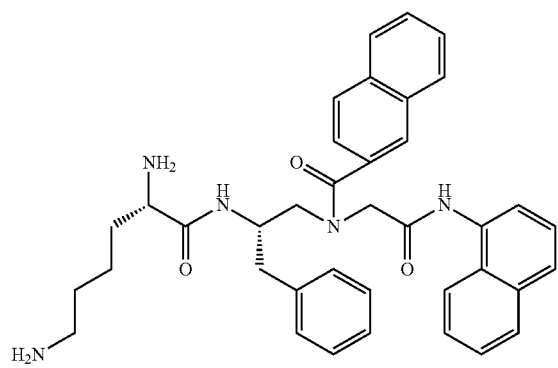
(MW:615.76) (4)
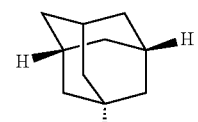 (5)
(MW: 637.85)
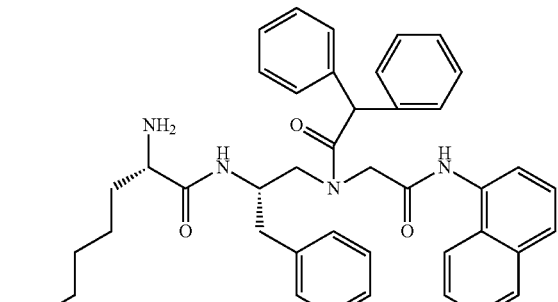
(MW: 655.83) (6)
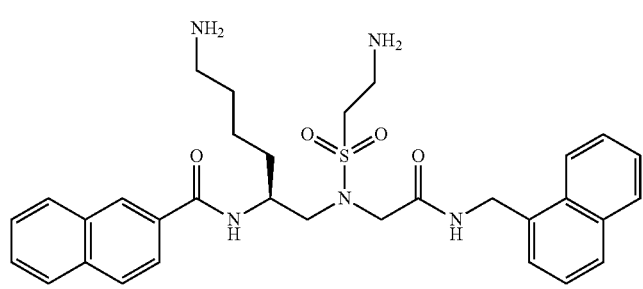
(MW: 589.75) (7)

(8)
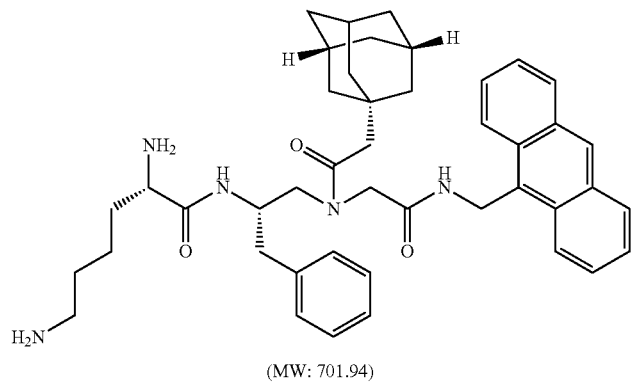
(MW: 701.94)
(9)
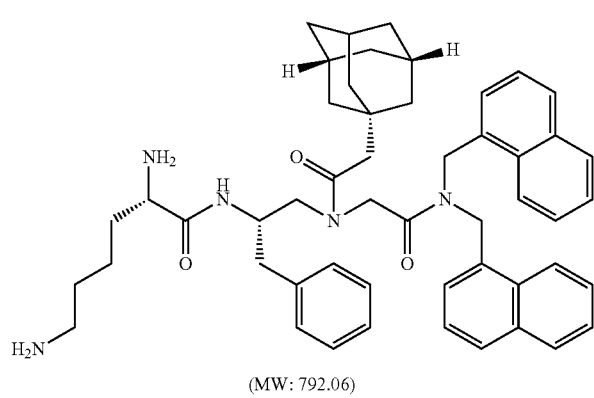
(MW: 792.06)
(10)
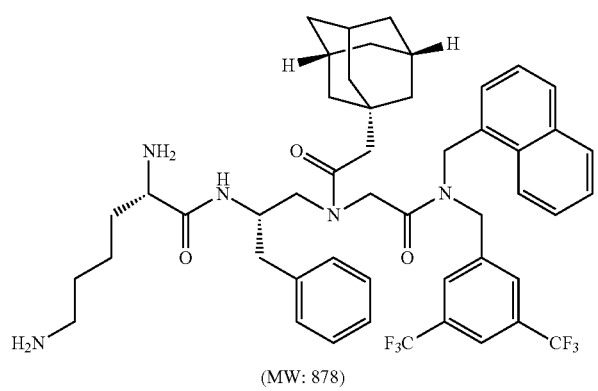
(MW: 878)
(11)
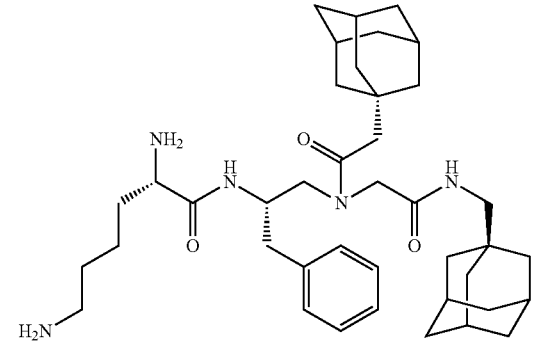
(MW: 659.96)
(12)
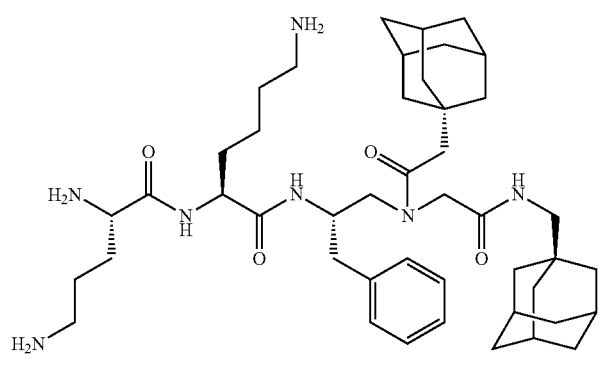
(MW: 774.11)
(13)
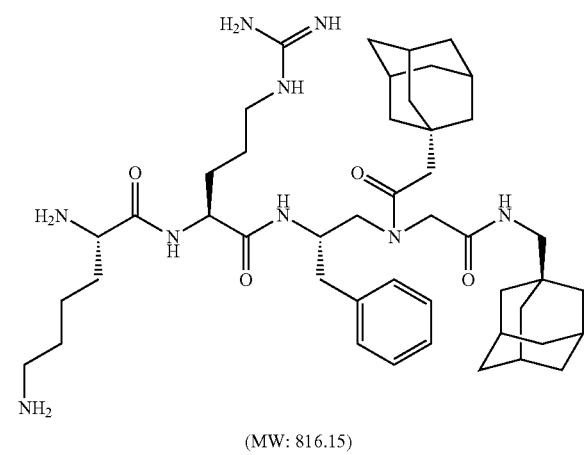
(MW: 816.15)

(14)
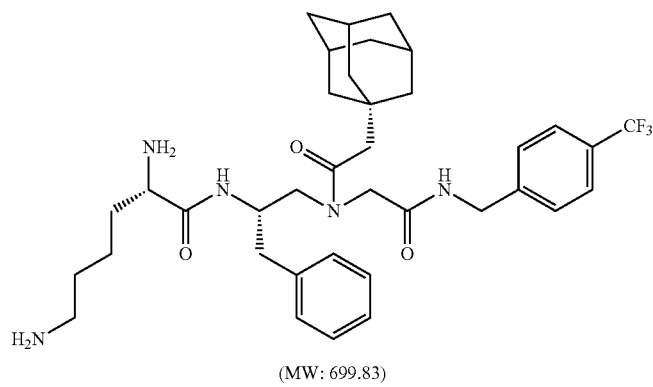
(MW: 699.83)
(15)
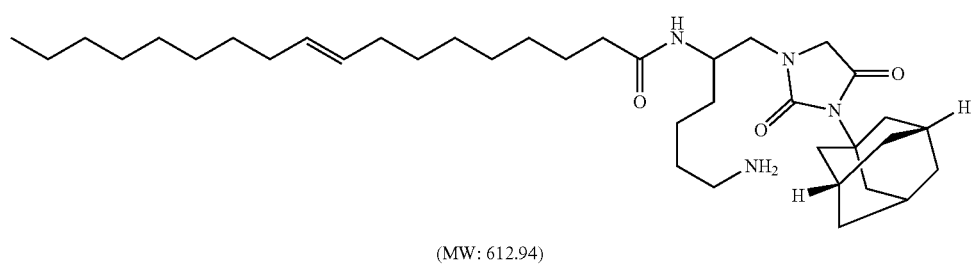
(MW: 612.94)
(16)
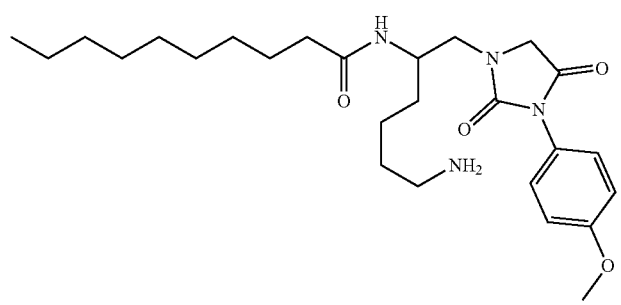
(MW: 474.65)
(17)
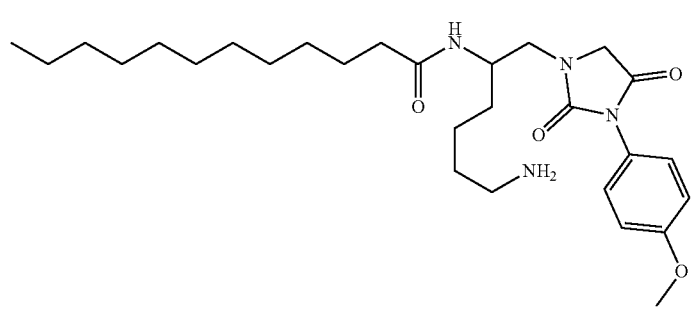
(MW: 502.7)
(18)
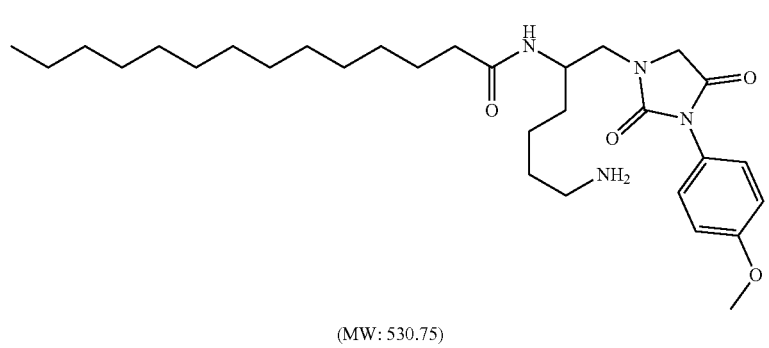
(MW: 530.75)

-continued
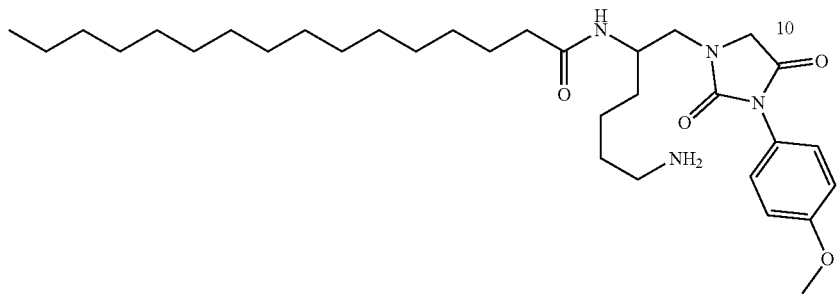
(19)
(MW: 558.81)
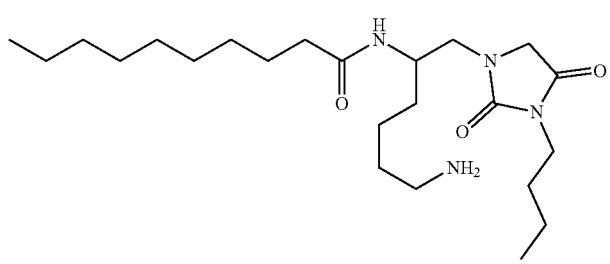
(20)
(MW: 424.63)
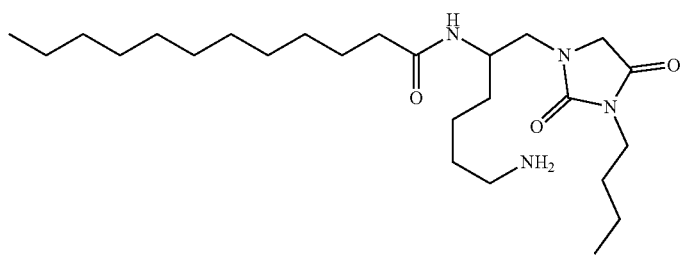
(21)
(MW: 452.68)
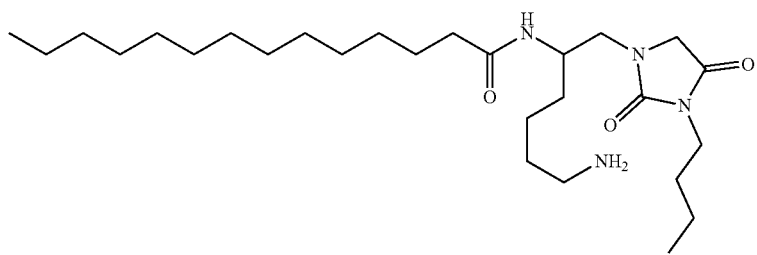
(22)
(MW: 480.74)
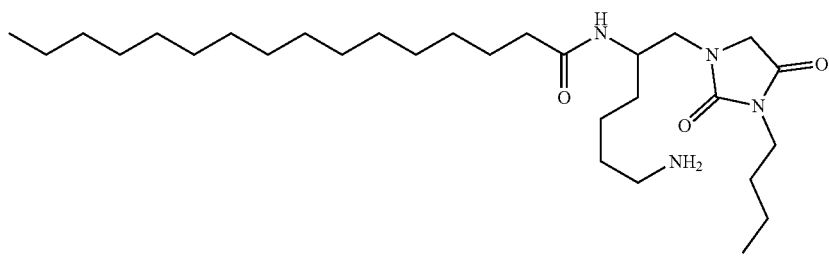
(23)
(MW: 508.79)

(24)
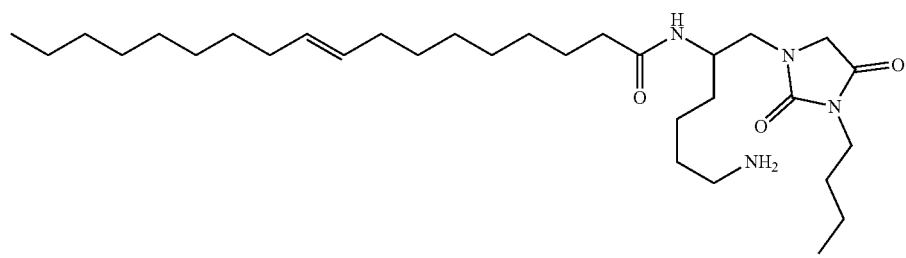
(MW: 534.83)
(25)
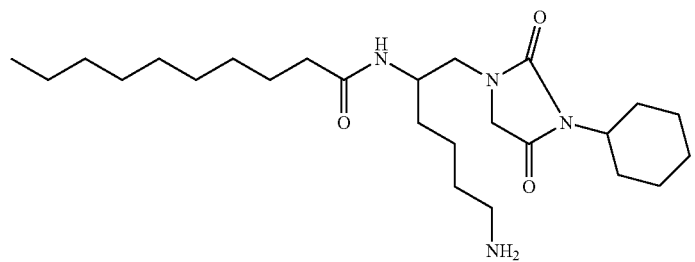
(MW: 450.67)
(26)
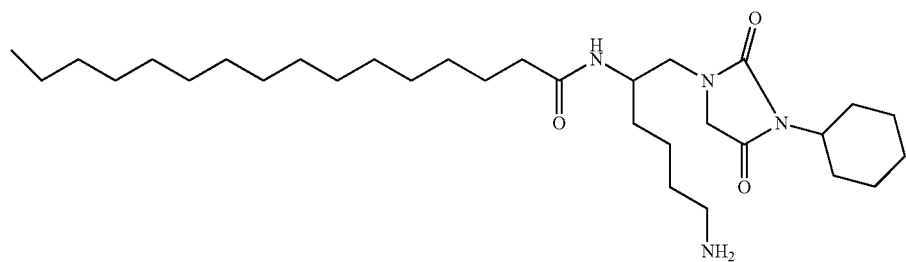
(MW: 534.83)
(27)
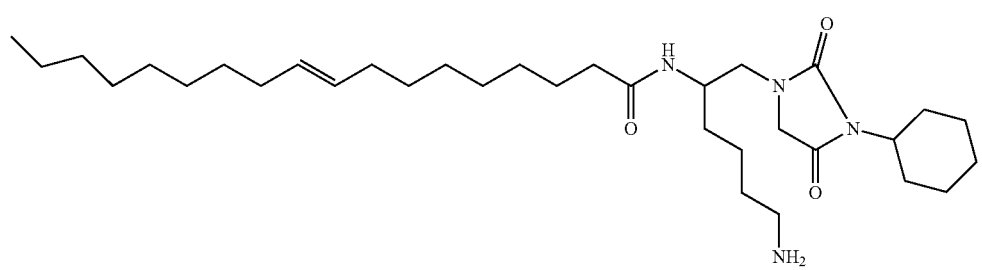
(MW: 560.87)
(28)
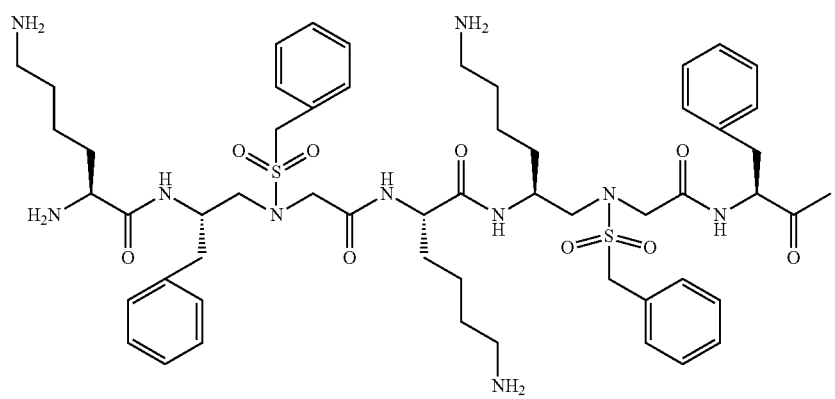
(MW: 1988.57)

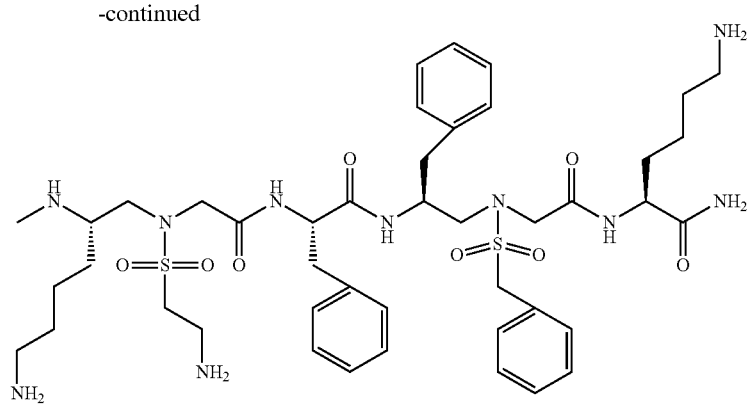
(29)
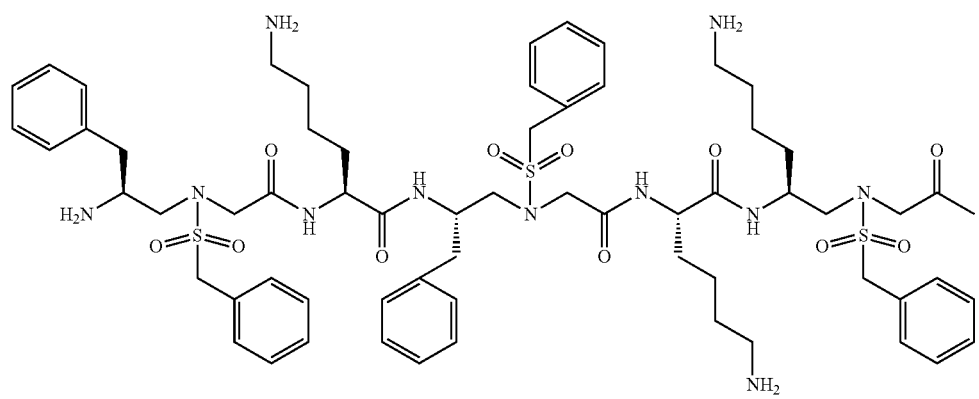
(MW: 2332.99)
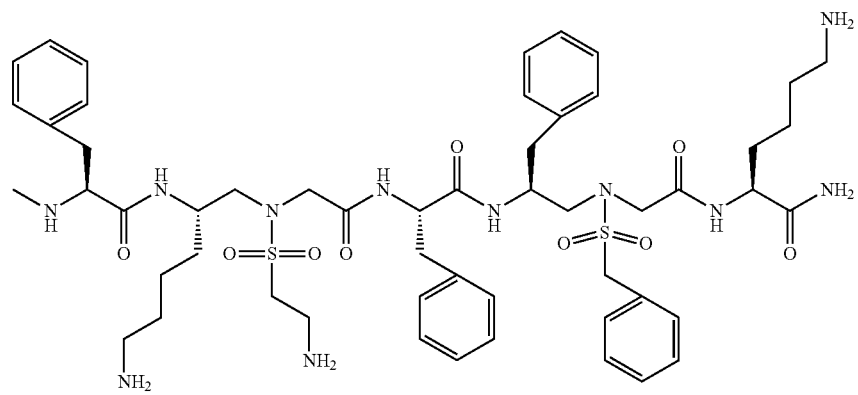
(30)
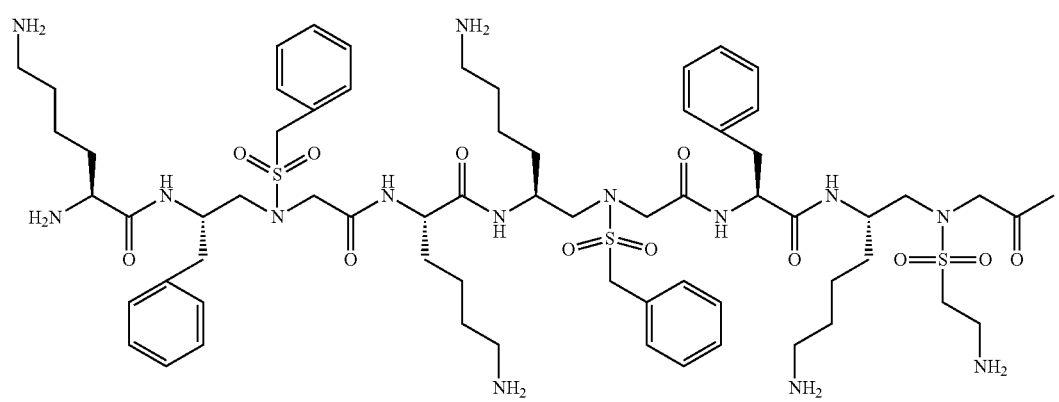
(MW: 2332.99)

-continued
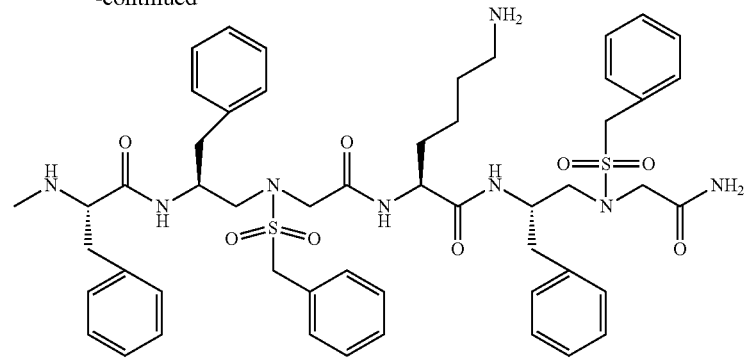
(31)
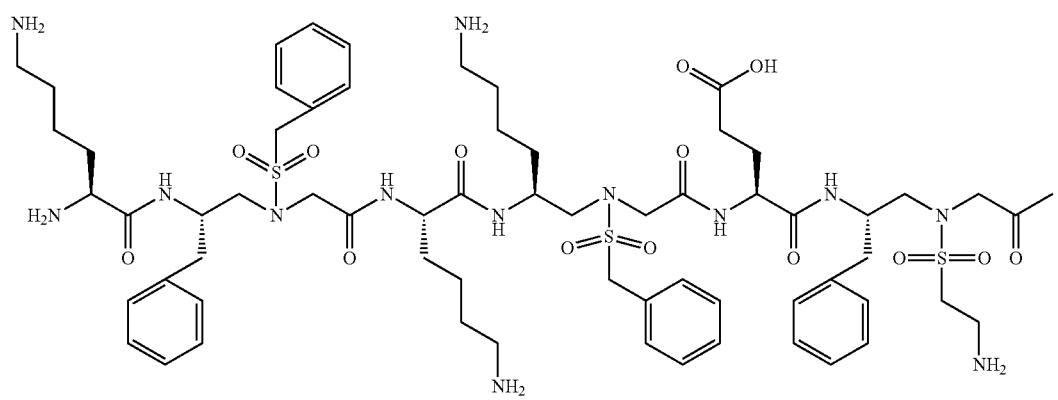
(MW: 2267.877)
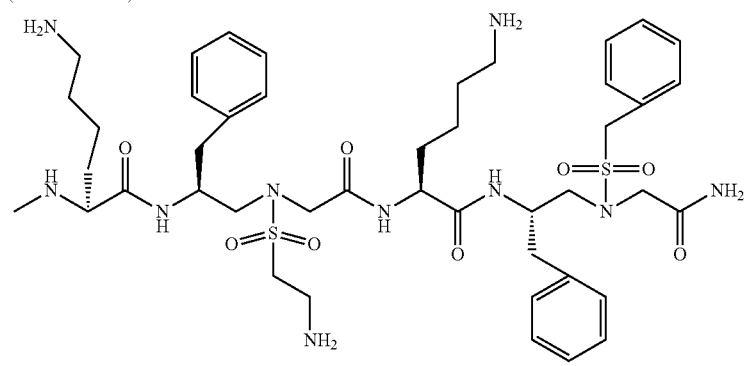
(32)
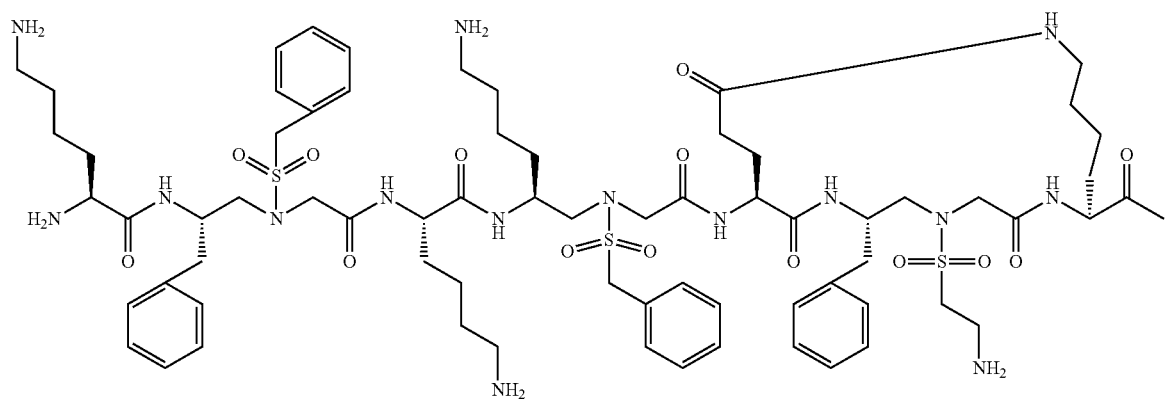
(MW: 2249.862)

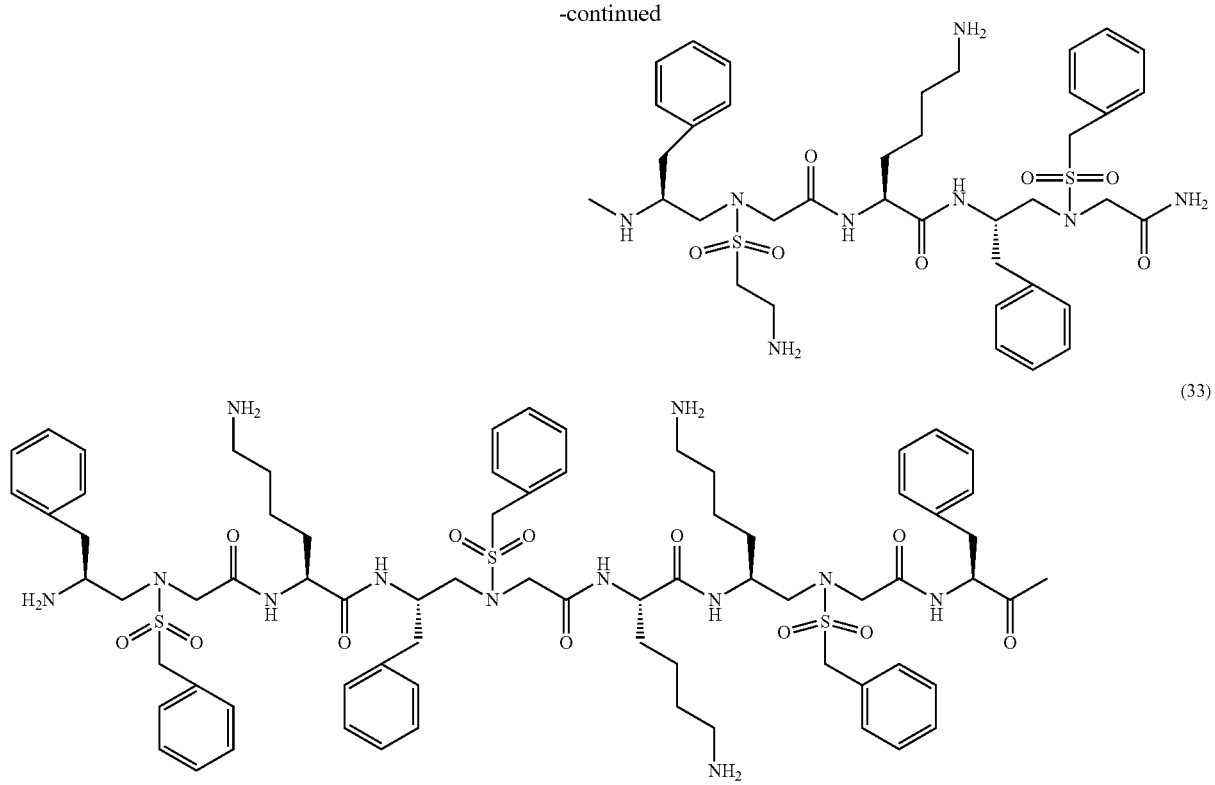
(33)
(MW: 2649.37)
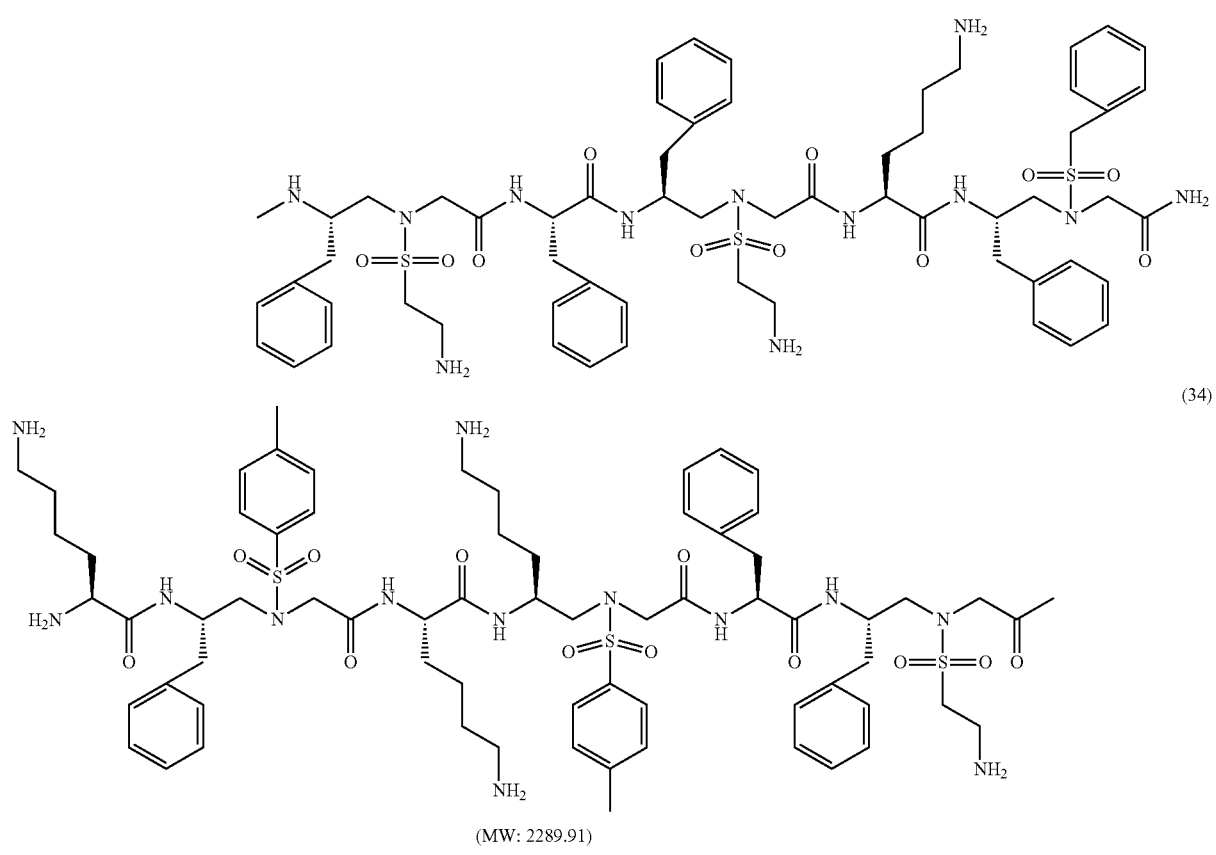
(34)
(MW: 2289.91)

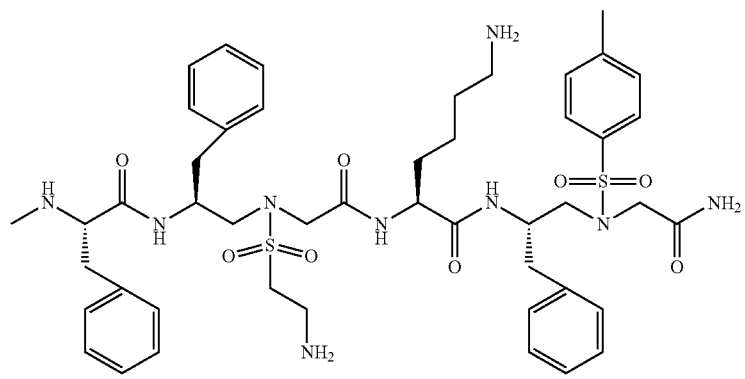
(35)
C₇₈H₁₁₆N₁₆O₁₁S₂
(MW: 1518.007)
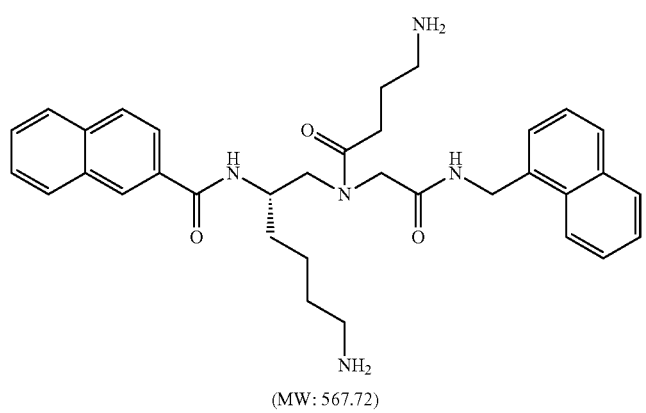
(36)
(MW: 567.72)
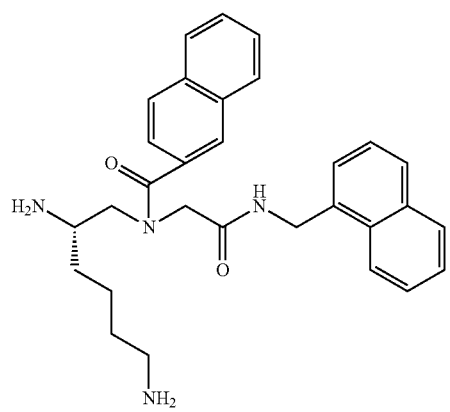
(37)
(MW: 482.62)

(38)
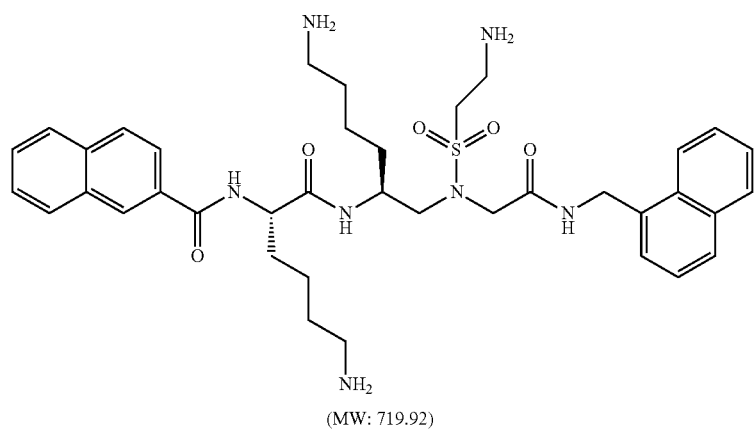
(MW: 719.92)
(39)
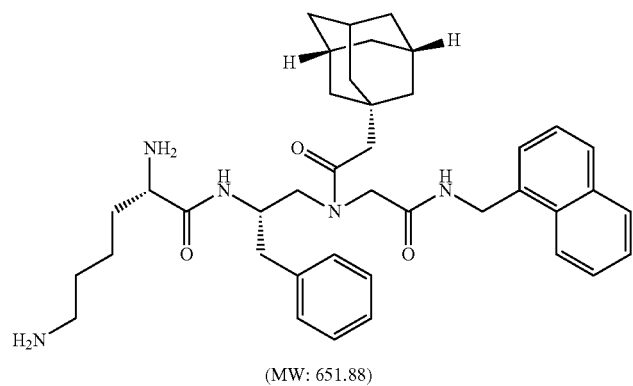
(MW: 651.88)
(40)
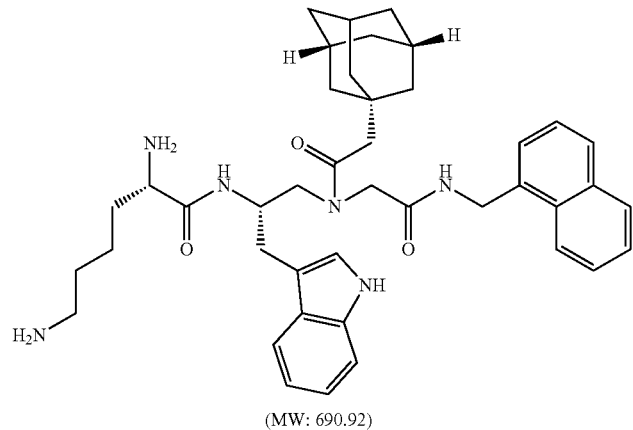
(MW: 690.92)
(41)
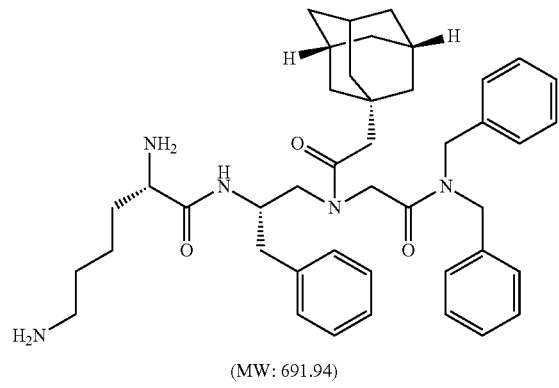
(MW: 691.94)

(42)
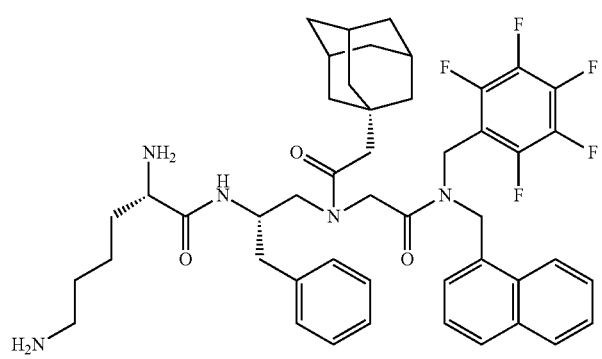
(MW: 831.96)
(43)
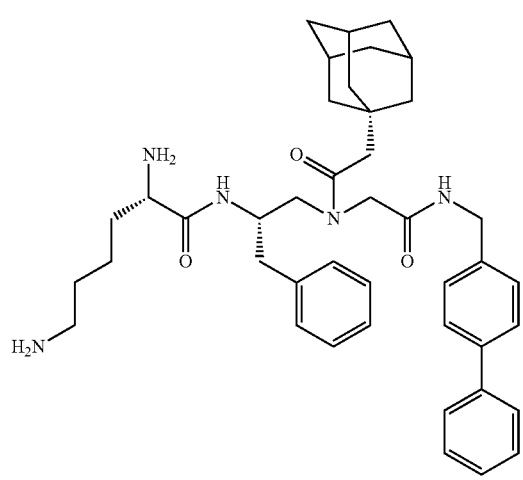
(MW: 677.92)
(44)
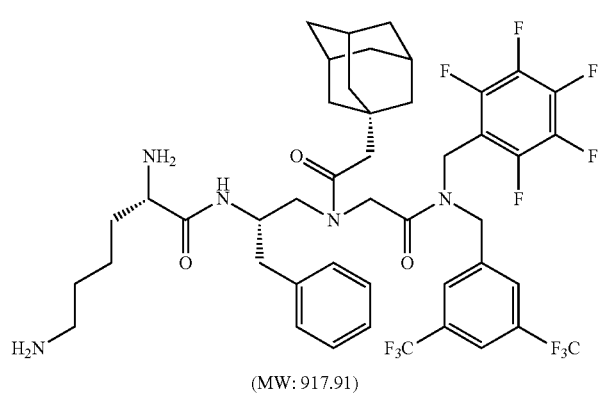
(MW: 917.91)
(45)
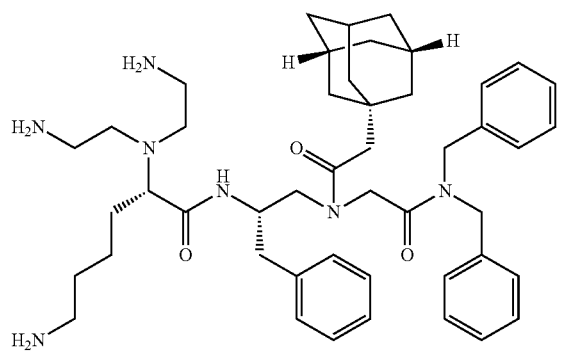
(MW: 778.1)

(46)
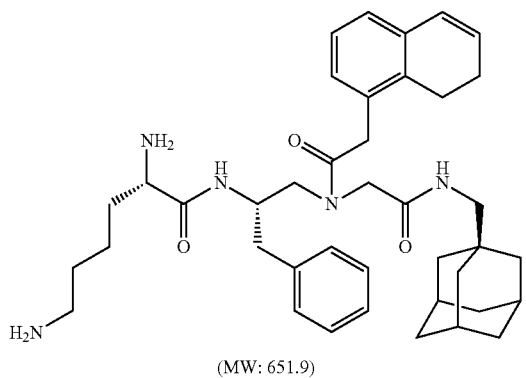
(MW: 651.9)
(47)
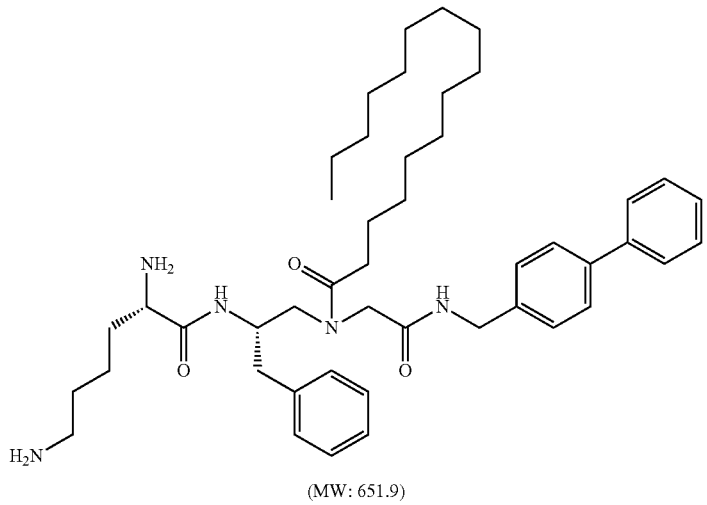
(MW: 651.9)
(48)
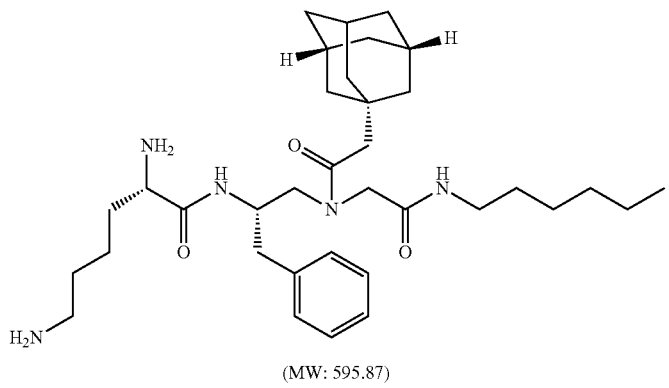
(MW: 595.87)

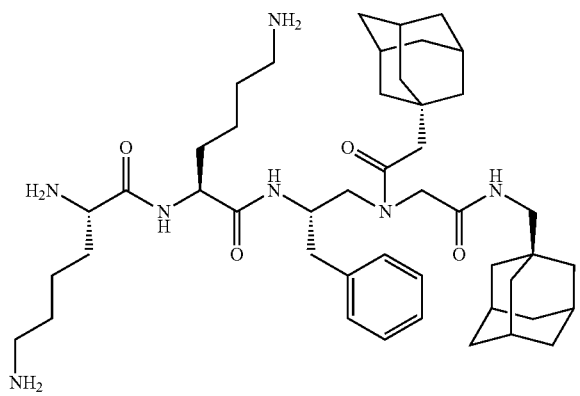

(MW: 788.14)

(49)

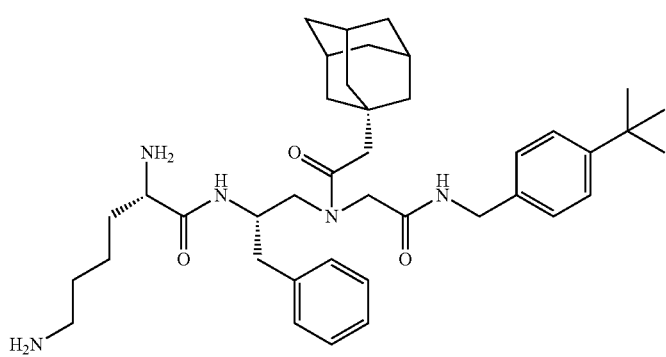

(MW: 657.94)

(50)

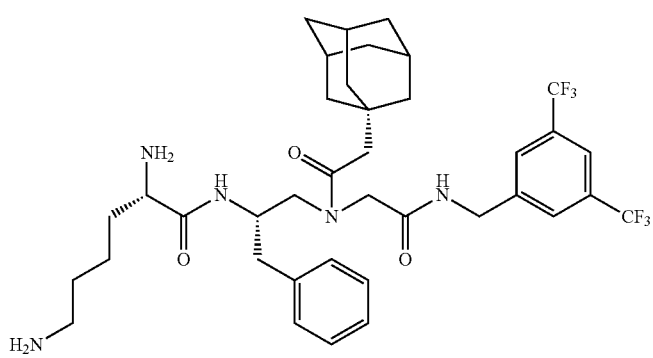

(MW: 737.83)

(51)

In some embodiments, the PTEN binding compound can have a structure according to Formula 1 as described herein. In some embodiments, any one of compounds having a structure according to Formula 1 as described herein, can increase PTEN activity at least 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, to/or 200 percent or more when the compound is present at a concentration of about 1 µM or less.

In some embodiments, the PTEN binding compound can have a structure according to any one of compounds 5, 8, 9, 10, 11, 12, 13, 14, 38, 39, 40, or 43. In some embodiments, any one of compounds 5, 8, 9, 10, 11, 12, 13, 14, 38, 39, 40, or 43 can activate PTEN. In some embodiments, any one of compounds 5, 8, 9, 10, 11, 12, 13, 14, 38, 39, 40, or 43 can increase PTEN activity at least 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, to/or 200 percent or more when the compound is present at a concentration of about 1 µM or less.

In some embodiments, the PTEN binding compound can have a structure according to any one of compounds 15, 16, 17, 19, 20, 21, 24, 25, 26, 27, 32, 33, 34, 35, or 47. In some embodiments, any one of compounds 15, 16, 17, 19, 20, 21, 24, 25, 26, 27, 32, 33, 34, 35, or 47 can inhibit PTEN. In some embodiments, any one of compounds 15, 16, 17, 19, 20, 21, 24, 25, 26, 27, 32, 33, 34, 35, or 47 can inhibit or reduce PTEN activity by 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, to/or 200 percent or more when the compound is present at a concentration of about 1 µM or less.

The PTEN binding compounds can be made using techniques and methods generally known to the skilled artisan in view of this disclosure. Such synthesis schemes are within the scope of this disclosure. An example synthesis scheme is provided in FIG. 4. One of ordinary skill in the art will appreciate modifications to the synthesis scheme in FIG. 4 to generate the compounds described herein and derivatives thereof.

Pharmaceutical Formulations

Also described herein are pharmaceutical formulations that can contain an amount of a compound capable of binding PTEN or an analogue thereof (collectively also referred to herein as a "PTEN binding compound" or "PTEN binding compounds") as described elsewhere herein. Although the terms PTEN binding compound and PTEN binding compounds are used herein to refer to one or more compounds described herein, these terms are not intended to limit the disclosure in any way to any specific functionality of the compounds described herein (e.g. binding or otherwise). The PTEN binding compound can have a structure according to Formula 1 as described elsewhere herein. The PTEN binding compound can be any of compounds (1)-(51). The PTEN binding compounds described herein can be provided to a subject in need thereof alone or as an active ingredient, such as in a pharmaceutical formulation. The pharmaceutical formulation can contain an effective amount of a PTEN binding compounds.

The pharmaceutical formulations described herein can be administered to a subject in need thereof. The subject in need thereof can have a disease or disorder whose pathology involves PTEN. In some embodiments the disease is a cancer occurring in multiple organs. These include all cancers that have compromised PTEN activity or function and all those cancers wherein there is hyperactivity of the PI3K/AKT/mTOR/S6K signaling pathway. The disease can be any disease or disorder involving PTEN or analogue thereof, and/or a ligand of PTEN or analogue thereof. The disease can be one that can be treated and/or prevented by one or more of the compounds and/or formulations described herein. Some diseases include, but are not limited to, all cancers that have compromised PTEN activity or function and all those cancers wherein there is hyperactivity of the PI3K/AKT/mTOR/S6K signaling pathway. An extensive list of all PTEN-related cancers which are included within the scope of this disclosure can be found at the National Institute of Health website. The main malignancies include, but are not limited to, cancers of the breast, prostate, lung, endometrium, head and neck squamous cell carcinoma (HNSCC), ovary, colon, colo-rectal, lymphoma, mesothelioma, salivary gland, testicular cancers, cancers of the thyroid, skin, stomach, soft tissue sarcoma, cancers of the brain including glioblastomas and astrocytomas, aggressive form of skin cancers such as melanomas and head and neck squamous cell carcinomas. More extensive information on PTEN-related cancers can be found National Institute of Health website. Other PTEN-related diseases include, but are not limited to, all of the "PTEN-Opathies" (PTEN hamartoma tumor syndromes (PHTS), Bannayan-Riley-Ruvalcaba syndrome (BRRS), Juvenile polyposis of infancy (JPI), Cowden's syndrome, Hemangiomas, Immune dysregulation, PTEN-related Proteus syndrome (PS), Lhermitte-Duclos disease (LDD), Autism and Autism/pervasive developmental disorder and macrocephaly, Alzheimer's disease, Parkinsonism and metabolic disorders/obesity), which are associated with aberrant PTEN function. (Am J Med Genet C Semin Med Genet. 2013 Apr. 9). The disease can be a disease or disorder that has aberrant PTEN activity. The disease or disorder can include, but is not limited to, TBI (Traumatic Brain injury), neural ischemia, amyotrophic lateral sclerosis (ALS), and other neurodegenerative diseases. The disease or disorder can be one of the corticospinal tract. The disease or disorder can be one induced by injury, including but not limited to, injury to the corticospinal tract. The disease or disorder can be damage to, degeneration of, and/or other loss of axons in the subject. The disease or disorder can be a spinal cord injury.

In some embodiments, the subject can be a human. The term "pharmaceutical formulation'" as used herein also encompasses pharmaceutically acceptable salts of the pharmaceutical formulations and/or active ingredients provided herein.

Pharmaceutically Acceptable Carriers and Auxiliary Ingredients and Agents

The pharmaceutical formulations containing an amount or an effective amount of a PTEN binding compound described herein can further include a pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

In addition to the amount or effective amount of a PTEN binding compound described herein, the pharmaceutical formulation can also include an effective amount of an auxiliary active agent, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, chemotherapeutics, antihypertensives, anticoagulants, antiarrhythmics and different types of bioavailable nanoparticles encapsulating the compounds for optimal delivery.

Effective Amounts of the PTEN Binding Compounds and Auxiliary Agents

The pharmaceutical formulations can contain an effective amount of a PTEN binding compound, and optionally, a therapeutically effective amount of an auxiliary agent. In some embodiments, the effective amount of the PTEN binding compound(s) can range from about 0.3 mg/kg body weight to about 30 mg/kg. The effective amount of the PTEN binding compound(s) can range from about 1 mg to about 10 g. For liquid formulations, some embodiments, the effective amount of the PTEN binding compound(s) or pharmaceutical formulation containing a PTEN binding compound(s) can range from about 10 µL to about 10 mL. One of skill in the art will appreciate that the exact volume will depend on, inter alia, the age and size of the subject, as well as the location of administration. The effective concentration of the PTEN binding compound(s) can range from about 1 nM to 1M.

In embodiments where an optional auxiliary active agent is included in the pharmaceutical formulation, the therapeutically effective amount of the auxiliary active agent will vary depending on the auxiliary active agent. In some embodiments, the therapeutically effective amount of the optional auxiliary active agent can range from 0.001 micrograms to about 1000 milligram. In other embodiments, the therapeutically effective amount of the optional auxiliary active agent can range from about 0.01 IU to about 1000 IU. In further embodiments, the therapeutically effective amount of the auxiliary active agent can range from 0.001 mL to about 1 mL. In yet other embodiments, the therapeutically effective amount of the optional auxiliary active agent can range from about 1% w/w to about 50% w/w of the total pharmaceutical formulation. In additional embodiments, the therapeutically effective amount of the optional auxiliary active agent ranges from about 1% v/v to about 50% v/v of the total pharmaceutical formulation. In still other embodiments, the therapeutically effective amount of the optional auxiliary active agent ranges from about 1% w/v to about 50% w/v of the total pharmaceutical formulation.

Dosage Forms

In some embodiments, the pharmaceutical formulations described herein can be in a dosage form. The dosage forms can be adapted for administration by any appropriate route. Appropriate routes include, but are not limited to, oral (including buccal or sublingual), rectal, epidural, intracranial, intraocular, inhaled, intranasal, topical (including buccal, sublingual, or transdermal), vaginal, intraurethral, parenteral, intracranial, subcutaneous, intramuscular, intravenous, intraperitoneal, intradermal, intraosseous, intracardiac, intraarticular, intracavernous, intrathecal, intravireal, intracerebral, and intracerebroventricular and intradermal. Such formulations can be prepared by any method known in the art.

Dosage forms adapted for oral administration can be discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as foam, spray, or liquid solution. In some embodiments, the oral dosage form can contain about 10 mg to 10 g of a pharmaceutical formulation containing an effective amount or an appropriate fraction thereof of the PTEN binding compound(s). The oral dosage form can be administered to a subject in need thereof by a suitable administration method.

Where appropriate, the dosage forms described herein can be microencapsulated. The dosage form can also be prepared to prolong or sustain the release of any ingredient. In some embodiments, the PTEN binding compound(s) can be the ingredient whose release is delayed. In other embodiments, the release of an optionally included auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, the PTEN binding compound(s), optional auxiliary active ingredient, and/or pharmaceutically acceptable salt thereof can be formulated with a paraffinic or water-miscible ointment base. In other embodiments, the active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, the PTEN binding compound(s), the composition containing the PTEN binding compound(s), auxiliary active ingredient, and/or pharmaceutically acceptable salt thereof in a dosage form adapted for inhalation is in a particle-size-reduced form that is obtained or obtainable by micronization. In some embodiments, the particle size of the size reduced (e.g. micronized) compound or salt or solvate thereof, is defined by a D50 value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active ingredient, which may be generated by various types of metered dose pressurized aerosols, nebulizers, or insufflators.

In some embodiments, the dosage forms are aerosol formulations suitable for administration by inhalation. In some of these embodiments, the aerosol formulation contains a solution or fine suspension of the PTEN binding compound(s) and/or pharmaceutically acceptable salt thereof, and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of the PTEN binding compound(s) or a pharmaceutical formulation thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses or more are delivered each time.

For some dosage forms suitable and/or adapted for inhaled administration, the pharmaceutical formulation is a dry powder inhalable formulation. In addition to the PTEN binding compound(s), an optional auxiliary active ingredient, and/or pharmaceutically acceptable salt thereof, such a dosage form can contain a powder base such as lactose, glucose, trehalose, mannitol, and/or starch. In some of these embodiments, the PTEN binding compound(s), optional auxiliary active ingredient, and/or pharmaceutically acceptable salt thereof is in a particle-size reduced form. In further embodiments, a performance modifier, such as L-leucine or another amino acid, cellobiose octaacetate, and/or metals salts of stearic acid, such as magnesium or calcium stearate can be included.

In some embodiments, the aerosol formulations can be arranged so that each metered dose of aerosol contains a predetermined amount of an active ingredient, such as the one or more of the PTEN binding compound(s) described herein.

Dosage forms adapted for vaginal administration can be presented as pessaries, tampons, creams, gels, pastes, foams, or spray formulations. Dosage forms adapted for rectal administration include suppositories or enemas.

Dosage forms adapted for parenteral administration and/or adapted for any type of injection (e.g. intravenous, intraocular, intraperitoneal, subcutaneous, intramuscular, intradermal, intraosseous, epidural, intracardiac, intraarticular, intracavernous, intrathecal, intravitreal, intracerebral, and intracerebroventricular) can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration or other administration route as appropriate can be presented in a single-unit dose or multi-unit dose containers, including but not limited to sealed ampoules or vials. The doses can be lyophilized and resuspended in a sterile carrier to reconstitute the dose prior to administration. Extemporaneous injection solutions and suspensions can be prepared in some embodiments, from sterile powders, granules, and tablets.

Dosage forms adapted for ocular administration can include aqueous and/or non-aqueous sterile solutions that can optionally be adapted for injection, and which can optionally contain anti-oxidants, buffers, bacteriostats, solutes that render the composition isotonic with the eye or fluid contained therein or around the eye of the subject, and aqueous and non-aqueous sterile suspensions, which can include suspending agents and thickening agents.

For some embodiments, the dosage form contains a predetermined amount of the PTEN binding compound(s) per unit dose. In an embodiment, the predetermined amount of the PTEN binding compound(s) can be an effective amount of the PTEN binding compound(s). In other embodiments, the predetermined amount of the PTEN binding compound(s) can be an appropriate fraction of the effective amount of the active ingredient. Such unit doses may therefore be administered once or more than once a day. Such pharmaceutical formulations can be prepared by any of the methods well known in the art.

Any of the compounds described herein (e.g. a compound having a structure according to Formula I described elsewhere herein, including but not limited to any one of compounds 1-51) can be used as and/or in the manufacture of a medicament for treating a disease or disorder whose pathology includes aberrant or abnormal PTEN activity and/or symptom thereof as described elsewhere herein. Any of the compounds described herein (e.g. a compound having a structure according to Formula I described elsewhere herein, including but not limited to any one of compounds 1-51) can be used as and/or in the manufacture of a medicament for treating a PTEN-opathy and/or symptom thereof as described elsewhere herein. Any of the compounds described herein (e.g. a compound having a structure according to Formula I described elsewhere herein, including but not limited to any one of compounds 1-51) can be used as and/or in the manufacture of a medicament for treating a cancer and/or symptom thereof as described elsewhere herein. In some embodiments, the cancer can be one having compromised PTEN activity and/or function. In some embodiments, the cancer can be one having hyperactivity of PTEN. In some embodiments, the cancer can be a PTEN-related cancer, which are described in greater detail elsewhere herein.

Any of the compounds described herein (e.g. a compound having a structure according to Formula I described elsewhere herein, including but not limited to any one of compounds 1-51) can be for use in treating a disease or disorder whose pathology includes aberrant or abnormal PTEN activity and/or symptom thereof as described elsewhere herein. Any of the compounds described herein (e.g. a compound having a structure according to Formula I described elsewhere herein, including but not limited to any one of compounds 1-51) can be for use in treating a disease or disorder whose pathology includes aberrant or abnormal PTEN activity and/or symptom thereof as described elsewhere herein. Any of the compounds described herein (e.g. a compound having a structure according to Formula I described elsewhere herein, including but not limited to any one of compounds 1-51) can be for use in treating a PTEN-opathy and/or symptom thereof as described elsewhere herein. Any of the compounds described herein (e.g. a compound having a structure according to Formula I described elsewhere herein, including but not limited to any one of compounds 1-51) can be for use in treating a cancer and/or symptom thereof as described elsewhere herein. In some embodiments, the cancer can be one having compromised PTEN activity and/or function. In some embodiments, the cancer can be one having hyperactivity of PTEN. In some embodiments, the cancer can be a PTEN-related cancer, which are described in greater detail elsewhere herein.

Methods of Using the PTEN Binding Compounds and Formulations Thereof

The PTEN binding compounds, derivatives, and formulations thereof provided herein can be used to bind PTEN, increase or enhance PTEN activity (activating PTEN), and/or inhibit or reduce PTEN activity (inhibiting PTEN), and/or treat and/or prevent a disease whose pathology involves a PTEN. In some embodiments the disease is a cancer occurring in multiple organs. These include all cancers that have compromised PTEN activity or function and all those cancers wherein there is hyperactivity of the PI3K/AKT/mTOR/S6K signaling pathway. The disease can be any disease or disorder involving PTEN or analogue thereof, and/or a ligand of PTEN or analogue thereof. The disease can be one that can be treated and/or prevented by one or more of the compounds and/or formulations described herein. Some diseases include, but are not limited to, all cancers that have compromised PTEN activity or function and all those cancers wherein there is hyperactivity of the PI3K/AKT/mTOR/S6K signaling pathway. An extensive list of all PTEN-related cancers which are included within the scope of this disclosure can be found at the National Institute of Health website. The main malignancies include, but are not limited to, cancers of the breast, prostate, lung, endometrium, head and neck squamous cell carcinoma (HNSCC), ovary, colon, colo-rectal, lymphoma, mesothelioma, salivary gland, testicular cancers, cancers of the thyroid, skin, stomach, soft tissue sarcoma, cancers of the brain including glioblastomas and astrocytomas, aggressive form of skin cancers such as melanomas and head and neck squamous cell carcinomas. More extensive information on PTEN-related cancers can be found National Institute of Health website. Other PTEN-related diseases include, but are not limited to, all of the "PTEN-Opathies" (PTEN hamartoma tumor syndromes (PHTS), Bannayan-Riley-Ruvalcaba syndrome (BRRS), Juvenile polyposis of infancy (JPI), Cowden's syndrome, Hemangiomas, Immune dysregulation, PTEN-related Proteus syndrome (PS), Lhermitte-Duclos disease (LDD), Autism and Autism/pervasive developmental disorder and macrocephaly, Alzheimer's disease, Parkinsonism and metabolic disorders/obesity), which are associated with aberrant PTEN function. (Am J Med Genet C Semin Med Genet. 2013 Apr. 9). The disease can be a disease or disorder that has aberrant PTEN activity. The disease or disorder can include, but is not limited to, TBI (Traumatic Brain injury), neural ischemia, amyotrophic lateral sclerosis (ALS), and other neurodegenerative diseases. The disease or disorder can be one of the corticospinal tract. The disease or disorder can be one induced by injury, including but not limited to, injury to the corticospinal tract. The disease or disorder can be damage to, degeneration of, and/or other loss of axons in the subject. The disease or disorder can be a spinal cord injury.

Described herein are methods of activating PTEN that can include the step of contacting PTEN, either in vitro or in vivo, with a PTEN binding compound or formulation thereof provided herein. The PTEN binding compound can be any compound according to Formula 1 described elsewhere herein. In some embodiments of a method of activating PTEN, the PTEN binding compound can be any one or more of compounds 5, 8, 9, 10, 11, 12, 13, 14, 38, 39, 40, or 43. In some embodiments, PTEN activity can be increased by 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, to/or 200 percent or more.

Described herein are methods of inhibiting PTEN that can include the step of contacting PTEN, either in vitro or in vivo, with a PTEN binding compound or formulation thereof provided herein. The PTEN binding compound can be any compound according to Formula 1 described elsewhere herein. In some embodiments of a method of inhibiting PTEN, the PTEN binding compound can be any one or more of compounds 15, 16, 17, 19, 20, 21, 24, 25, 26, 27, 32, 33, 34, 35, or 47. In some embodiments, PTEN activity can be inhibited by 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, to/or 200 percent or more.

Also described herein are methods of treating and/or preventing a disease or symptom thereof in a subject in need thereof that can include the step of administering an amount, such as an effective amount, of one or more PTEN binding compounds to the subject. The disease or disorder can be one whose pathology involves PTEN. In some embodiments the disease is a cancer occurring in multiple organs. These include all cancers that have compromised PTEN activity or function and all those cancers wherein there is hyperactivity of the PI3K/AKT/mTOR/S6K signaling pathway. The disease can be any disease or disorder involving PTEN or analogue thereof, and/or a ligand of PTEN or analogue thereof. The disease can be one that can be treated and/or prevented by one or more of the compounds and/or formulations described herein. Some diseases include, but are not limited to, all cancers that have compromised PTEN activity or function and all those cancers wherein there is hyperactivity of the PI3K/AKT/mTOR/S6K signaling pathway. An extensive list of all PTEN-related cancers which are included within the scope of this disclosure can be found at the National Institute of Health website. The main malignancies include, but are not limited to, cancers of the breast, prostate, lung, endometrium, head and neck squamous cell carcinoma (HNSCC), ovary, colon, colo-rectal, lymphoma, mesothelioma, salivary gland, testicular cancers, cancers of the thyroid, skin, stomach, soft tissue sarcoma, cancers of the brain including glioblastomas and astrocytomas, aggressive form of skin cancers such as melanomas and head and neck squamous cell carcinomas. More extensive information on PTEN-related cancers can be found National Institute of Health website. Other PTEN-related diseases include, but are not limited to, all of the "PTEN-Opathies" (PTEN hamartoma tumor syndromes (PHTS), Bannayan-Riley-Ruvalcaba syndrome (BRRS), Juvenile polyposis of infancy (JPI), Cowden's syndrome, Hemangiomas, Immune dysregulation, PTEN-related Proteus syndrome (PS), Lhermitte-Duclos disease (LDD), Autism and Autism/pervasive developmental disorder and macrocephaly, Alzheimer's disease, Parkinsonism and metabolic disorders/obesity), which are associated with aberrant PTEN function. (Am J Med Genet C Semin Med Genet. 2013 Apr. 9). The disease can be a disease or disorder that has aberrant PTEN activity. The disease or disorder can include, but is not limited to, TBI (Traumatic Brain injury), neural ischemia, amyotrophic lateral sclerosis (ALS), and other neurodegenerative diseases. The disease or disorder can be one of the corticospinal tract. The disease or disorder can be one induced by injury, including but not limited to, injury to the corticospinal tract. The disease or disorder can be damage to, degeneration of, and/or other loss of axons in the subject. The disease or disorder can be a spinal cord injury.

The method can include the step of administering an amount, such as an effective amount of one or more PTEN binding compounds to a subject in need thereof. The subject in need thereof can have a disease or disorder as previously described. In some embodiments, PTEN activity can be increased or decreased after administration of the PTEN binding compound. In some embodiment, the PTEN binding compound can have a structure according to Formula 1 as described elsewhere herein. In some embodiments, the PTEN binding compound can be any one or more of compounds 15, 16, 17, 19, 20, 21, 24, 25, 26, 27, 32, 33, 34, 35, or 47. In some embodiments, PTEN activity can be inhibited by 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, to/or 200 percent or more. In some embodiments, the PTEN binding compound can be any one or more of compounds 5, 8, 9, 10, 11, 12, 13, 14, 38, 39, 40, or 43. In some embodiments, PTEN activity can be increased or enhanced by 1, 2, 3, 4, 5, 6, 7, 8, 9, 10, 12, 15, 20, 25, 30, 35, 40, 45, 50, 55, 60, 65, 70, 75, 90, 85, 90, 95, 100, 125, 150, 175, to/or 200 percent or more.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Introduction

PTEN (Phosphatase and Tensin homolog) is the second most mutated tumor suppressor protein in multiple cancers, after p53 (Yin, Y. & Shen, W. H. PTEN: a new guardian of the genome. Oncogene 27, 5443-5453, doi:10.1038/onc.2008.241 (2008)). Also, PTEN germline mutations cause PTEN Hamartoma Tumor Syndrome (PHTS), including Cowden, Bannayan-Riley-Ruvalcalba and Proteus syndromes (Eng, C. PTEN: one gene, many syndromes. Human mutation 22, 183-198, doi:10.1002/humu.10257 (2003) and Hollander, M. C., Blumenthal, G. M. & Dennis, P. A. PTEN loss in the continuum of common cancers, rare syndromes and mouse models. Nature reviews. Cancer 11, 289-301, doi:10.1038/nrc3037 (2011)). Recently, cerebellum dysplastic hamartoma (Lhermitte Duclos syndrome), juvenile polyposis of infancy, segmental overgrowth and autism spectrum disorder with macrocephaly have been associated with PTEN mutations (Leslie et al., Biochemical Society transactions 44, 273-278, doi:10.1042/bst20150224 (2016)). Conversely, an emerging body of evidence indicates that non-genomic loss of PTEN function via post-transcriptional/translational mechanisms or mislocalization also plays a critical role in pathogenesis of various cancers (Milella, M. et al., Frontiers in oncology 5, 24, doi:10.3389/fonc.2015.00024 (2015), Song, M. S. et al., Molecular cell biology 13, 283-296, doi:10.1038/nrm3330 (2012) and Morotti et al., 2015 Hematol Rep. 2015 Nov. 23; 7(4): 5844. doi: 10.4081/hr.2015.6027). These observations are consistent with the well-established concept of the continuum model put forward by the Pandolfi's group, in which PTEN acts as a rheostat, differentially modulating cellular activity depending upon its levels of expression (Berger A H, Knudson A G, Pandolfi P P. 2011; 476 (7359):163-169.) Reduced PTEN expression indeed confers increased PI3K/AKT activation and may lead to oncogenesis in a given tissue. Thus, every tissue has a defined threshold for PTEN expression, reduction in which leads to cancer (Berger AH, Knudson AG and Pandolfi PP 2011; 476(7359):163-169).

Figure 1B:
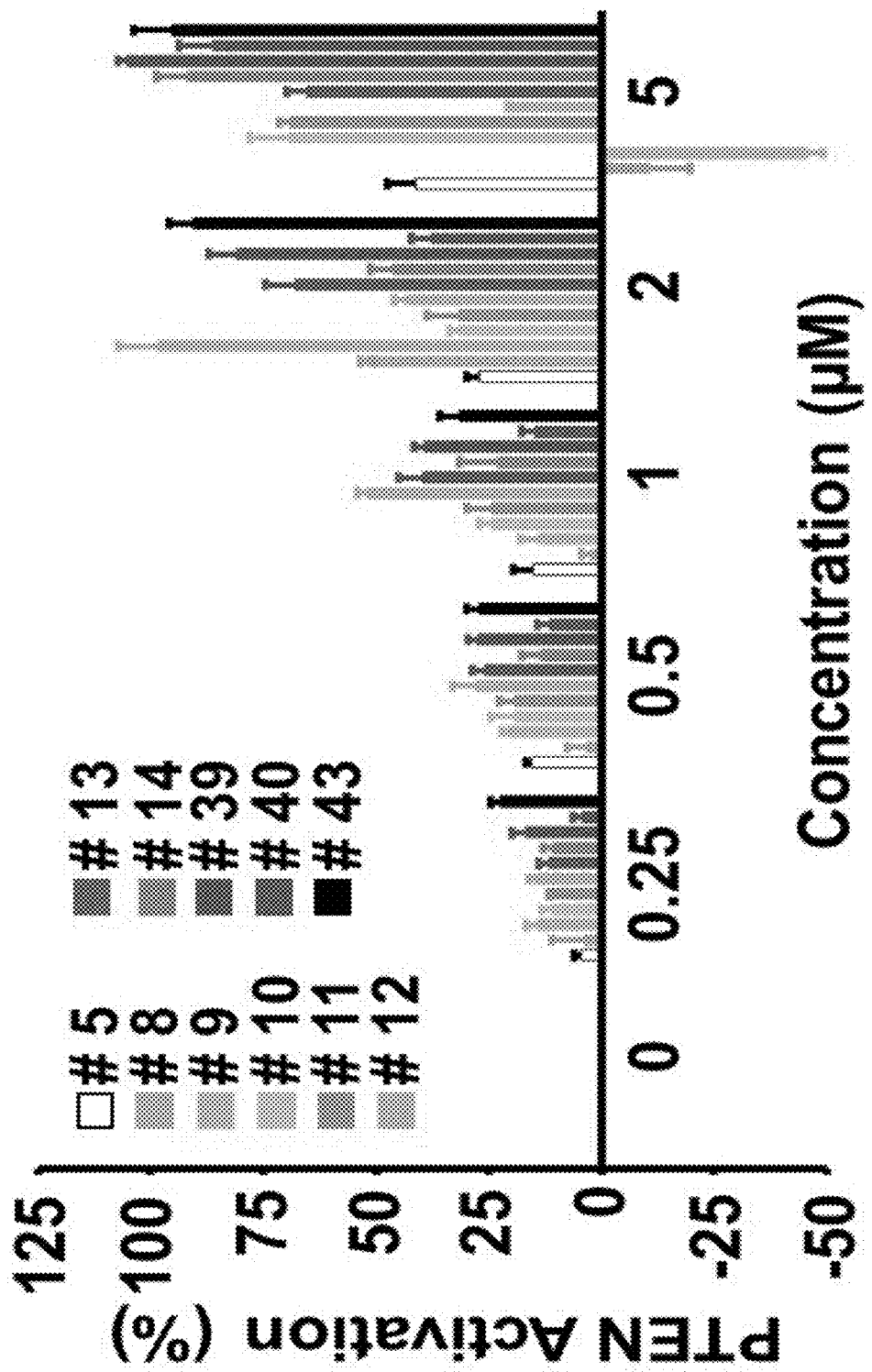

PTEN is a 403 amino acid long dual-specificity (lipid and protein) phosphatase comprising of an N-terminal PIP2 (phosphatidylinositol-4,5-bisphosphate) binding domain (PBD), a catalytic phosphatase domain (PD), a plasma membrane binding C2-domain (C2D) and an intrinsically disordered carboxyl-terminal domain (C-tail) consisting of a PDZ-binding domain (FIGS. 1A-1B). PTEN mainly asserts its tumor suppressive function as a lipid phosphatase, by reducing PIP3 (phosphatidylinositol-3,4,5-triphosphate) levels (Maehama and Dixon 1998, J Biol Chem., May 29; 273(22):13375-8), thereby inhibiting the oncogenic activation of the PI3K/AKT/S6K signaling pathway (Song, M. S. et al., 2012, Molecular Cell Biology 13, 283-296). PTEN regulates cell cycle progression, angiogenesis, cell polarity, apoptosis and metabolism through its lipid and protein phosphatase-dependent and -independent mechanisms (Milella, M. et al., 2015, Frontiers in oncology 5, 24, and Song, M. S. et al., 2012, Molecular cell biology 13, 283-296). Therefore, PTEN is a central molecule, which plays important roles in cellular physiology and homeostasis.

Current therapies for cancers driven by hyperactive PI3K/AKT/S6K pathway include the use of kinase inhibitors targeting one or more kinases. Despite some clinical success with these inhibitors, their benefit has been stymied by off-target effects and drug resistance due to formation of alternative signaling feedback loops (McCubrey, J. A. et al. 2012, Oncotarget 3, 1068-1111, and LoRusso P M J Clin Oncol. 2016 Nov. 1; 34(31):3803-3815). This example explores targeting PTEN to enhance its function, including its phosphatase activity to antagonize PI3K/AKT/S6K signaling and inhibit oncogenic features of tumor progression. Particularly, the upstream position of PTEN in the PI3K/AKT/S6K pathway has the potential to be devoid of complicated feedback loops (Song, M. S. et al., 2012, Molecular cell biology 13, 283-296, and Malaney, P., Uversky, V. N. and Dave, V., 2013, Molecular BioSystems 9, 2877-2888), making it an attractive candidate for developing PTEN-activating compounds.

Aberrant PI3K/AKT/S6K pathway signaling drive cancers by enhancing cell growth, survival, proliferation, migration and invasion, and alter cellular metabolism (Song, M. S. et al., 2012, Molecular cell biology 13, 283-296). PTEN expression can play a role in suppressing this oncogenic potential. Reduced PTEN expression or activity is observed in various cancers and neurological diseases [Hopkins B. D et al., 2014, Trends in biochemical sciences 39, 183-190] and currently there are no known molecules that directly activate PTEN function (Malaney, P., Uversky, V. N. and Dave, V., 2013, Molecular BioSystems 9, 2877-2888). This Example also can demonstrate characterization and functional elucidation of a novel group of peptidomimetics, previously described as γ-AAPeptides [Niu Y., et al., 2011, New J. Chem 35:542-545] that can activate the lipid phosphatase function of PTEN in vitro and reduce the oncogenic potential of cancer cells in vivo are demonstrated. PTEN activation via γ-AAPeptides reduced the activity of the canonical PI3K/AKT/S6K oncogenic pathway, inhibited proliferation and migration and caused cell cycle arrest in the G1-phase of lung cancer cells, demonstrating their potential as an anti-cancer agent. Therefore, the family of γ-AAPeptides described herein can offer a unique therapeutic entrée for targeting the oncogenic PI3K/AKT/S6K signaling pathway often implicated in cancer progression.

Results

Figure 4:
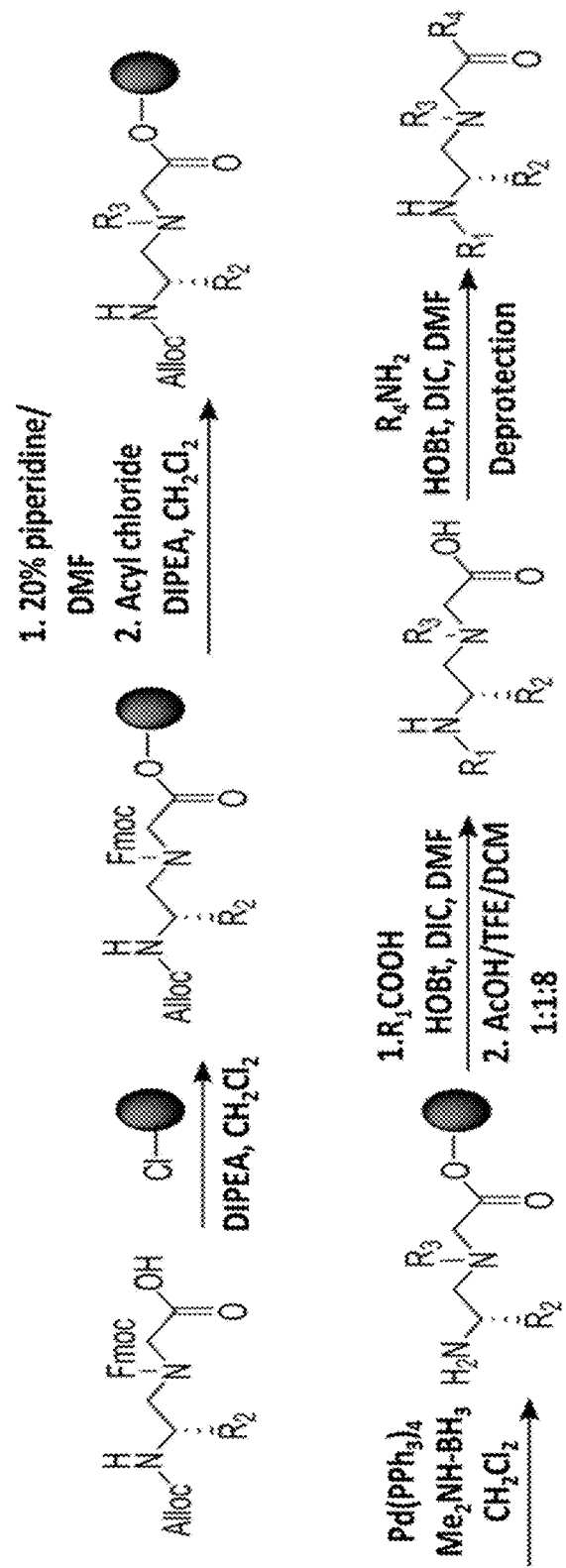
FIG. 4 shows a synthesis scheme of γ-AAPeptides that are capable of activating (or inhibiting) PTEN. Peptides can be synthesized directly from the N-acylated-N-aminoethyl amino acid building block harboring the $R_2$ side chain. The building block can be attached to a chloro-trityl resin, and $R_1$, $R_3$, and $R_4$ side chains can be sequentially added after deprotection, as shown above, and ultimately cleaved from the resin to give the final structure.

Fifty non-natural peptidomimetics (γ-AApeptides) mimicking bioactive peptides were synthesized from the previously described N-acylated-N-aminoethyl amino acid building block (Niu Y., et al., 2011, New J. Chem 35:542-545). Briefly, the building block, already containing the $R_2$ side chain, undergoes de-protection before addition of the $R_3$ and $R_1$ side chains. After cleavage of this intermediate from the solid phase, the $R_4$ group was added to the C-terminus, completing the synthesis (FIG. 4).

γ-AAPeptides were screened using the colorimetric-based Malachite Green phosphatase assay (Itaya, K. and Ui M., 1966, Clinica chimica acta; international journal of clinical chemistry 14, 361-366]) as a measure of PTEN lipid phosphatase activity, with soluble diC8PIP3 (dioctanoyl-phosphatidylinositol-3,4,5-P3) as the PTEN substrate. Eleven peptidomimetics were observed to increase PTEN lipid phosphatase activity at about a 1 μM concentration (FIG. 1A). Further, in the presence of PIP3, titration of these 11 γ-AAPeptides revealed an increase in PTEN lipid phosphatase activity with increasing concentration (FIG. 1B) as compared to PTEN with buffer alone. All 11 γ-AAPeptides harbored an adamantyl group at position $R_3$, an aromatic functional group as the $R_2$ side chain and a hydrophilic chain in position $R_1$ (FIG. 5). Purity of these γ-AAPeptides was verified by High-Resolution Mass Spectroscopy (H-RMS) and Nuclear Magnetic Resonance (NMR) spectroscopy analysis. In accordance with the data from the titration assays, the two most promising γ-AAPeptides, compounds (43) (also depicted as #43) and #9, were chosen to ascertain the in vivo effect on molecular signaling and cell physiology utilizing lung cancer cells.

Figure 2A:
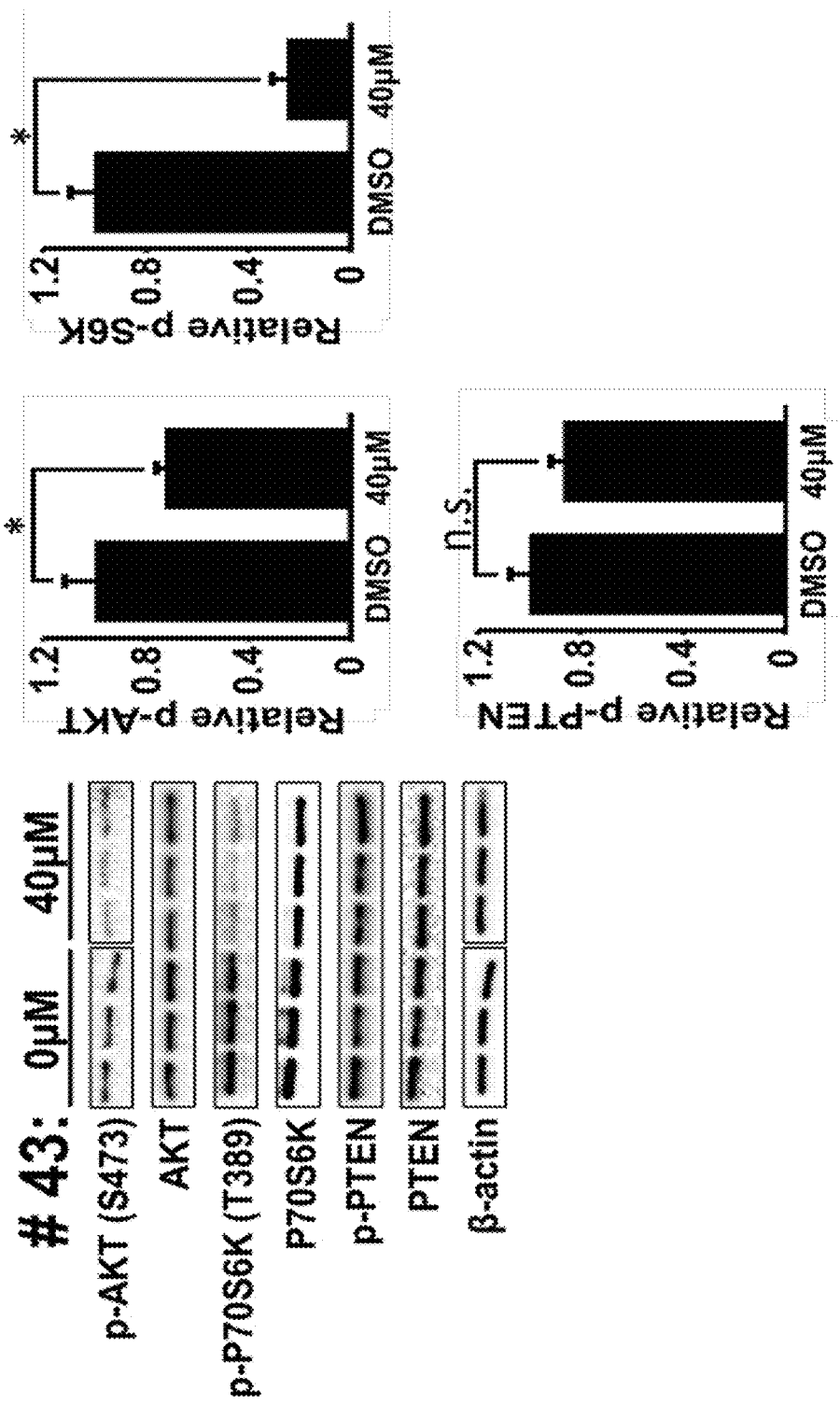
FIGS. 2A-2B show results demonstrating γ-AA Peptides 43 and 9 induce PTEN lipid phosphatase activity.
Figure 2B:
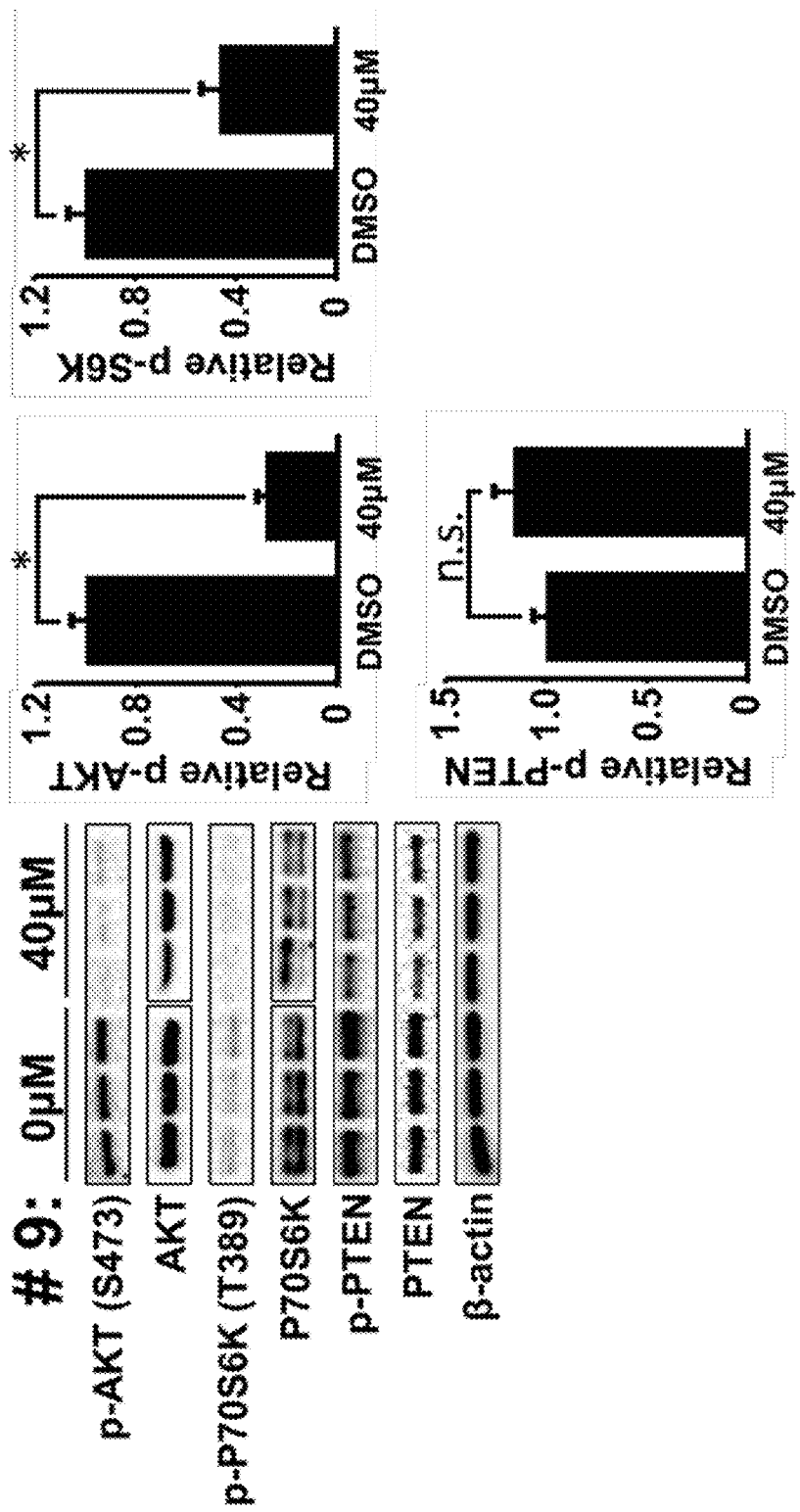

PTEN antagonizes PI3K/AKT/S6K pathway activation via its lipid phosphatase function (Stambolic et al., 1998, Cell, October 2; 95(1):29-39, Sun H., et al., 1999, Proc Natl Acad Sci USA. 1999 May 25; 96(11):6199-204 and Song, M. S. et al., 2012, Molecular Cell Biology 13, 283-296). A549 lung adenocarcinoma cells were treated with either γ-AAPeptide #43 or #9 for 6 hours to determine the activity of PI3K/AKT/S6K downstream pathway effectors. There was about a 30 percent and about 70 decrease in the phosphorylated, active form of AKT (pAKT-Ser473) upon treatment with 40 μM γ-AAPeptide #43 (FIG. 2A) or about 40 μM γ-AAPeptide #9 (FIG. 2B) respectively. Likewise, treatment with γ-AAPeptides #43 (FIG. 1B) and #9 (FIGS. 2A and 2B) drastically reduced phosphorylated, active form of P70S6K (p-P70S6K-Thr389) levels by about 75 percent and about 55 percent respectively, indicating that these compounds likely activated endogenous cellular PTEN, which reduced the canonical PI3K/AKT/S6K signaling. Interestingly, these compounds did not appear to alter phosphorylation status of the PTEN C-terminus (C-tail) cluster (Ser380, Thr382, Thr383, Ser385) following treatment with about 40 μM #43 or #9 (FIGS. 2A and 2B) PTEN C-tail phosphorylation via multiple kinases renders PTEN inactive (Randar 2009, Malaney Sci Reports), therefore it is unlikely that the γ-AAPeptides activate PTEN via modulation of C-tail phosphorylation by multiple kinases. However, direct allosteric effects of these compounds on the structure and catalytic function of the PTEN enzyme activity remains highly plausible. Taken together, these results suggest that the γ-AAPeptides enhance PTEN lipid phosphatase activity in vitro, and antagonize the PI3K/AKT/S6K pathway in vivo.

Figure 3A:
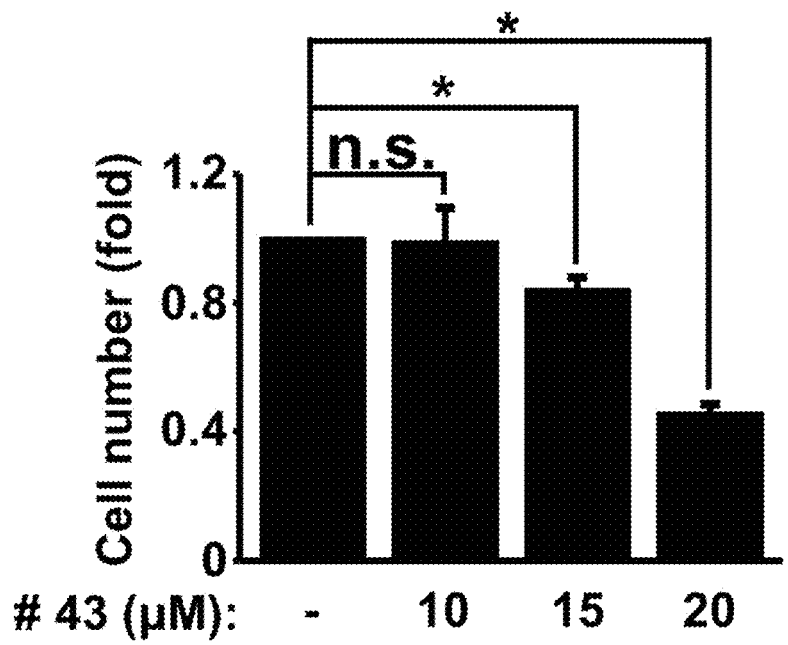
FIGS. 3A-3F show graphs demonstrating inhibition of cell proliferation and migration by γ-AAPeptides 43 and 9 inhibit cell proliferation and migration.
Figure 3B:
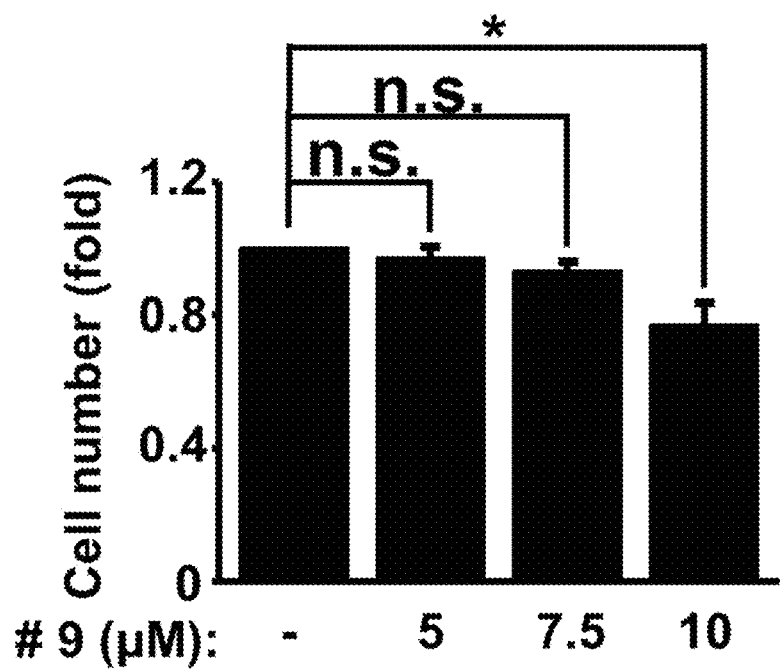
Figure 3C:
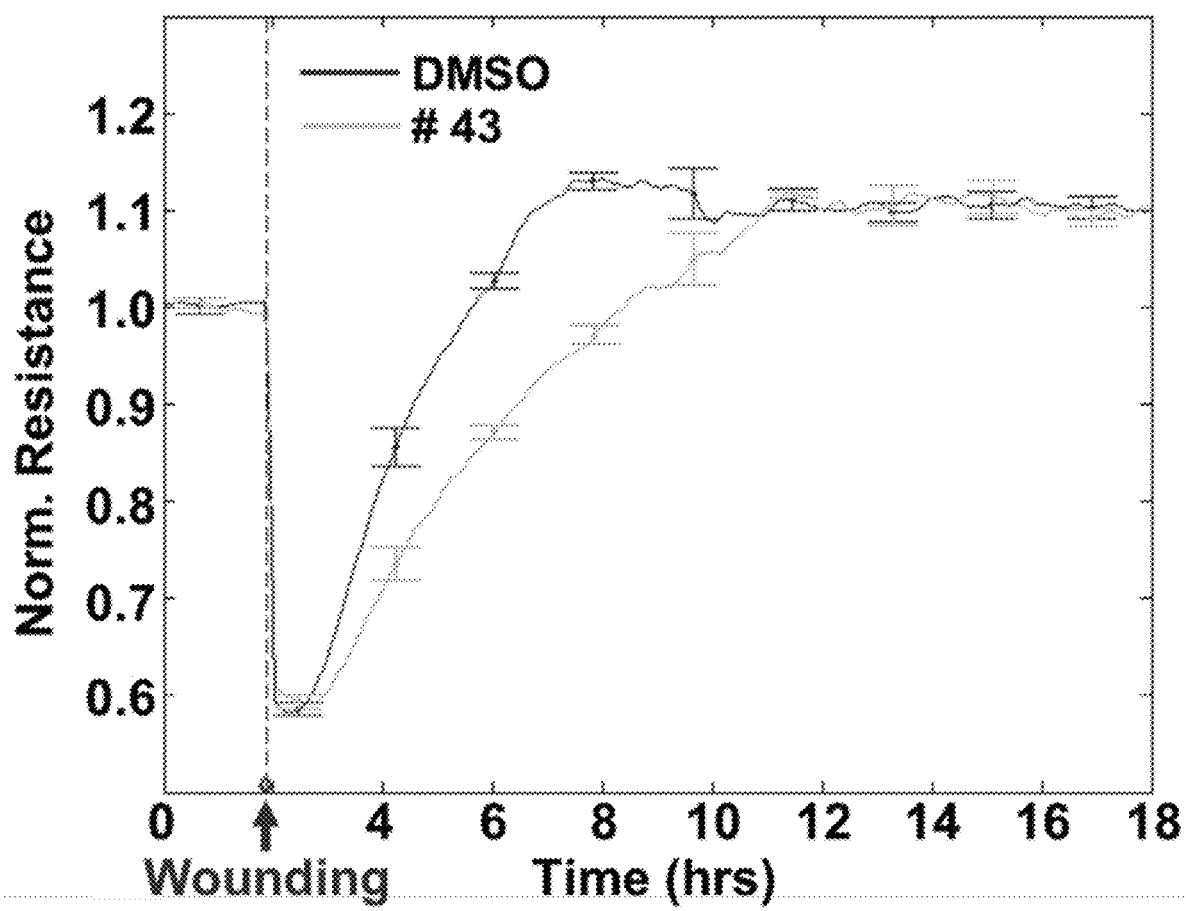
Figure 3D:
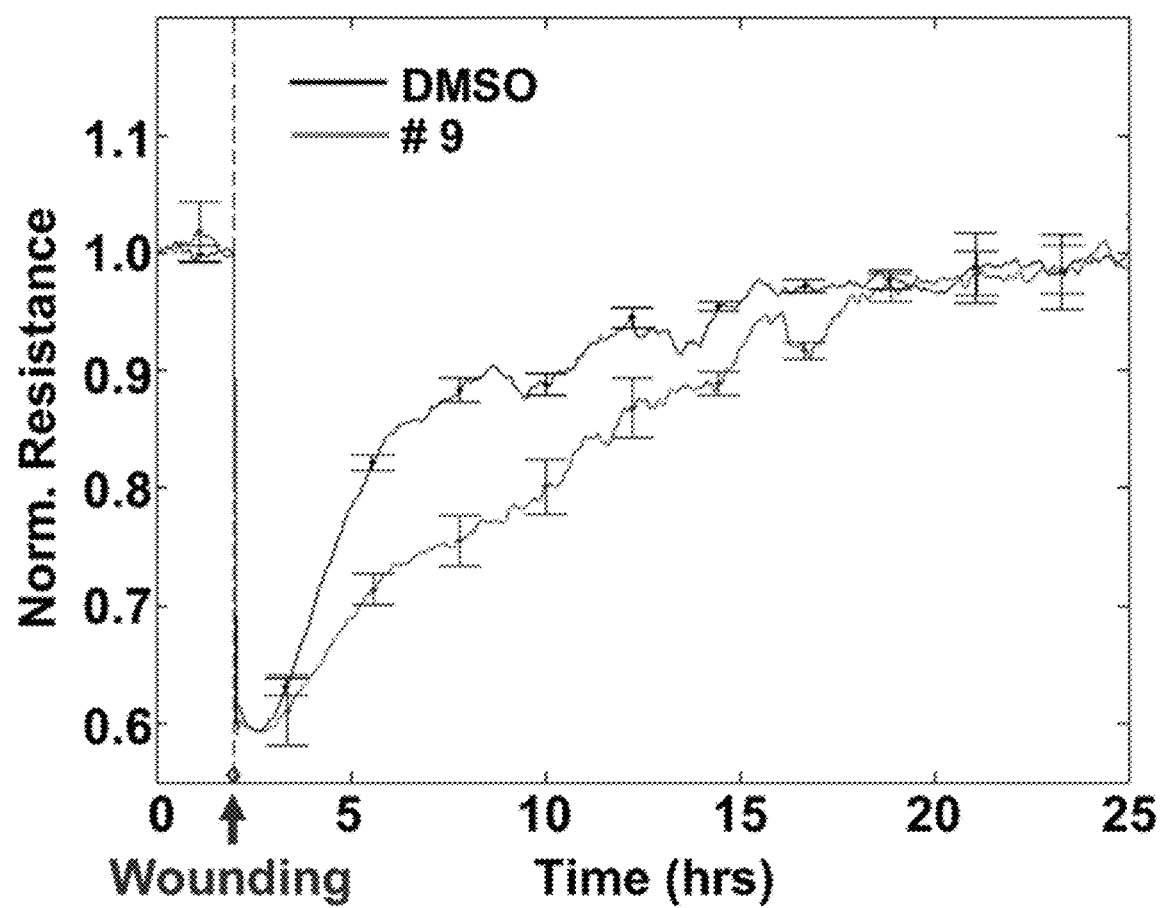
Figure 3E:
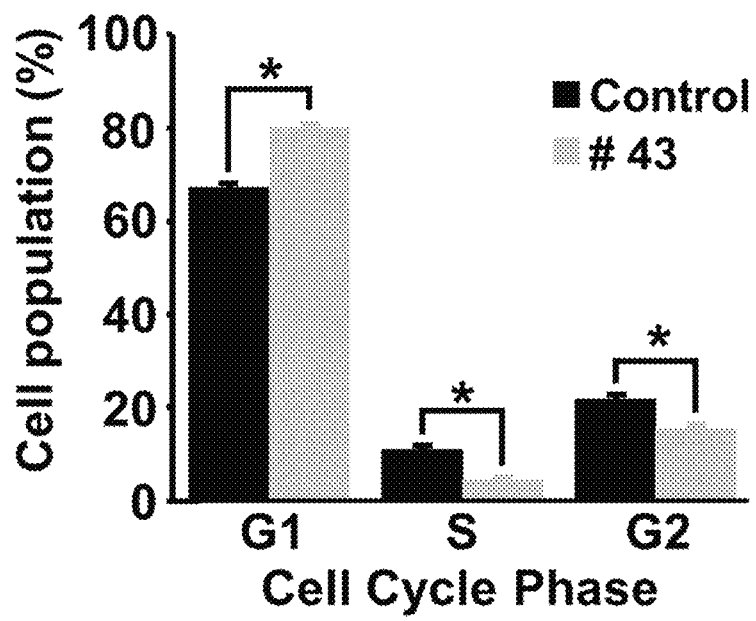
Figure 3F:
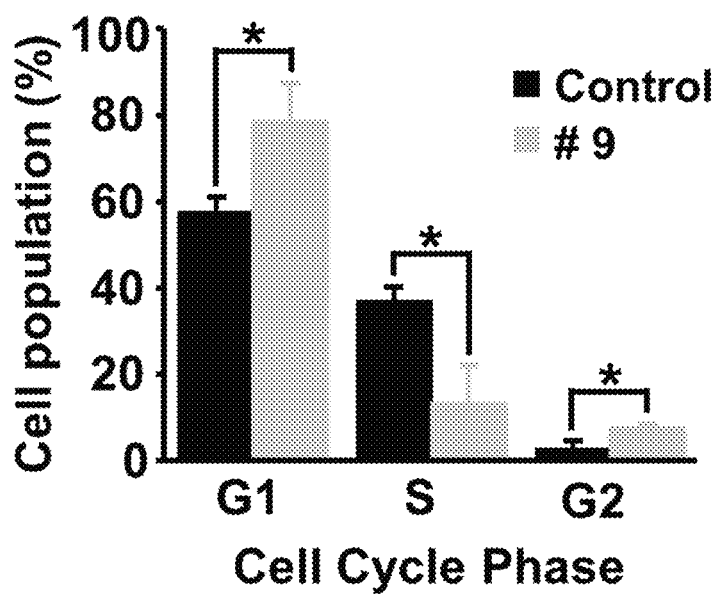

Both γ-AAPeptide #43 (FIG. 3A) and #9 (FIG. 3B) reduced A549 cell proliferation in a dose dependent manner, indicating that the γ-AAPeptides can have a direct biological and/or physiological effect. This was further supported by the lung cancer cell-migration studies using the Electric Cell-substrate Impedance Sensing (ECIS) method. These ECIS studies demonstrated the ability of γ-AAPeptides #43 and #9 to inhibit cell migration. (FIGS. 3C and 3D). PTEN inhibits cell proliferation by inducing cell cycle arrest at the G1 and G2/M transition phases (Da-Ming Li and Hong S., 1998, PNAS 1998 December, 95; (26):15406-15411 and Kim, S. J., 2016, Oncogene. Jan., 14; 35(2):251-60). Flow cytometry was then used to assess the effect of the γ-AAPeptides on the cell cycle. As compared to vehicle treated cells, γ-AAPeptide #43 was observed to arrest cells in G1 phase after 24 hour treatment, (note the increase in G1 phase and a decrease in S phase cell population; FIG. 3E). Likewise, γ-AAPeptide #9 arrested the cell cycle in both G1 and G2 phases after 24-hour treatment (FIG. 3F). These results can indicate that the γ-AAPeptides are potent inhibitors of well-known oncogenic activities, including cell proliferation and migration and are able to arrest the cell cycle. In summary, 11 peptidomimetics were identified that induce PTEN lipid phosphatase activity and defined two most optimal γ-AAPeptides that reduce the oncogenic potential of cancer cells. Protein:γ-AAPeptide interaction at the PD/C2D interface may induce a conformational change in PTEN protein structure, increasing the accessibility of the PTEN catalytic pocket to PIP3. Alternatively, allosteric changes in PTEN molecule by γ-AAPeptide may increase the affinity for PIP3, contributing to its rapid (about 2 fold increase) degradation to PIP2. As per the recent evidence, the possibility exists that the γ-AAPeptides can promote PTEN homodimer formation in vitro by promoting a higher order structure with allosteric interactions, thus influencing catalytic lipid phosphatase activity (Papa et al. 2014, Cell, April 24; 157(3):595-610). PTEN:γ-AAPeptide co-crystallization studies will elucidate the definitive protein:γ-AAPeptide interactions and provide a potential mechanistic insight into how our γ-AAPeptides elicit their tumor suppressive effects through PTEN. These γ-AAPeptides can be a therapeutic option for cancer and other patients with hyperactivated PI3K/AKT/S6K pathway, those containing PTEN mutations or for patients with diseases associated with compromised PTEN function, activity and/or decreased PTEN expression. γ-AAPeptide based adjunctive therapy can be used to treat diseases driven by compromised PTEN functions.

FIG. 5 shows a table demonstrating example γ-AAPeptide Side Chain Structures. FIG. 5 provides a visual representation of the 4 R-group side chains for each γ-AA Peptide. R-groups are added to the N-acylated-N-aminoethyl backbone, as previously described. FIG. 6 shows example small molecule compounds that are capable of enhancing PTEN activity.

Figure 7:
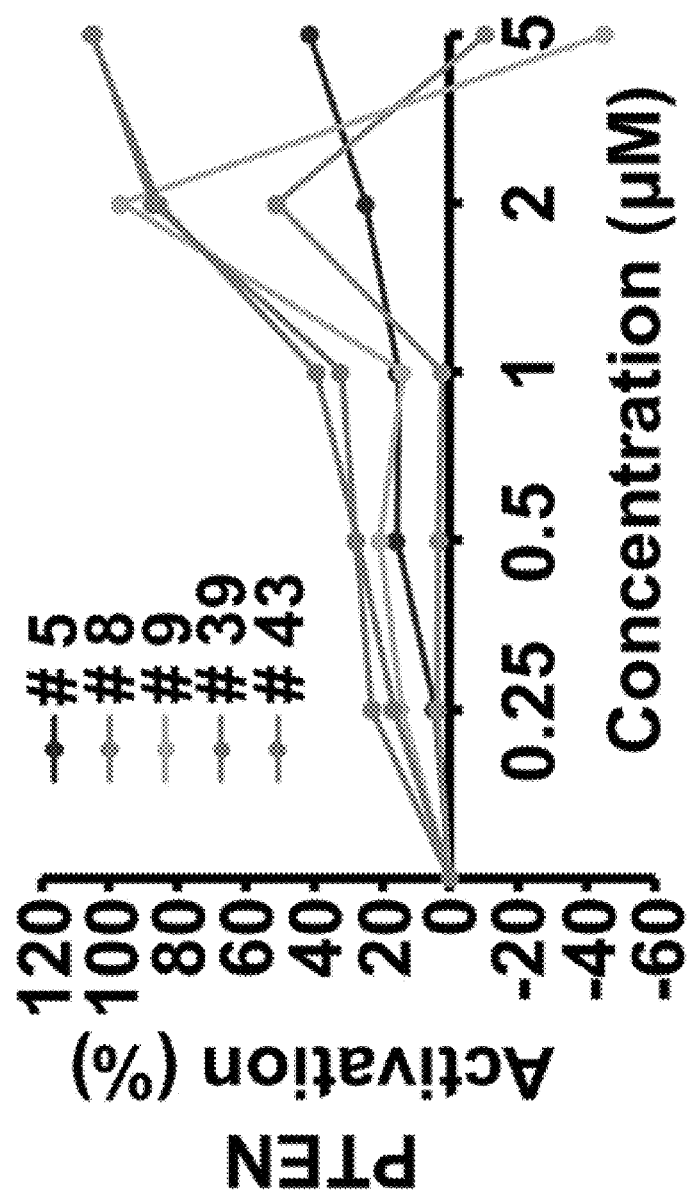
FIG. 7 shows a graph demonstrating Titration curves for 5 of 11 γ-AA Peptides. A Malachite Green assay was used to determine PTEN lipid phosphatase activity with and without the presence of indicated γ-AA Peptide, n=4. Standard error bars are too small to be seen.

FIG. 7 shows a graph demonstrating Titration curves for 5 of 11 γ-AA Peptides. A malachite Green assay was used to determine PTEN lipid phosphatase activity with and without the presence of indicated γ-AA Peptide, n=4. Standard error bars are too small to be seen.

Figure 8:
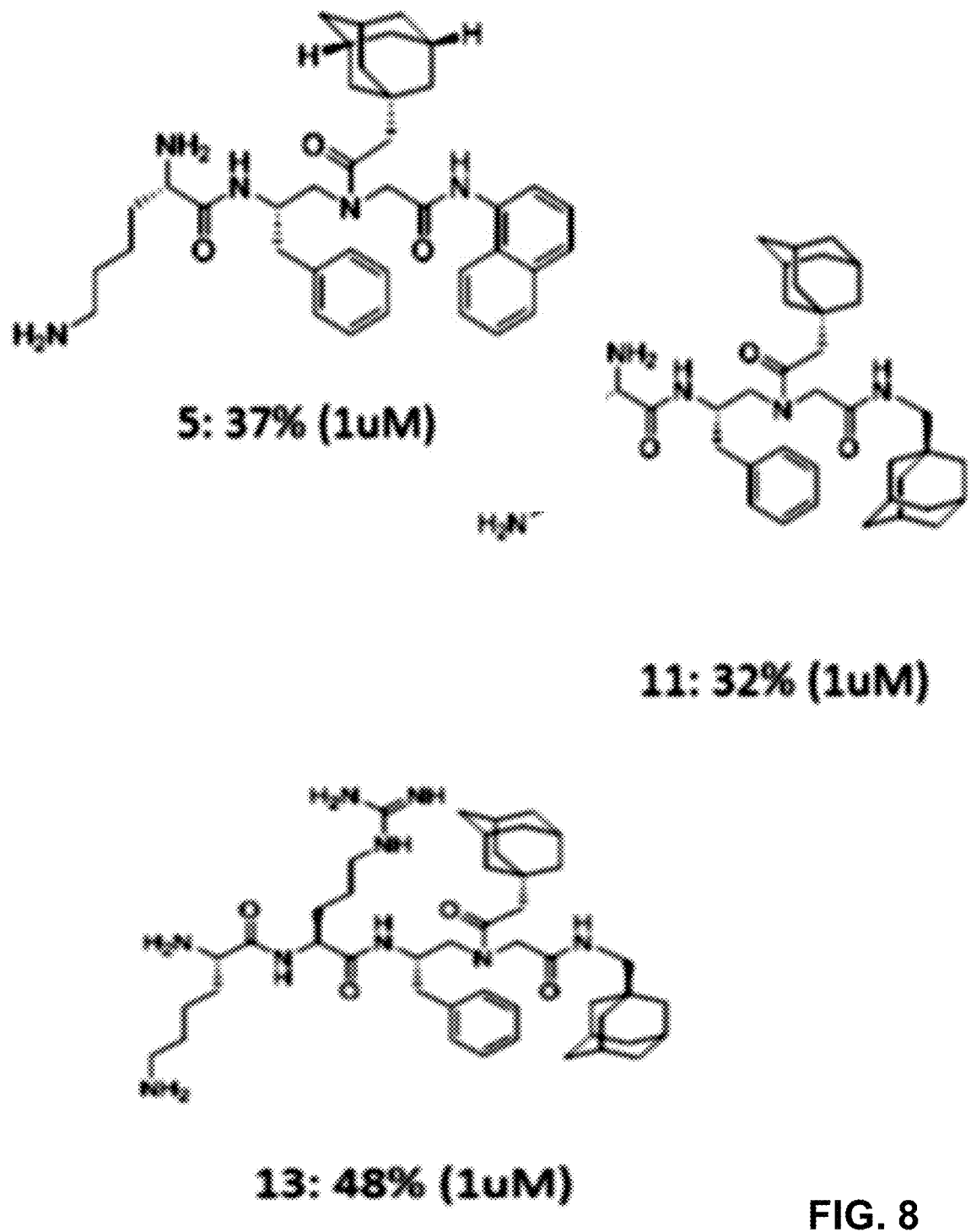
FIG. 8 shows a table demonstrating example small molecule compounds that are capable of activating PTEN activity.

FIG. 8 shows a table demonstrating example small molecule compounds that are capable of activating PTEN activity.

Materials and Methods

γ-AApeptide Synthesis. Fifty non-natural peptidomimetics (γ-AApeptides) mimicking bioactive peptides were synthesized from N-acylated-N-aminoethyl amino acid building blocks, synthesized as previously described (Niu Y., et al., 2011, New J. Chem 35:542-545). The building block harboring the $R_2$ side chain was attached to a chloro-trityl resin. The sequential addition of $R_3$ and $R_1$ side chains occurred after deprotection steps. After cleavage of this intermediate from the solid phase, the $R_4$ group was added to the C-terminus, completing synthesis. γ-AAPeptide purity was verified by High-Resolution Mass Spectroscopy (H-RMS) and Nuclear Magnetic Resonance (NM R) spectroscopy analysis.

Lipid Phosphatase Assays. PTEN lipid phosphatase activity was examined using a Malachite Green (MG) screening assay. First, 16.67 ng of pure recombinant PTEN protein produced in SF9 insect cells (Cayman Chemical, Ann Arbor, Mich.) was incubated with about 50 mM Tris HCl, pH 8.0, about 100 mM NaCl, about 5 mM DTT and increasing amount of indicated γ-AAPeptide (about 0, about 0.25, about 0.50, about 1, about 2, and about 5 μM) for about 1 hour at about 37° C. in a 96-well microtiter plate. Second, a water soluble diC8-PI(3,4,5)P3 substrate (Echelon Biosciences, Salt Lake City, Utah) was added in each well and the reaction continued for additional 90 minutes at about 37° C. Third, at about 195 μL MG-reagent (Echelon Biosciences, Salt Lake City, Utah) was added to each well and allowed to incubate for additional 20 min at room temperature to allow for color development. Absorbance was measured at about 620 nm and phosphate released was calculated from the standard curve. Assays were performed in quadruplets and reported as mean±S.E.

Cell Culture Maintenance. A549 cells (ATCC® CRM-CCI-185™, Manassas, Va.) were cultured in F12K media (Thermo Fisher, Waltham, Mass.) supplemented with 10% Fetal Bovine Serum (FBS), Antibiotic-antimycotic solution (final concentration about 200 units/mL penicillin G, about 200 μg/mL streptomycin sulfate and about 0.5 μg/mL amphotericin B, Sigma Aldrich, St. Louis, Mo.) and Plasmocin (about 1.25 μg/mL, Invitrogen, San Diego, Calif.). Cells were maintained in a about 5% $CO_2$ humidified incubator at about 37° C.

Protein Isolation and Immuno-blotting. For treatment with γ-AAPeptides, A549 cells were grown to about 50-60% confluency in 6-well plates, treated with indicated amount of γ-AAPeptide and allowed to incubate for 6 hours at about 5% $CO_2$ and 37° C. After about 6 hours, media was aspirated and cells were lysed in ice cold IP Lysis Buffer (25 mM Tris-HCl pH 7.4, about 150 mM NaCl, about 1% NP-40, about 1 mM EDTA, about 5% glycerol) supplemented with about 100× protease inhibitor cocktail (Sigma Aldrich, St. Louis, Mo.), phosphatase inhibitor cocktail (final concentration about 10 mM sodium azide, about 10 mM NaF, about 4 mM sodium orthovanadate, about 10 mM sodium-molybdate dehydrate, about 4 mM sodium-tartrate dibasic dehydrate, about 5 mM EDTA disodium dehydrate, about 2 mM imidazole), about 1 mM DTT and about 1 mM PMSF. Samples were sonicated at about 10% amplitude on a digital sonifier (Branson Ultrasonics, Dabury, Conn.), centrifuged at about 14,000 rpm for about 10 minutes and the supernatant was collected. Protein concentration was determined using Bradford Dye Reagent (BioRad, Hercules, Calif.). The remaining supernatant was boiled in about 100 μL of 2× Laemmli Buffer containing about 5% β-mercaptoethanol (Sigma Aldrich, St. Louis, Mo.) and subjected to SDS-PAGE gel analysis, followed by immunoblotting. About 20 μg of total proteins from A549 cell extract were separated on a about 12% SDS-PAGE gel and electro-blotted to nitrocellulose membranes (about 0.45 μm; GE Healthcare, Pittsburgh, Pa.). Blots were blocked with about 5% nonfat dry milk or bovine serum albumin in TBST buffer (about 10 mM Tris, pH about 8, about 150 mM NaCl, about 0.1% Tween 20) and incubated with indicated primary antibodies (Table 1). Peroxidase conjugated mouse or rabbit secondary antibodies were used at dilution of about 1:10,000 (Jackson ImmunoResearch, West Grove, Pa.). Blots were developed by chemiluminescence (Thermo Fisher Scientific, Waltham, Mass.) and developed on a Chemidoc MP System (BioRad, Hercules, Calif.). Assays were performed in triplicate. Densitometry on the immunoblots are reported as mean±S.E. (p value of ≤0.05 was considered to be significant).

TABLE 1

| Primary Antibody | Concentration | Company |
| --- | --- | --- |
| p-AKT Ser473 | 1:2000 Dilution | Cell Signaling Technologies, Danvers, MA |
| AKT | 1:1000 Dilution | Cell Signaling Technologies, Danvers, MA |
| p-P70S6K Thr389 | 1:2000 Dilution | Cell Signaling Technologies, Danvers, MA |
| P70S6K | 1:1000 Dilution | Cell Signaling Technologies, Danvers, MA |
| p-PTEN | 1:2000 Dilution | Cell Signaling Technologies, Danvers, MA |
| PTEN Ser380, Thr382/383 | 1:1000 Dilution | Cell Signaling Technologies, Danvers, MA |
| B-actin | 1:1000 Dilution | Sigma-Aldrich, St. Louis, MO |

Proliferation Assays. Cell proliferation studies were performed using the Cell Counting Kit-8 (Dojindo Molecular Technologies, Rockville, Md.). A549 cells were plated in a 96-well plate with a cell density of about 9000 cells/well and cultured in F12K medium as described above. Cells were treated with indicated amount of γ-AAPeptide diluted in F12K media for 24 hours. After 24 hours, final cell numbers were assessed as a function of absorbance at 450 nm of reduced WST-(2-(2-methoxy-4-nitrophenyl)-3-(4-nitrophenyl)-5-(2,4-disulfophenyl)-2H-tetrazolium, monosodium salt).

Migration Assay. Migration assay was performed on the ECIS machine (Name, Address). Briefly, A549 cells were grown on electric cell substrate impedance sensing 8-well plate arrays (8W1E; Applied Biophysics, Troy, N.Y.) in F12K media as described above. Confluent cells were treated with media containing γ-AAPeptide at desired concentration for about 12 hours prior to wounding. Cells were wounded using an elevated field pulse of about 1400 mA at about 32,000 Hz applied for about 20 seconds, producing a uniform circular lesion of about 250 mm in size, and wound closure was tracked until healing. The impedance (Z) was measured at about 32000 Hz, normalized to its value at the initiation of data acquisition, and plotted as a function of time. Assays were performed in triplicate and reported as mean±S.E. unless stated otherwise (p value of ≤0.05 was considered to be significant).

Flow Cytometry Assay for Cell Cycle Analysis. Cell cycle analysis was performed on A549 cells treated with indicated amount of γ-AAPeptide at about 50-60% confluency for about 24 hours. After about 24 hours of indicated γ-AAPeptide treatment, cells were trypsinized and centrifuged at about 2,000 rpm for about 10 minutes. Media and trypsin were aspirated and cells were washed twice with PBS and spun at about 2,000 rpm for about 10 minutes at about 4° C.

after each wash. Cells were then stained with trypan blue (Thermo Fisher Scientific, Waltham, Mass.) and counted using a hemocytometer. Cells were resuspended in Phosphate Buffered Saline (PBS) at a density of about 2×106 cells/mL. 1 mL of cells was fixed in about 3 mL ice cold absolute ethanol for about 1 hour at about 4° C. After fixing, cells were washed twice with PBS and spun at about 3,000 rpm for about 10 minutes at about 4° C. after each wash. About 1 mL of Propidium Iodide (PI) staining solution (about 3.8 mM sodium citrate, about 40 µg/mL PI and PBS to volume) was added to each cell pellet, along with about 50 µL of RNase A (Qiagen, Hilden, Germany) at a concentration of about 10 µg/mL. Cells were incubated at about 37° C. for about 20 minutes and sub-sequentially stored at 4° C. until analyzed by flow cytometry. Assays were performed in triplicate and reported as mean±S.E. (p value of ≤0.05 was considered to be significant).

Example 2

The compound can that can bind PTEN can inhibit PTEN activity. FIG. 9 shows example small molecule compounds that can be capable of inhibiting PTEN activity.

We claim:
1. A pharmaceutical formulation comprising:
A compound having a structure according to Formula 1

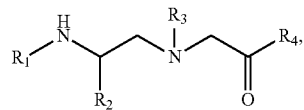

Formula 1 where $R_1$ is H,

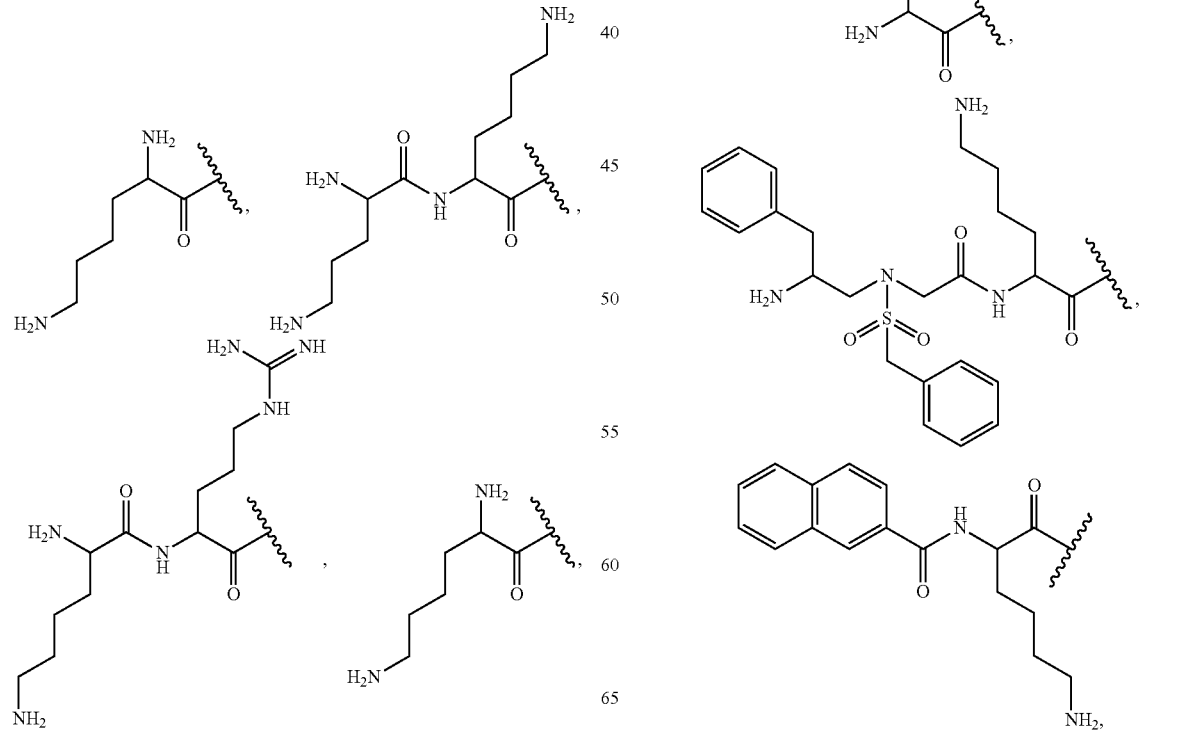

95
-continued
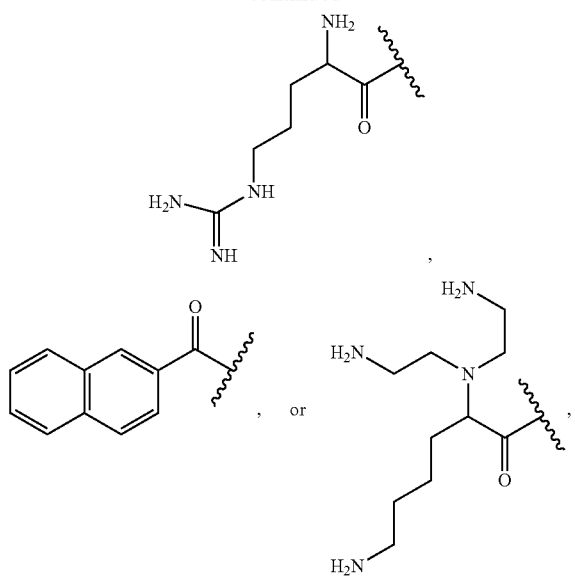
where R₂ is
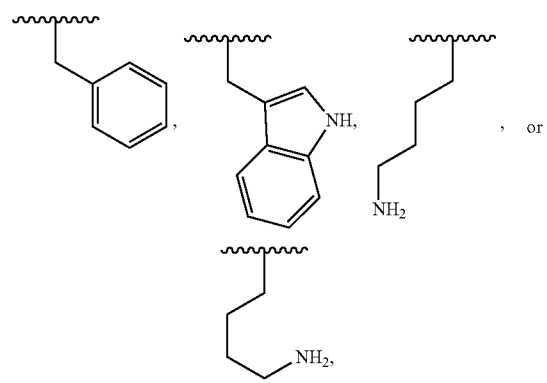
where R₃ is
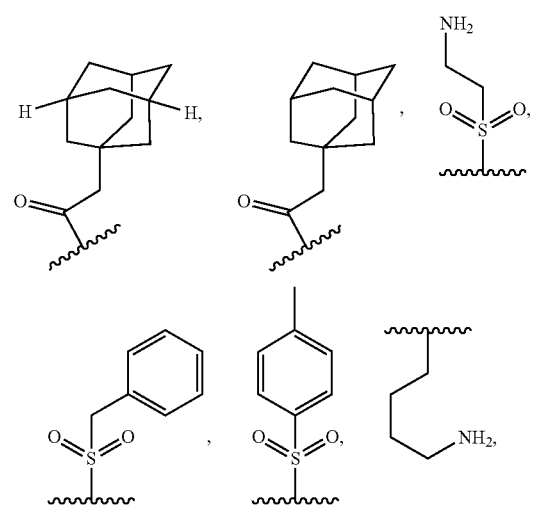
96
-continued
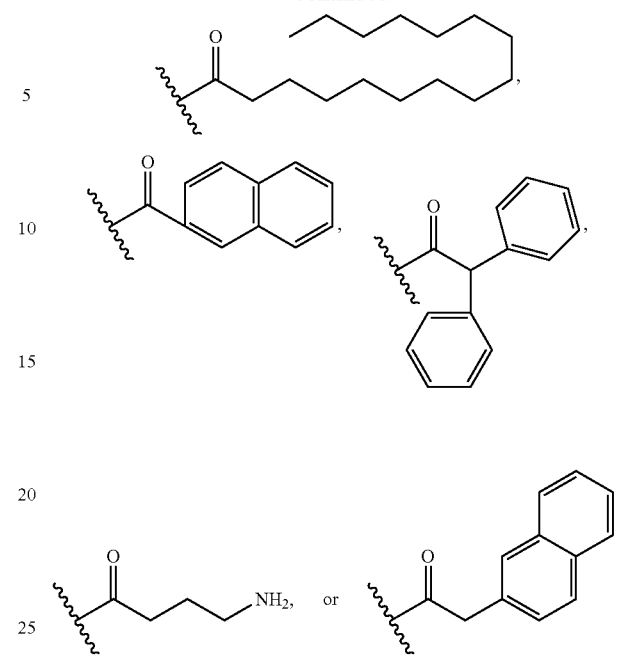
where R₄ is
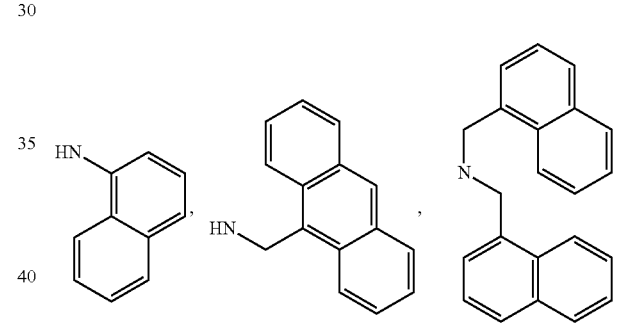
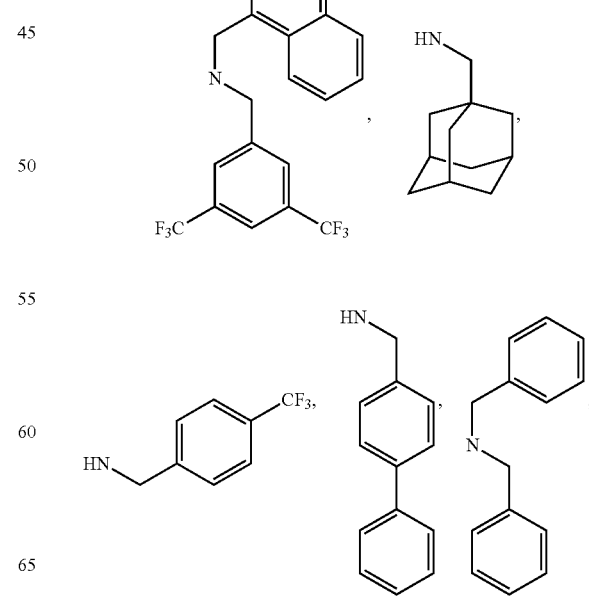

97
-continued
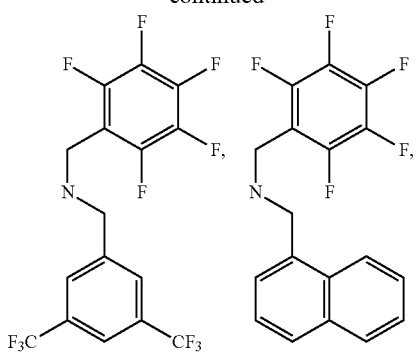
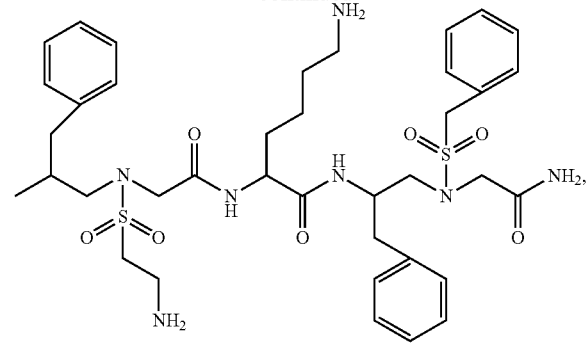
98
-continued
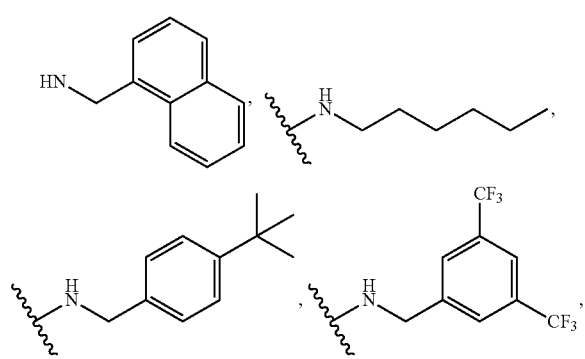
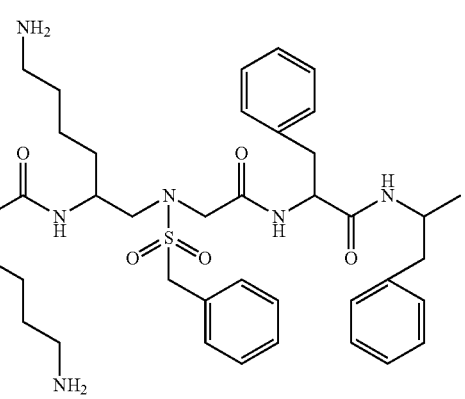
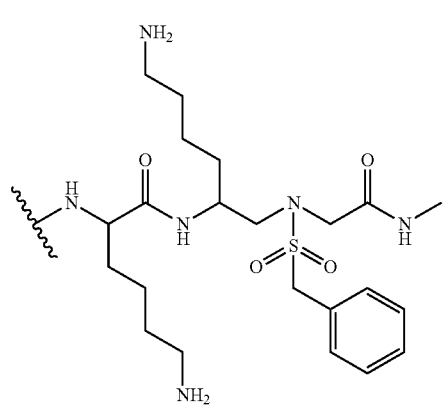
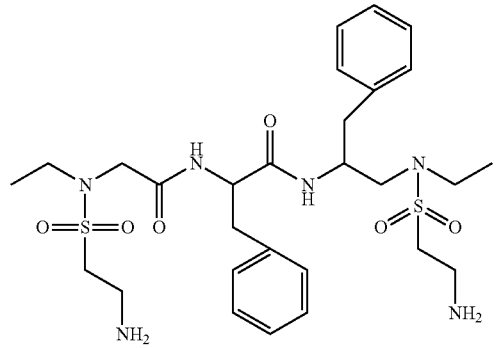
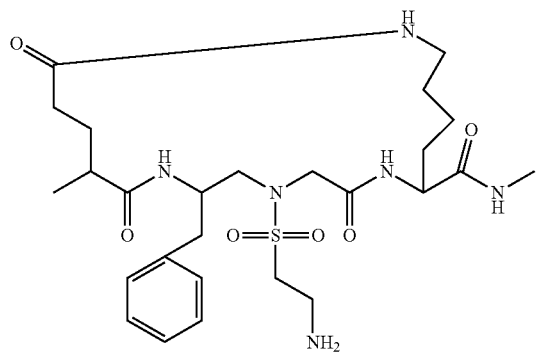
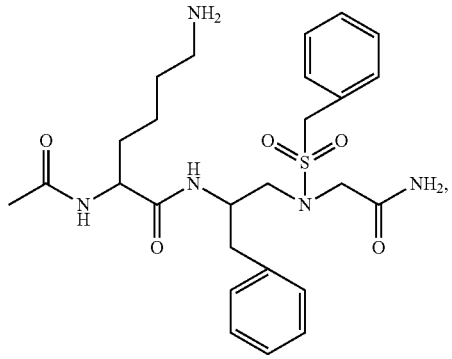

99
-continued
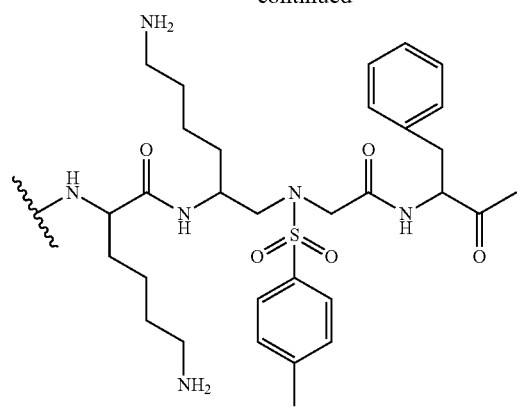
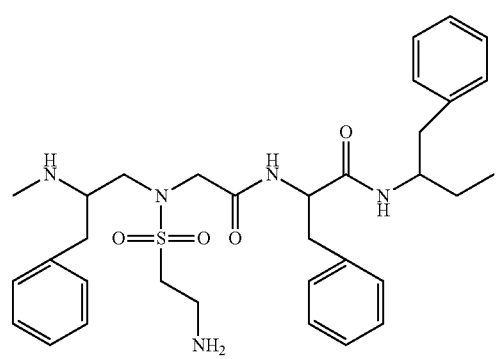
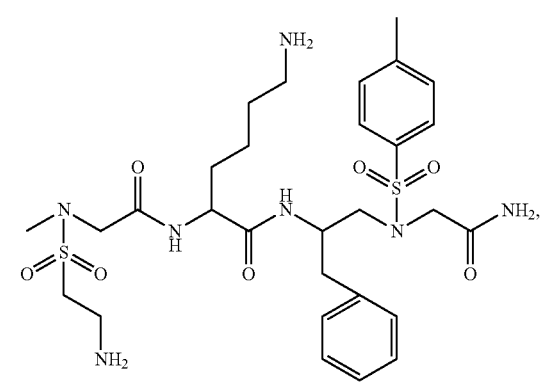
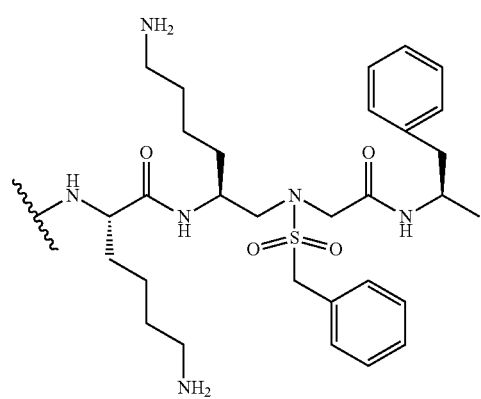
100
-continued
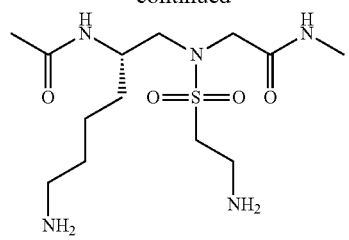
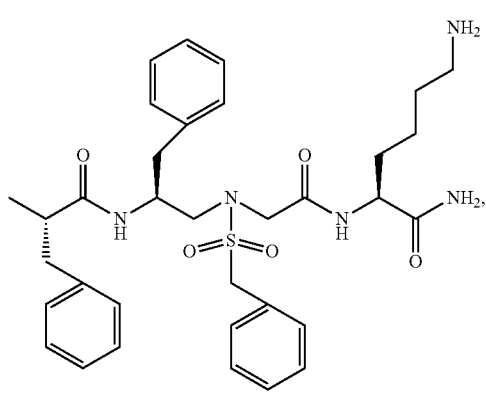
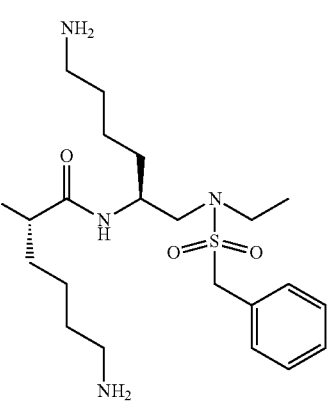
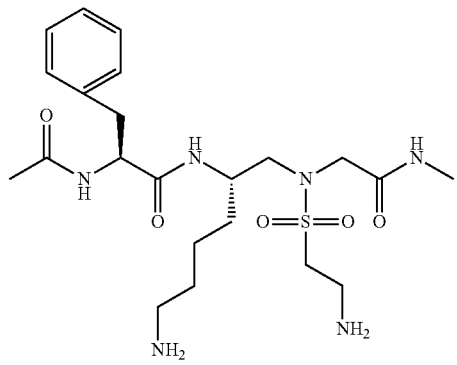

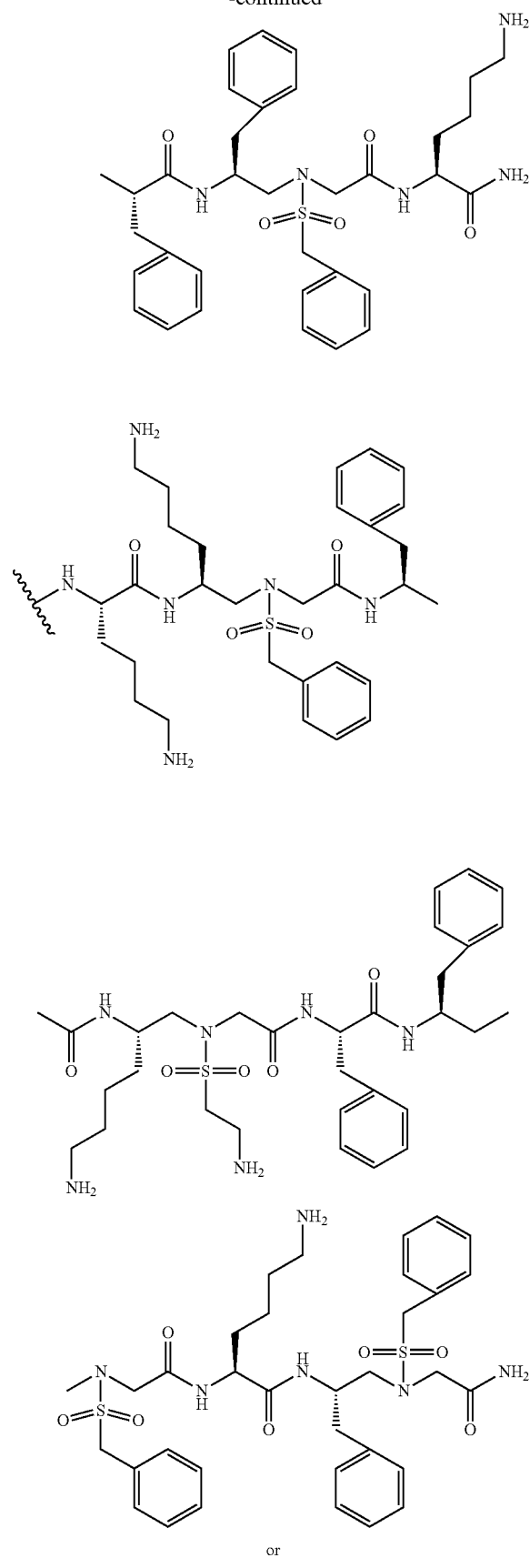
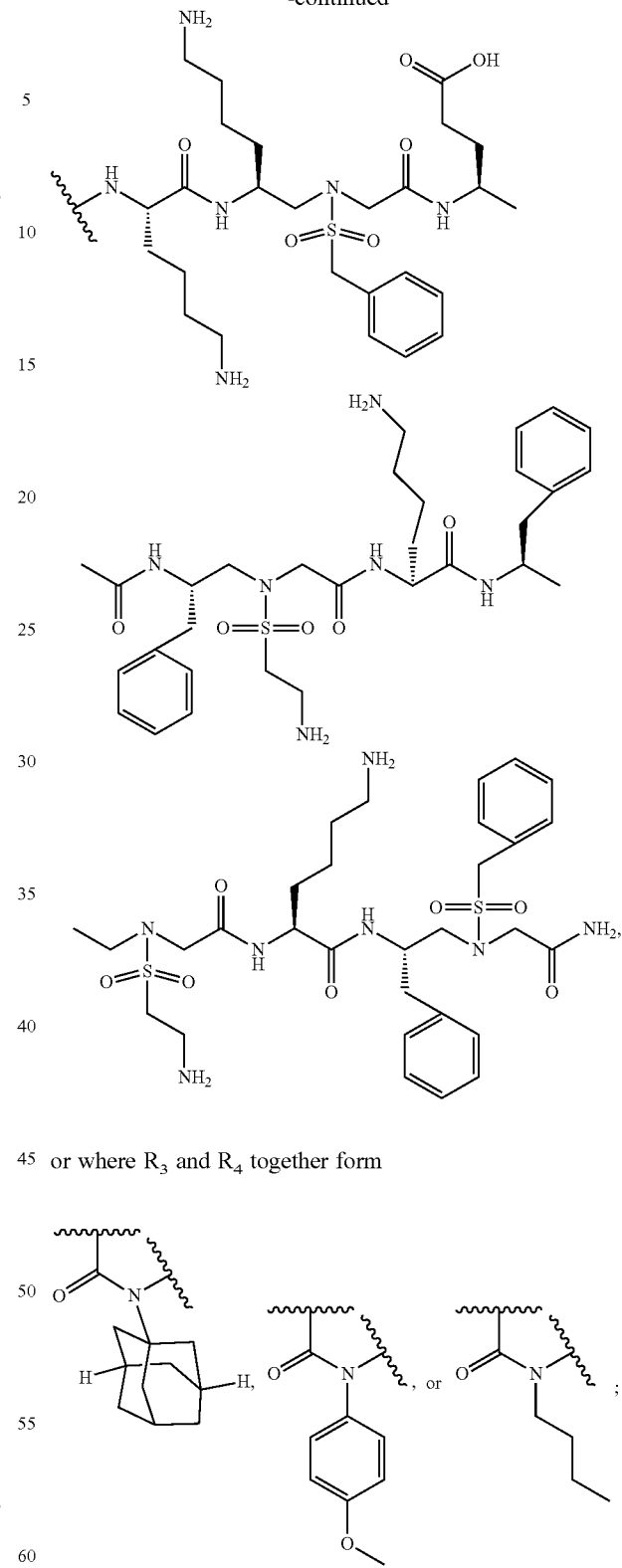
or where R₃ and R₄ together form
and
a pharmaceutically acceptable carrier.
2. The pharmaceutical formulation of claim 1, wherein the compound is compound 15, 16, 17, 18, 19, 20, 21, 24, 25, 26, 27, 32, 33, 34, 35, or 47

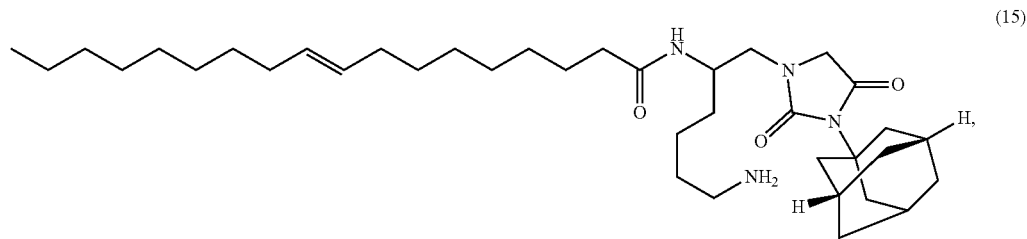
(15)
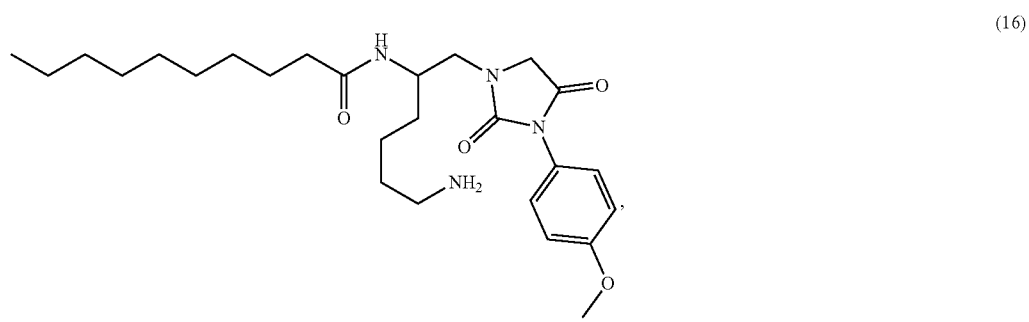
(16)
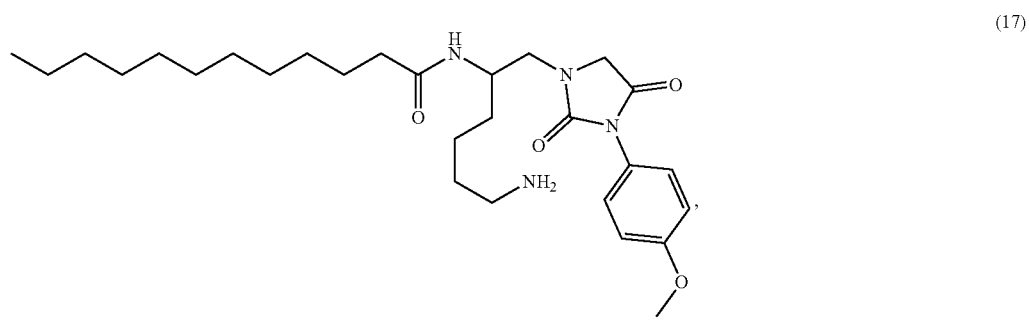
(17)
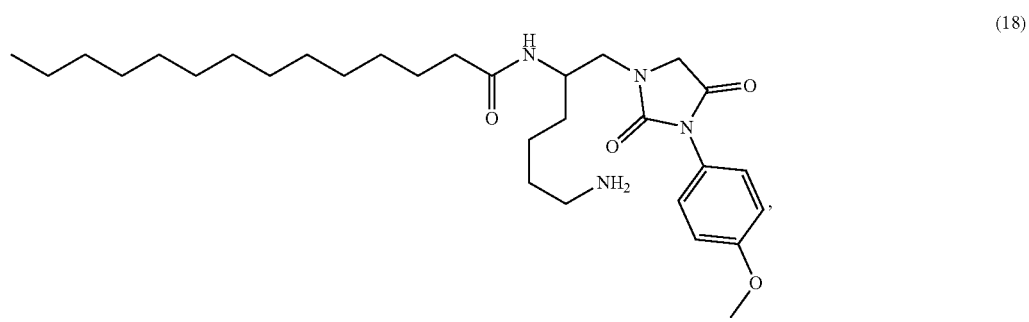
(18)
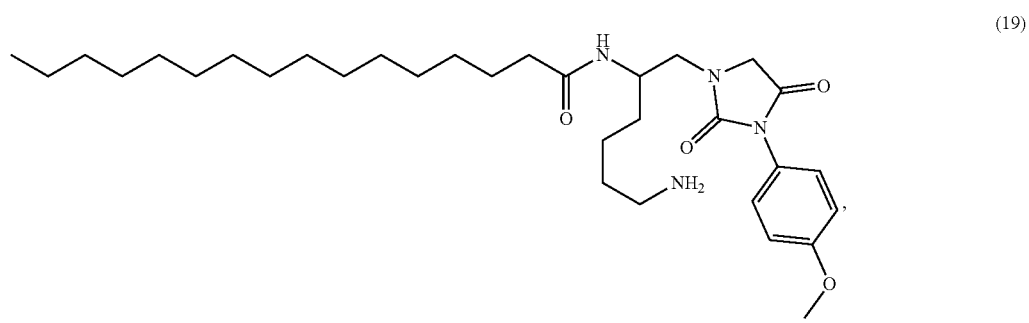
(19)

-continued
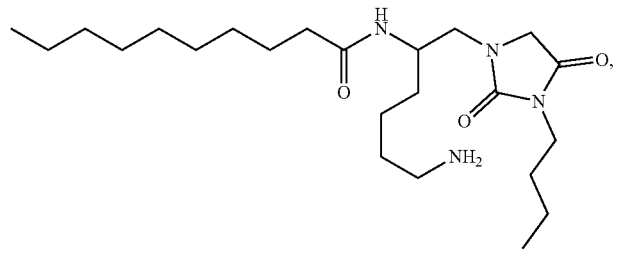
(20)
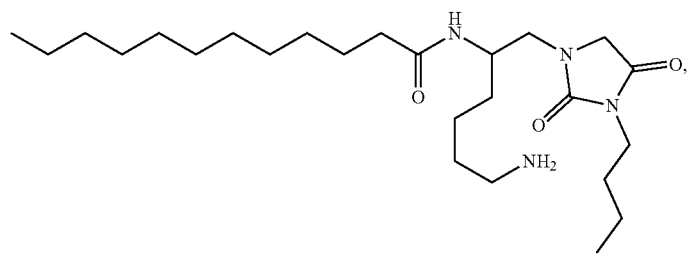
(21)
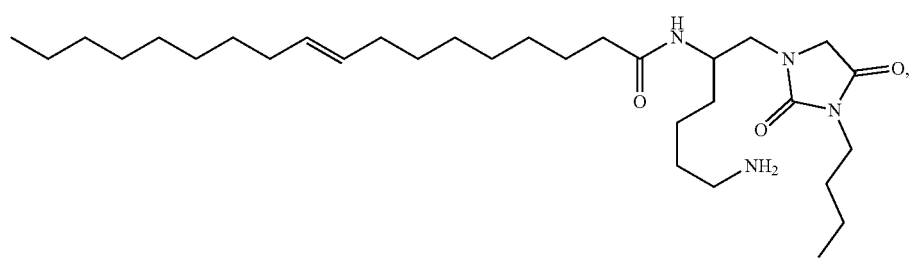
(24)
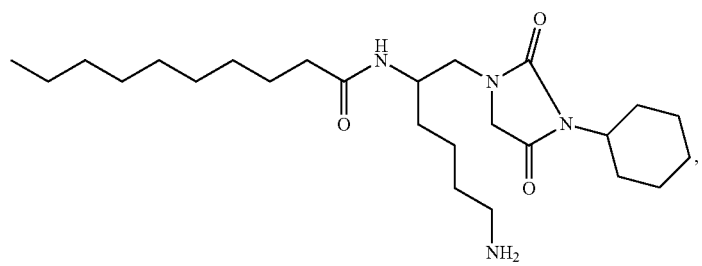
(25)
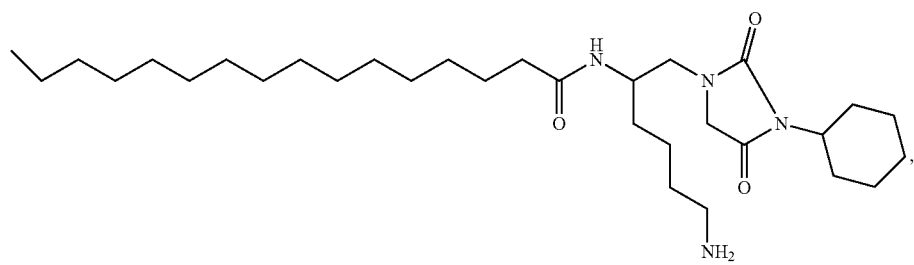
(26)
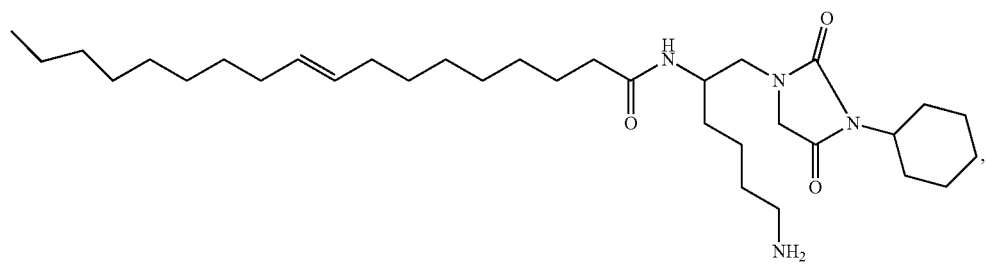
(27)

(32)
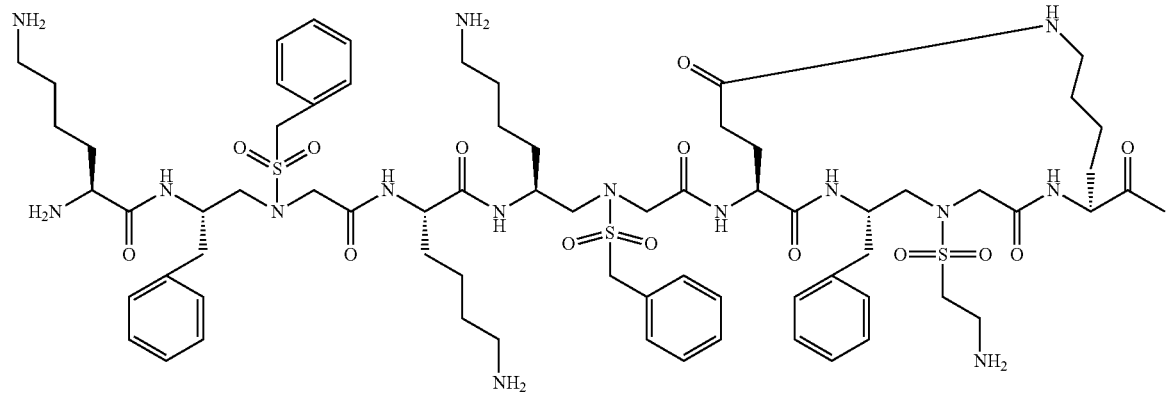
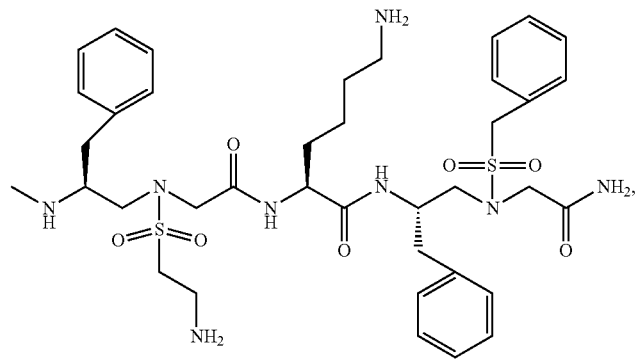
(33)
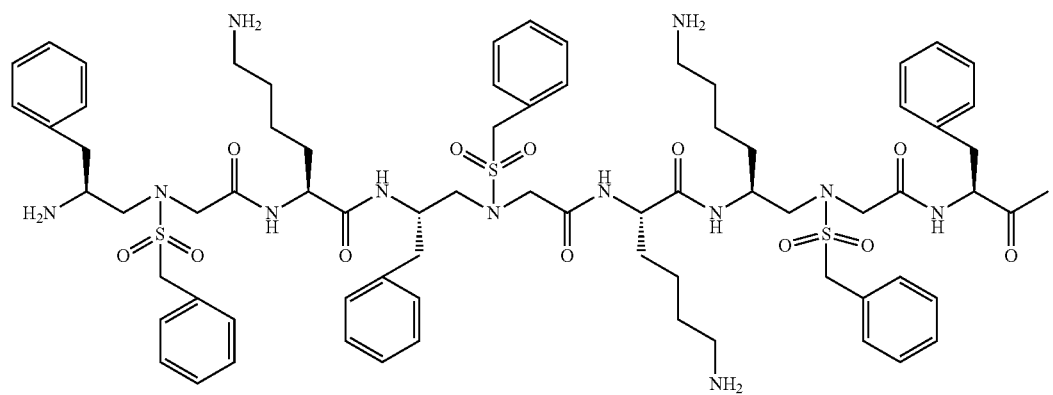
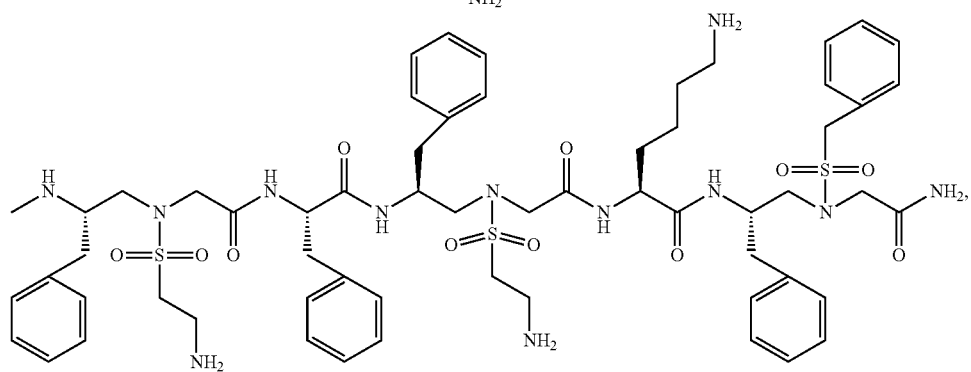

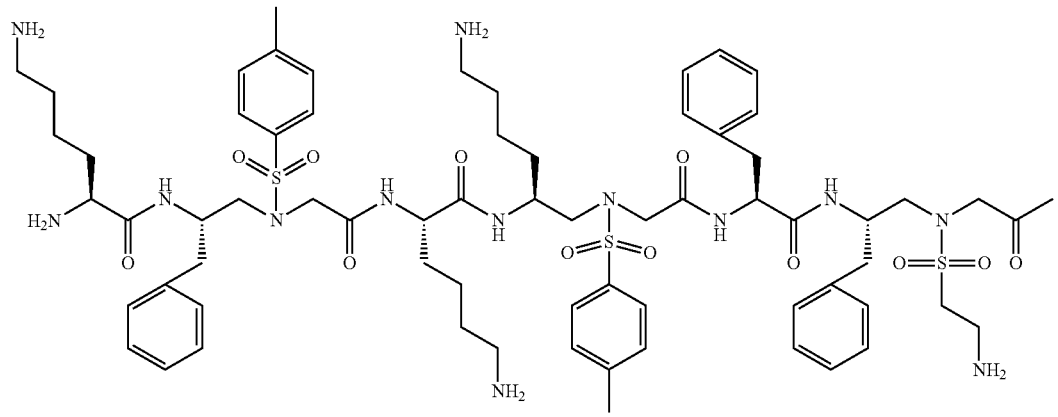
(34)
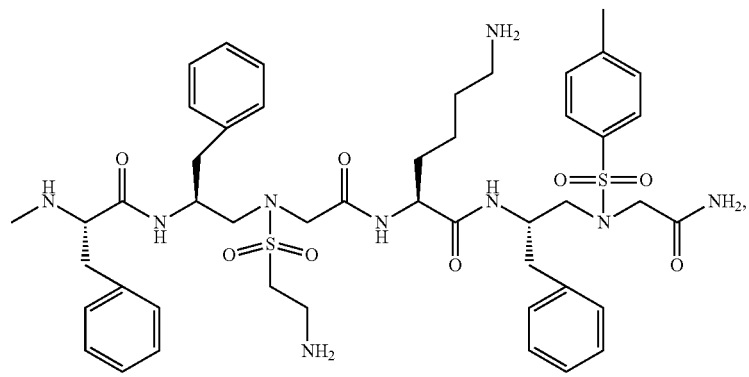
$C_{78}H_{116}N_{16}O_{11}S_2$,
(35)
(47)
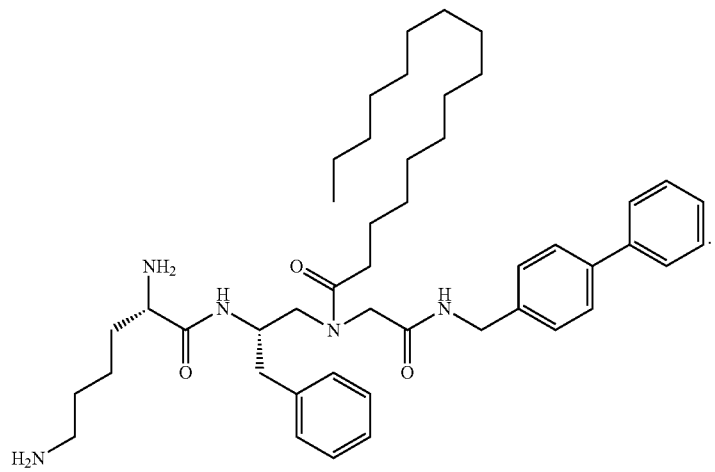

3. The pharmaceutical formulation of claim 1, wherein the compound is compound 5, 8, 9, 10, 11, 12, 13, 14, 38, 39, 40, or 43
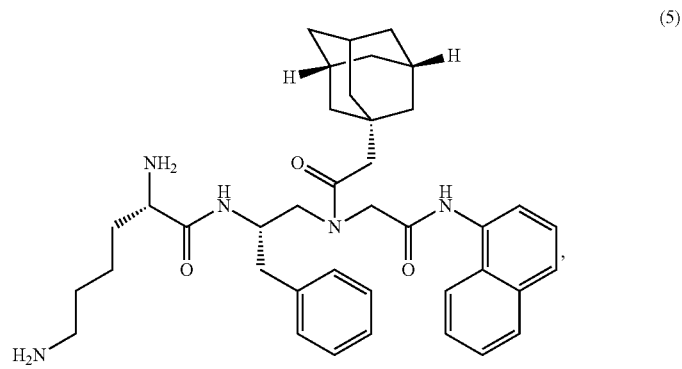
(5)
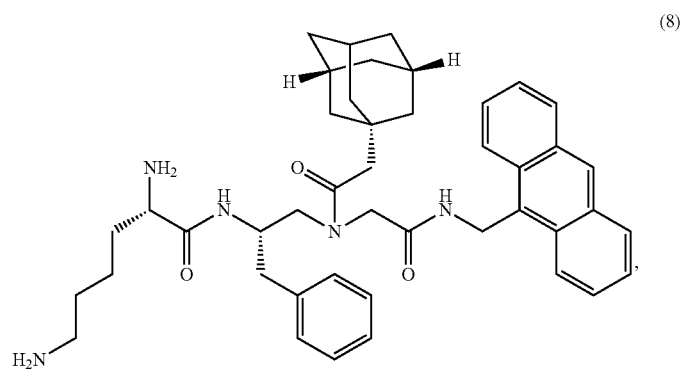
(8)
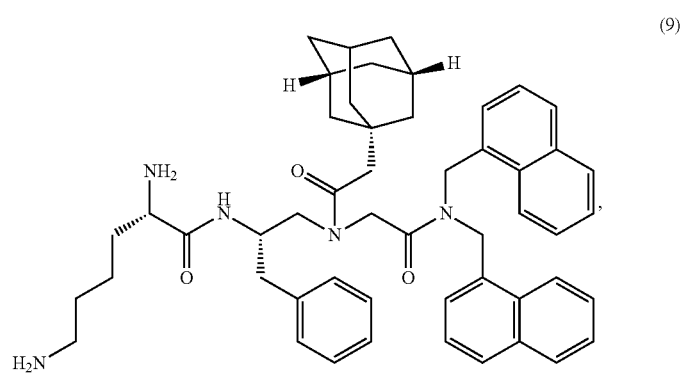
(9)
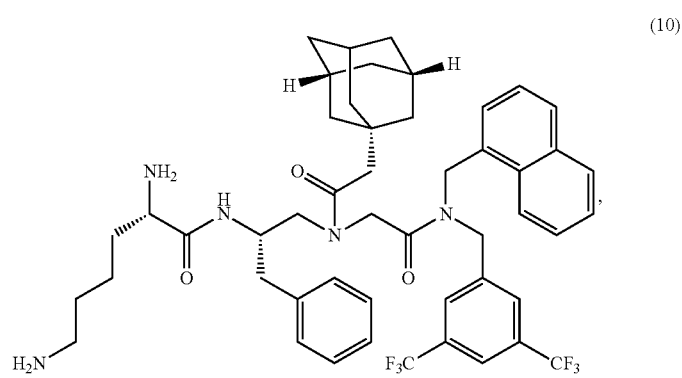
(10)

(11)
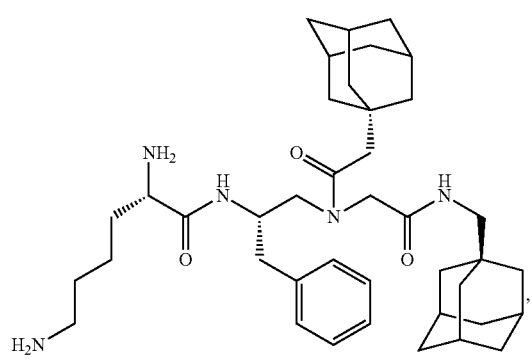
(12)
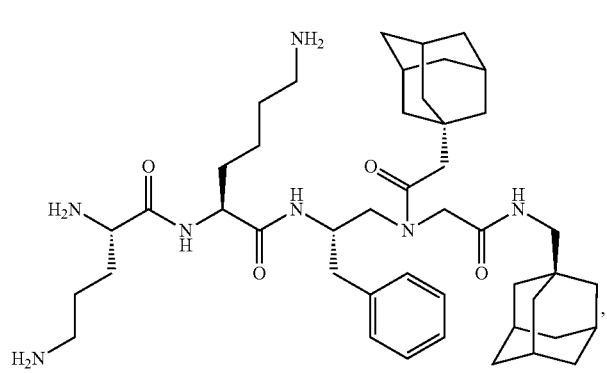
(13)
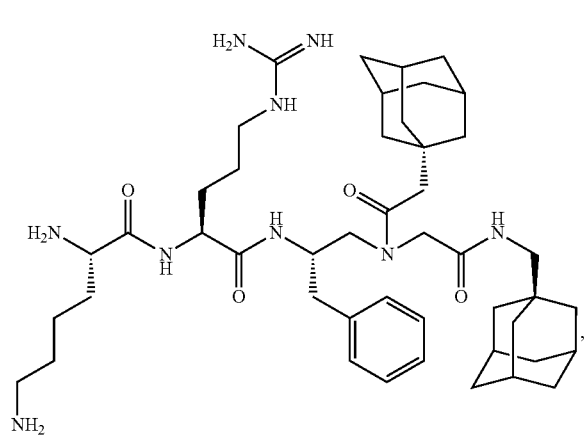
(14)
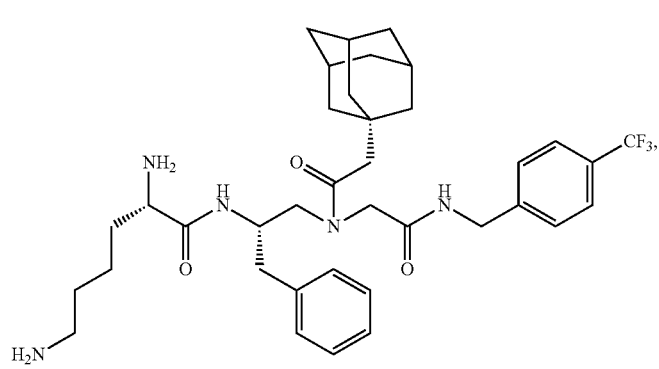

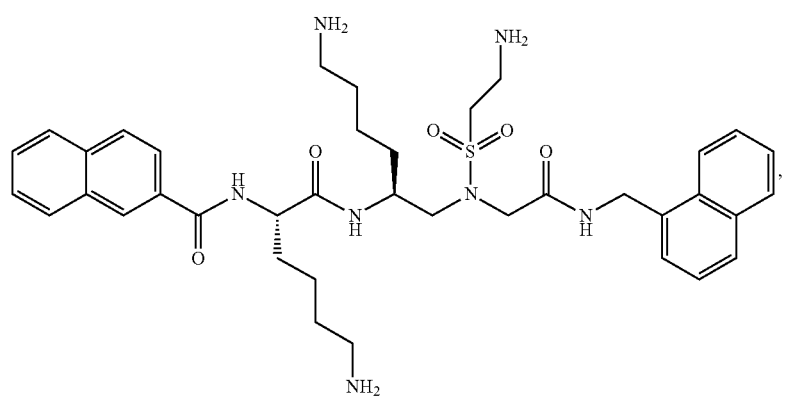
(38)
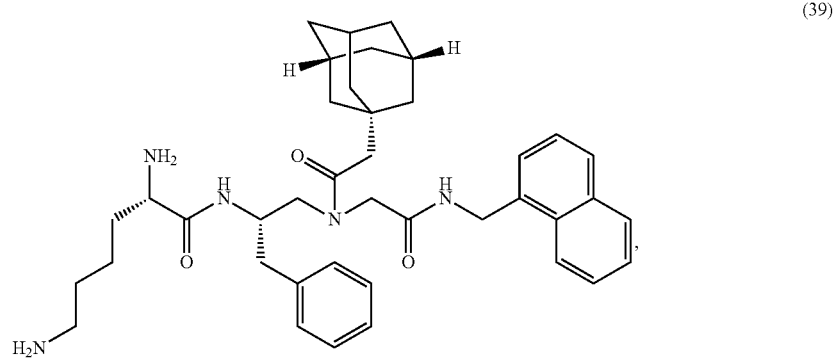
(39)
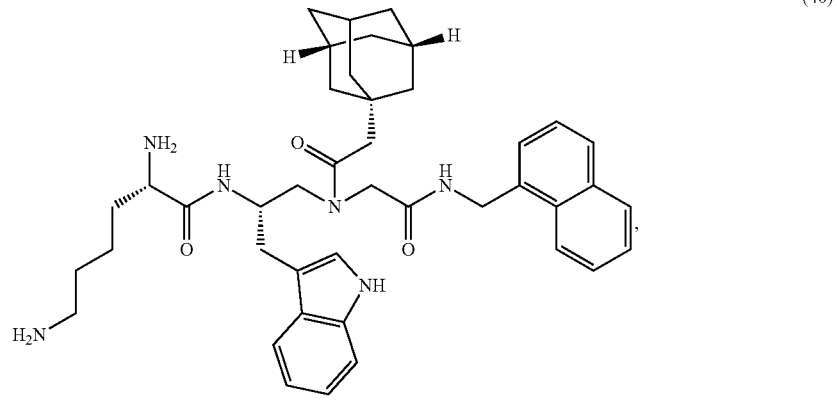
(40)
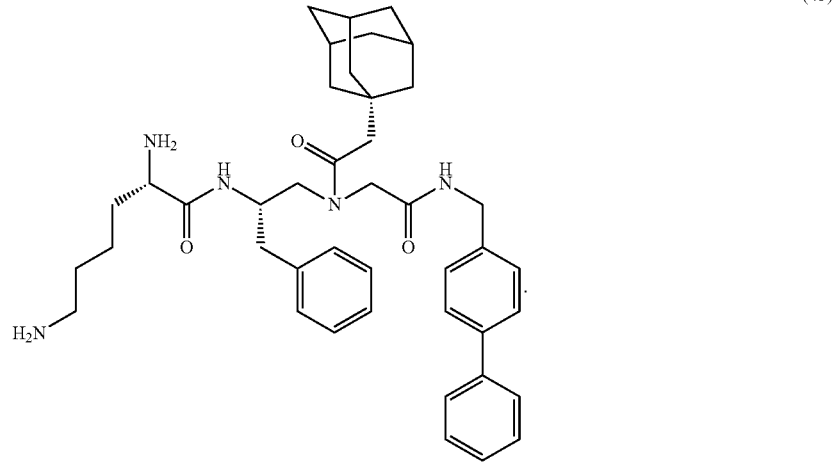
(43)

4. The pharmaceutical formulation of claim 1, wherein the compound is compound 9:
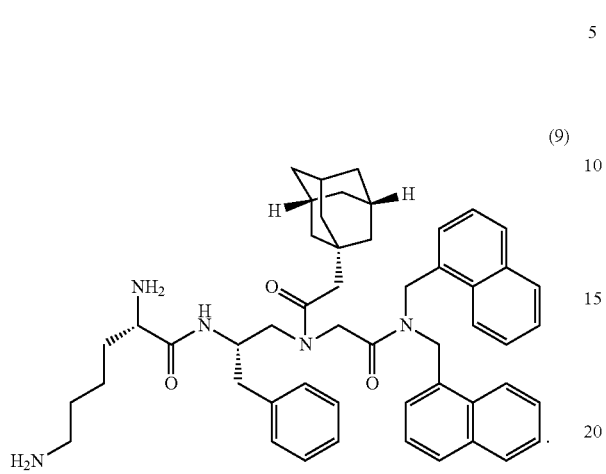
(9)
5. The pharmaceutical formulation of claim 1, wherein the compound is compound 43:
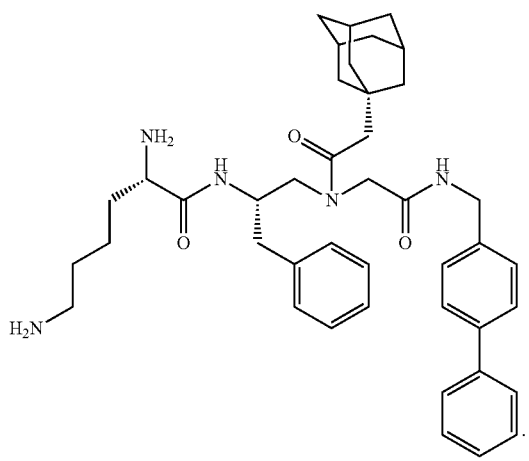
(43)
* * * * *